(12) United States Patent
Dominowski et al.

(10) Patent No.: US 10,953,080 B2
(45) Date of Patent: Mar. 23, 2021

(54) OIL-BASED ADJUVANTS

(71) Applicant: Zoetis Services LLC, Parsippany, NJ (US)

(72) Inventors: Paul Joseph Dominowski, Kalamazoo, MI (US); Dennis L. Foss, Mattawan, MI (US); Guillermo Gallo, Kalamazoo, MI (US); John Morgan Hardham, Kalamazoo, MI (US); Richard Lee Krebs, Ashland, NE (US); Sandra Ann Marie Lightle, Kalamazoo, MI (US); Suman Mahan, Kalamazoo, MI (US); Sangita Mediratta, Kalamazoo, MI (US); Kaori Mohr, Kalamazoo, MI (US); Duncan Mwangi, Portage, MI (US); Sharath K. Rai, Portage, MI (US); Sarah A. Salmon, Kalamazoo, MI (US); Shaunak Vora, Kalamazoo, MI (US); Lauren Wilmes, Lincoln, NE (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 16/166,455

(22) Filed: Oct. 22, 2018

(65) Prior Publication Data

US 2019/0038737 A1   Feb. 7, 2019

Related U.S. Application Data

(63) Continuation of application No. 14/491,414, filed on Sep. 19, 2014, now Pat. No. 10,117,921.

(60) Provisional application No. 61/879,959, filed on Sep. 19, 2013.

(51) Int. Cl.
| | | |
|---|---|---|
| A61K 39/00 | (2006.01) | |
| A61K 39/39 | (2006.01) | |
| A61K 9/107 | (2006.01) | |
| A61K 39/12 | (2006.01) | |
| A61K 39/07 | (2006.01) | |
| A61K 39/09 | (2006.01) | |
| A61K 39/012 | (2006.01) | |
| A61K 39/108 | (2006.01) | |
| A61K 39/05 | (2006.01) | |
| A61K 39/08 | (2006.01) | |
| A61K 39/118 | (2006.01) | |
| A61K 39/002 | (2006.01) | |
| A61K 39/085 | (2006.01) | |
| G01N 33/569 | (2006.01) | |

(52) U.S. Cl.
CPC ........ *A61K 39/092* (2013.01); *A61K 39/0002* (2013.01); *A61K 39/002* (2013.01); *A61K 39/0003* (2013.01); *A61K 39/0005* (2013.01); *A61K 39/012* (2013.01); *A61K 39/0258* (2013.01); *A61K 39/05* (2013.01); *A61K 39/08* (2013.01); *A61K 39/085* (2013.01); *A61K 39/118* (2013.01); *A61K 39/12* (2013.01); *A61K 39/39* (2013.01); *G01N 33/56944* (2013.01); *A61K 2039/552* (2013.01); *A61K 2039/55561* (2013.01); *A61K 2039/55566* (2013.01); *A61K 2039/55572* (2013.01); *A61K 2039/55577* (2013.01); *A61K 2039/55583* (2013.01); *G01N 2333/315* (2013.01); *G01N 2469/10* (2013.01); *Y02A 50/30* (2018.01)

(58) Field of Classification Search
CPC .......... A61K 2039/55566; A61K 39/39; A61K 9/1075; A61K 2039/543; A61K 2039/55561
See application file for complete search history.

(56) References Cited

U.S. PATENT DOCUMENTS

| | | |
|---|---|---|
| 5,026,546 A | 6/1991 | Hilgers et al. |
| 5,057,540 A | 10/1991 | Kensil et al. |
| 5,109,026 A | 4/1992 | Hoskinson et al. |
| 5,679,354 A | 10/1997 | Morein et al. |
| 6,214,806 B1 | 4/2001 | Krieg et al. |
| 6,406,705 B1 | 6/2002 | Davis et al. |
| 6,764,682 B1 | 7/2004 | Kandil et al. |
| 6,846,489 B1 | 1/2005 | Garcon et al. |
| 7,038,029 B2 | 5/2006 | Lopez |
| 7,122,191 B2 | 10/2006 | Dominowski et al. |
| 7,488,490 B2 | 2/2009 | Davis et al. |
| 7,736,658 B2 | 6/2010 | Dominowski et al. |
| 8,088,388 B2 | 1/2012 | Sokoll |

(Continued)

FOREIGN PATENT DOCUMENTS

| | | |
|---|---|---|
| CN | 101954080 B | 11/2013 |
| EP | 1005368 B1 | 9/2009 |

(Continued)

OTHER PUBLICATIONS

Lacaille-Dubois and Wagner, "A review of the biological and pharmacological activities of saponins", Phytomedicine, 2(4):363-386, 1996.

(Continued)

*Primary Examiner* — Barry A Chestnut
(74) *Attorney, Agent, or Firm* — Vyacheslav Vasilyev

(57) ABSTRACT

The instant invention provides various formulations comprising combinations of immunostimulating oligonucleotides, polycationic carriers, sterols, saponins, quaternary amines, TLR-3 agonists, glycolipids, and MPL-A or analogs thereof in oil emulsions, use thereof in preparations of immunogenic compositions and vaccines, and use thereof in the treatment of animals.

13 Claims, No Drawings
Specification includes a Sequence Listing.

(56) References Cited

U.S. PATENT DOCUMENTS

| | | | |
|---|---|---|---|
| 8,460,679 | B2 | 6/2013 | Mannan et al. |
| 8,551,495 | B2 | 10/2013 | Wang |
| 8,580,280 | B2 | 11/2013 | Dominowski et al. |
| 9,056,095 | B2 | 6/2015 | Nishio et al. |
| 9,457,075 | B2 | 10/2016 | Seago et al. |
| 2001/0044416 | A1 | 11/2001 | McCluskie et al. |
| 2002/0132995 | A1 | 9/2002 | Agrawal et al. |
| 2002/0164341 | A1 | 11/2002 | Davis et al. |
| 2002/0197269 | A1 | 12/2002 | Lingnau et al. |
| 2003/0060440 | A1 | 3/2003 | Klinman et al. |
| 2003/0064079 | A1 | 4/2003 | Goudie et al. |
| 2003/0072762 | A1 | 4/2003 | van de Winkel et al. |
| 2003/0086938 | A1 | 5/2003 | Jensen et al. |
| 2003/0099668 | A1 | 5/2003 | Bachmann et al. |
| 2003/0118635 | A1 | 6/2003 | Dalsgaard et al. |
| 2003/0119774 | A1 | 6/2003 | Foldvari et al. |
| 2003/0125292 | A1 | 7/2003 | Semple et al. |
| 2003/0129221 | A1 | 7/2003 | Semple et al. |
| 2003/0144229 | A1 | 7/2003 | Klinman et al. |
| 2003/0148976 | A1 | 8/2003 | Krieg et al. |
| 2003/0162738 | A1 | 8/2003 | Egyed et al. |
| 2003/0181406 | A1 | 9/2003 | Schetter et al. |
| 2003/0224010 | A1 | 12/2003 | Davis et al. |
| 2003/0232074 | A1 | 12/2003 | Lipford et al. |
| 2003/0236211 | A1 | 12/2003 | Agrawal et al. |
| 2004/0006010 | A1 | 1/2004 | Carson et al. |
| 2004/0009897 | A1 | 1/2004 | Sokoll |
| 2004/0009949 | A1 | 1/2004 | Krieg et al. |
| 2004/0018508 | A1 | 1/2004 | Friedman |
| 2004/0047869 | A1 | 3/2004 | Garcon et al. |
| 2004/0191214 | A1 | 9/2004 | Lau et al. |
| 2004/0235778 | A1 | 11/2004 | Wagner et al. |
| 2004/0247662 | A1 | 12/2004 | Dow et al. |
| 2004/0248831 | A1 | 12/2004 | Lingnau et al. |
| 2004/0258701 | A1 | 12/2004 | Dominowski et al. |
| 2004/0266719 | A1 | 12/2004 | McCluskie et al. |
| 2005/0152873 | A1 | 7/2005 | Campbell et al. |
| 2005/0163806 | A1 | 7/2005 | Ahn et al. |
| 2005/0182017 | A1 | 8/2005 | Krieg |
| 2005/0220814 | A1 | 10/2005 | Dominowski et al. |
| 2005/0238660 | A1 | 10/2005 | Babiuk et al. |
| 2005/0239701 | A1 | 10/2005 | Baker et al. |
| 2005/0250716 | A1 | 11/2005 | Schmidt et al. |
| 2005/0287157 | A1 | 12/2005 | Glenn et al. |
| 2006/0003955 | A1 | 1/2006 | Krieg et al. |
| 2006/0008519 | A1 | 1/2006 | Davidsen et al. |
| 2006/0074039 | A1 | 4/2006 | Klinman et al. |
| 2006/0177458 | A1 | 8/2006 | Kensil |
| 2006/0189550 | A1 | 8/2006 | Jiang et al. |
| 2006/0251674 | A1 | 9/2006 | Dominowski et al. |
| 2006/0228342 | A1 | 10/2006 | Ramirez-Pineda et al. |
| 2006/0239963 | A1 | 10/2006 | Morein et al. |
| 2007/0116709 | A1 | 5/2007 | O'Hagan et al. |
| 2007/0196384 | A1* | 8/2007 | Mannan .......... A61K 39/39 424/201.1 |
| 2008/0025996 | A1 | 1/2008 | Lingnau et al. |
| 2008/0095788 | A1 | 4/2008 | Friede et al. |
| 2008/0152662 | A1 | 6/2008 | Agrawal et al. |
| 2008/0292663 | A1 | 11/2008 | Gerber |
| 2008/0292686 | A1 | 11/2008 | Garcon |
| 2009/0060927 | A1 | 3/2009 | Wagner et al. |
| 2009/0324641 | A1* | 12/2009 | Dominowski ....... A61K 39/215 424/207.1 |
| 2010/0104507 | A1 | 4/2010 | Klinman et al. |
| 2010/0291218 | A1 | 11/2010 | Fearon et al. |
| 2010/0330101 | A1 | 12/2010 | Holmgren et al. |
| 2011/0081366 | A1 | 4/2011 | Krieg |
| 2011/0182927 | A1 | 7/2011 | Raz et al. |
| 2012/0171244 | A1 | 7/2012 | O'Hagan |
| 2012/0315295 | A1 | 12/2012 | Rieder et al. |
| 2013/0302369 | A1 | 11/2013 | Abdelmagid et al. |
| 2013/0309273 | A1 | 11/2013 | Hassett et al. |
| 2015/0306203 | A1 | 10/2015 | Wang |
| 2016/0052973 | A1 | 2/2016 | Kotecha et al. |

FOREIGN PATENT DOCUMENTS

| | | | |
|---|---|---|---|
| EP | 2172216 | A2 | 4/2010 |
| RU | 2593718 | C1 | 8/2016 |
| WO | WO 88/01177 | A1 | 2/1988 |
| WO | WO 94/04174 | A1 | 3/1994 |
| WO | WO 95/34308 | A2 | 12/1995 |
| WO | WO 98/48835 | A1 | 11/1998 |
| WO | WO 00/41720 | A1 | 7/2000 |
| WO | WO 00/67023 | A1 | 11/2000 |
| WO | WO 03/003941 | A2 | 1/2003 |
| WO | WO 03/017755 | A2 | 3/2003 |
| WO | WO 03/028760 | A2 | 4/2003 |
| WO | WO 03/089642 | A1 | 10/2003 |
| WO | WO 2004/041720 | A1 | 5/2004 |
| WO | WO 2004/067031 | A1 | 8/2004 |
| WO | WO 2004/084940 | A1 | 10/2004 |
| WO | WO2006002642 | * | 1/2006 |
| WO | WO 2007/125940 | A1 | 11/2007 |
| WO | WO 2008/157659 | A1 | 12/2008 |
| WO | WO 2014077825 | | 5/2014 |

OTHER PUBLICATIONS

Ozel et al., "Quaternary Structure of the Immunostimulating Complex (Iscom)", Journal of Ultrastructure and Molecular Structure Research, 102:240-248, 1989.

Gall, "The Adjuvant Activity of Aliphatic Nitrogenous Bases", Immunology, 11:369-386, 1966.

Korsholm et al., "The adjuvant mechanism of cationic dimethyldioctadecylammonium liposomes", Immunology, 121:216-226, 2007.

Katz et al., "Comparison of dimethyl dioctadecyl ammonium bromide, Freund's complete adjuvant and mineral oil for induction of humoral antibodies, cellular immunity and resistance to Newcastle disease virus in chickens", FEMS Immunology and Medicinal Microbiology, 7:303-314, 1993.

Dalloul and Lillehoj, "Poultry Coccidiosis: Recent Advancements in Control Measures and Vaccine Development", Expert Rev. Vaccines, 5(1):143-163, 2006.

Lillehoj et al., "Embryo Vaccination Against Eimeria Tenella and E. Acervulina Infections Using Recombinant Proteins and Cytokine Adjuvants", J. Parasitol., 91(3):666-673, 2005.

Lillehoj et al., "Resistance to Intestinal Coccidiosis Following DNA Immunization with the Cloned 3-1E Eimeria Gene Plus IL-2, IL-15, and IFN-gamma", Avian Diseases, 49:112-117, 2005.

PCT International Search Report, PCT/IB2009/052724, dated Aug. 2, 2010 (6 pages).

PCT International Search Report, PCT/US2014/056512, dated May 11, 2015 (9 pages).

Autran et al., "Therapeutic Vaccines for Chronic Infections", Science, 305:205-208, 2004.

Mahdavi and Monk, "Vaccines Against Human Papillomavirus and Cervical Cancer: Promises and Challenges", The Oncologist, 10:528-538, 2005.

Usinger, "A comparison of antibody responses to veterinary vaccine antigens potentiated by different adjuvants", Vaccine, 15(17/18):1902-1907, 1997.

Rajput et al., "Adjuvant effects of saponins on animal immune responses", Journal of Zhejiang University Science B, 8(3):153-161, 2007.

Evans et al., "Characterization and Biological Evaluation of a Microparticle Adjuvant Formulation for Plasmid DNA Vaccines", Journal of Pharmaceutical Sciences, 93(7):1924-1939, 2004.

Carcaboso et al., "Potent, long lasting systemic antibody levels and mixed Th1/Th2 immune response after nasal immunization with malaria antigen loaded PLGA microparticles", Vaccine, 22(11-12):1423-1432, 2004.

Hoover et al., "Efficacy of an Inactivated Feline Leukemia Virus Vaccine", AIDS Research and Human Retroviruses, 12(5):379-383, 1996.

Yamamoto et al., "Experimental Vaccine Protection Against Feline Immunodeficiency Virus", AIDS Research and Human Retroviruses, 7(11):911-922, 1991.

(56) References Cited

OTHER PUBLICATIONS

Perez Filgueira et al., "Passive protection to bovine rotavirus (BRV) infection induced by a BRV VP8 produced in plants using a TMV-based vector", Arch. Virol., 149(12):2337-2348, 2004.
Karaca et al., "Evaluation of the ability of canarypox-vectored equine influenza virus vaccines to induce humoral immune responses against canine influenza viruses in dogs", Am. J. Vet. Res., 68(2):208-212, 2007.
Berezin et al., "Immunostimulating complexes incorporating Eimeria tenella antigens and plant saponins as effective delivery system for coccidia vaccine immunization", J. Parasitol., 94(2):381-385, 2008.
Grego et al., "Development and application of an enzyme-linked immunosorbent assay for detection of bovine viral diarrhea antibody based on Erns glycoprotein expressed in a baculovirus System", J. Vet. Diagn. Invest., 19:21-27, 2007.
Van Drunen Littel-Van Den Hurk et al., "Strategies for induction of protective immunity to bovine herpesvirus-1 in newborn calves with maternal antibodies", Vaccine, 26:3103-3111, 2008.
Ralph et al., "Reticulum cell sarcoma: an effector cell in antibody-dependent cell-mediated immunity", J. Immunol., 114(No. 2/Part 2):898-905, 1975.
G. Wittmann, et al., "Some Investigations on the Adjuvant Mechanism of DEAE Dextran," Archives of Virology 47,pp. 225-235 (1975).
Ioannou, X.P., "CpG-containing oligodeoxynucleotides, in combination with conventional adjuvants, enhance the 1 magnitude and change the bias of the immune responses to a herpesvirus glycoprotein," Vaccine 21 (2002), pp. 127-137.
Duggan, S., "Immunization of heifers against gonadotropin releasing hormone: effectiveness of adjuvants," Animal Science Research Report, 1992, pp. 389-393.
Baechtel, F. S. et al., "Interaction of Antigens with Dimethyldioctadecylammonium Bromide, a Chemically Defined Biological Response Modifier", Cancer Research, 1982, vol. 42 pp. 4959-4963.
Maes, R.F. et al: "Potentiation of FMD Vaccines With Polycationic-Nucleic Acid Complexes", Archives of Virology, (1977) vol. 55, pp. 275-285.
Hogan, J_ S., Smith K.L., Todhunter, D. A., Schoenberger, P.S., 1992, "Field trial to determine efficacy of an *Escherichia coli* J5 mastitis vaccine", J_ Dairy Sci 75:78-84.
Tyler, J.W., Cullor, J.S., Thurmond, M.C., Douglas, V.L., Dellinger, J.D., "Humeral Response in 6 Neonatal Calves Following Immunization with *Escherichia coli* {Strain J5): the Effects of Adjuvant, Age and Colostral Passive Interference", Vet. Immunol. and Immunopathol., 23 (1989), pp. 333-444.
Cox, J.C. and Coulter, A.R., "Adjuvants—A classification and review of their modes of action", Vaccine 1997, vol. 15, No. 3, pp. 248-256.
Jeong, Sook-Hy Ang et al., "Immunization with Hepatitis C Virus-Like Particles Induces Humeral and Cellular Immune Responses in Nonhuman Primates", Journal of Virology, Jul. 2004, pp. 6995-7003.
Mc Cluskie, Michael J_ et al., "Novel Adjuvant Systems", Current Drug Targets—Infectious Disorders, 2001, vol. 1, No. 3, pp. 263-271.
Tagliabue, Aldo et al., "Vaccine adjuvants", Human Vaccines 4:5, pp. 347-349; Sep./Oct. 2008.
Freytag, L.C. et al., "Mucosal adjuvants", Vaccine 23 (2005), pp. 1804-1813.
Spickler et al., "Adjuvants in Veterinary Vaccines: Modes of Action and Adverse Effects," J Vet Intern Med 2003;17:273-281.
Ren et al., "CpG oligodeoxynucleotide and montanide ISA 206 adjuvant combination augments the immune responses of a recombinant FMDV vaccine in cattle," Vaccine 29 (2011) pp. 7960-7965.
Cao, Yimei, Adjuvants for foot-and-mouth disease virus vaccines: recent progress, Expert Rev. Vaccines 13(11), pp. 1377-1385 (2014).
Database WPI/Thomson, Week 201369, Thomson Scientific, London, GB; AN-2013-Q50572, XP-002756880 & CN 103 083 663 A (Jiangsu Agric Sci Inst) May 8, 2013 (May 8, 2013).
RU 1 615 918 C (Vserossijskij Ni Zaschchity ZH [SU]), Jul. 9, 1995 (Jul. 9, 1995), examples 4, 5; tables 6, 7.
Bucafusco, Danilo et al., Foot-and-mouth disease vaccination induces cross-reactive IFN-γ responses in cattle that are dependent on the integrity of the140S particles, Virology 476 (2015), pp. 11-18.
D.T. O'Hagan et al., "Synergistic adjuvant activity of immunostimulatory DNA and oil/water emulsions for immunization with HIV p55 gag antigen", Vaccine 20 (2002), pp. 3389-3398.
Raman et al., "Applying TLR Synergy in Immunotherapy: Implications in Cutaneous Leishmaniasis", The Journal of Immunology, 185(3):1701-1710, 2010.
McCluskie and Weeratna, "Novel Adjuvant Systems", Current Drug Targets—Infectious Disorders, 1(3):263-271, 2001.
Baldwin et al., "The Importance of Adjuvant Formulation in the Development of a Tuberculosis Vaccine", The Journal of Immunology, 188(5):2189-2197, 2012.
Kaufmann et al., "Challenges and responses in human vaccine development", 2014, Current Opinion in immunology, 28:18-26.

* cited by examiner

OIL-BASED ADJUVANTS

This is a continuation of U.S. application Ser. No. 14/491,414 filed on Sep. 19, 2014, now allowed, which is a non-provisional of U.S. Provisional Application Ser. No. 61/879,959 filed Sep. 19, 2013.

FIELD OF THE INVENTION

This invention relates generally to novel adjuvant formulations for enhancing the immune response to antigens for use in immunogenic and vaccine compositions. This invention also relates to methods of preparation and use of the adjuvant, immunogenic, and vaccine compositions.

BACKGROUND

Bacterial, viral, and parasitic infections are wide spread in humans and animals. Diseases caused by these infectious agents are often resistant to antimicrobial pharmaceutical therapy, leaving no effective means of treatment. Consequently, a vaccinology approach is increasingly used to control infectious disease. A whole infectious pathogen can be made suitable for use in a vaccine formulation after chemical inactivation or appropriate genetic manipulation. Alternatively, a protein subunit of the pathogen can be expressed in a recombinant expression system and purified for use in a vaccine formulation. Vaccines can be made more efficacious by including an appropriate adjuvant in the composition.

The term 'adjuvant' generally refers to any material that increases the humoral or cellular immune response to an antigen. Adjuvants are used to accomplish two objectives: They slow the release of antigens from the injection site, and they enhance stimulation of the immune system. Traditional vaccines are generally composed of a crude preparation of inactivated or killed or modified live pathogenic microorganisms. The impurities associated with these cultures of pathological microorganisms may act as an adjuvant to enhance the immune response. However, the immunity invoked by vaccines that use homogeneous preparations of pathological microorganisms or purified protein subunits as antigens is often poor. The addition of certain exogenous materials such as an adjuvant therefore becomes necessary. Further, in some cases, synthetic and subunit vaccines may be expensive to produce. Also, in some cases, the pathogen cannot be grown on a commercial scale, and thus, synthetic/subunit vaccines represent the only viable option. The addition of an adjuvant may permit the use of a smaller dose of antigen to stimulate a similar immune response, thereby reducing the production cost of the vaccine. Thus, the effectiveness of some injectable medicinal agents may be significantly increased when the agent is combined with an adjuvant.

Many factors must be taken into consideration in the selection of an adjuvant. An adjuvant should cause a relatively slow rate of release and absorption of the antigen in an efficient manner with minimum toxic, allergenic, irritating, and other undesirable effects to the host. To be desirable, an adjuvant should be non-viricidal, biodegradable, capable of consistently creating a high level of immunity, capable of stimulating cross protection, compatible with multiple antigens, efficacious in multiple species, non-toxic, and safe for the host (eg, no injection site reactions). Other desirable characteristics of an adjuvant are that it is capable of micro-dosing, is dose sparing, has excellent shelf stability, is amenable to drying, can be made oil-free, can exist as either a solid or a liquid, is isotonic, is easily manufactured, and is inexpensive to produce. Finally, it is highly desirable for an adjuvant to be configurable so as to induce either a humoral or cellular immune response or both, depending on the requirements of the vaccination scenario. However, the number of adjuvants that can meet the above requirements is limited.

The choice of an adjuvant depends upon the needs for the vaccine, whether it be an increase in the magnitude or function of the antibody response, an increase in cell mediated immune response, an induction of mucosal immunity, or a reduction in antigen dose. A number of adjuvants have been proposed, however, none has been shown to be ideally suited for all vaccines. The first adjuvant reported in the literature was Freund's Complete Adjuvant (FCA) which contains a water-in-oil emulsion and extracts of *mycobacterium*. Unfortunately, FCA is poorly tolerated and it can cause uncontrolled inflammation. Since the discovery of FCA over 80 years ago efforts have been made to reduce the unwanted side effects of adjuvants.

Some other materials that have been used as adjuvants include metallic oxides (e.g., aluminum hydroxide), alum, inorganic chelates of salts, gelatins, various paraffin-type oils, synthesized resins, alginates, mucoid and polysaccharide compounds, caseinates, and blood-derived substances such as fibrin clots. While these materials are generally efficacious at stimulating the immune system, none has been found to be entirely satisfactory due to adverse effects in the host (e.g., production of sterile abcesses, organ damage, carcinogenicity, or allergenic responses) or undesirable pharmaceutical properties (e.g., rapid dispersion or poor control of dispersion from the injection site, or swelling of the material).

SUMMARY OF INVENTION

The instant invention provides novel vaccine compositions and adjuvant formulations useful for vaccines.

In the first aspect, the invention provides an adjuvant formulation comprising an oily phase and an aqueous phase, wherein the oily phase comprises at least 50% of the formulation v/v, wherein said formulation comprises at least one of monophosphoryl lipid A (MPL-A) or an analog thereof and an immunostimulatory oligonucleotide, with provisos that a) if said immunostimulatory oligonucleotide is absent, then the formulation comprises a poly I:C, a glycolipid, and, optionally, a quaternary amine; or a polycationic carrier; and b) if said monophosphoryl lipid A (MPL-A) or the analog thereof is absent, then the formulation comprises a source of aluminum, and, optionally, a polycationic carrier.

In different embodiments, the oily phase may comprise an oil and, optionally, an oil-soluble emulsifier.

In some embodiments, both said monophosphoryl lipid A (MPL-A) or the analog thereof are present in the adjuvant formulation. In these embodiments, the formulation further comprises a sterol (e.g., cholesterol), a poly I:C, or a combination thereof.

In certain set of embodiments, in addition to the oil and the optional emulsifier(s), the adjuvant formulations include a combination of monophosphoryl lipid A (MPL-A) or an analog thereof, a sterol, and an immunostimulatory oligonucleotide ("TCMO"). The adjuvant formulation may also optionally comprise poly I:C ("TCMYO") and/or a saponin ("QTCMO" or "QTCMYO", respectively).

In yet further alternative embodiments, in addition to the oil and the optional emulsifier(s), the adjuvant formulations also include a combination of a quaternary amine, a glycolipid, MPL-A or an analog thereof, and poly I:C ("ODYRM").

In yet further set of embodiments, in addition to the oil and the optional emulsifier(s), the adjuvant formulations also include a combination of a saponin, a sterol, a quaternary amine, a polycationic carrier, with a proviso that if said polycationic carrier is dextran DEAE, then the antigen is not *E. coli* J-5 bacterin ("QCDXO").

In further embodiments, in addition to the oil and the optional emulsifier(s), the adjuvant may include the immunostimulatory oligonucleotide, a source of aluminum, and, optionally, a polycationic carrier ("TOA" and "TXO-A", respectively).

In a second aspect, the adjuvant formulation according any of the embodiments recited above, may include an antigen component, thus forming a vaccine composition, with a proviso that the antigen is not *E. Coli* J-5 protein if the adjuvant formulation consists of (or consists essentially of) DEAE dextran, Quil A, Cholesterol, and DDA, or if the adjuvant formulation consists of (or consists essentially of) of DEAE dextran and the immunostimulatory oligonucleotide. In certain embodiments, the vaccines of this aspect contain antigen(s) derived from pathogens affecting cattle, sheep, horses, or swine. In other embodiments, vaccines of this aspect contain antigen(s) derived from pathogens affecting, poultry or feline animals.

In additional aspects of the invention, different combinations of the antigen compound and the adjuvant formulations are provided.

More specifically, in the third aspect, the invention provides a vaccine composition comprising an *Eimeria maxima* and/or *Clostridium perfringens* antigen and an adjuvant formulation. In different embodiments of this third aspect, the adjuvant formulation may include an oily phase, said oily phase being present in the amount of at least 50% v/v of the composition; a polycationic carrier, and optionally, an immunostimulatory oligonucleotide. In other embodiments of this aspect of the invention, the invention provides a vaccine composition comprising an adjuvant component comprising an oily phase, said oily phase being present in the amount of at least 50% v/v of the composition; an immunostimulatory oligonucleotide, a sterol, and monophosphoryl lipid A (MPL-A) or an analog thereof.

In the fourth aspect, the invention provides a vaccine composition comprising a *Neospora* antigen and an adjuvant formulation. In different embodiments of the invention according to this aspect, the adjuvant formulation comprises an oily phase, said oily phase being present in the amount of at least 50% v/v of the composition; and monophosphoryl lipid A (MPL-A) or an analog thereof. In other embodiments, the adjuvant formulation comprises an oily phase, said oily phase being present in the amount of at least 50% v/v of the composition, an immunostimulatory oligonucleotide and a polycationic carrier.

In the fifth aspect, the invention provides a vaccine composition comprising a *Chlamydophila abortis* antigen and an adjuvant formulation comprising an oily phase, said oily phase being present in the amount of at least 50% v/v of the composition; a sterol; an immunostimulatory oligonucleotide; monophosphoryl lipid A (MPL-A) or an analog thereof; and poly I:C.

In the sixth aspect, the invention provides a vaccine composition comprising a *Streptococcus uberis* (*S. uberis*) antigen and an adjuvant formulation comprising an oily phase, said oily phase being present in the amount of at least 50% v/v of the composition; and a polycationic carrier. In different embodiments of this sixth aspect of the invention, the adjuvant formulation also includes an immunostimulatory oligonucleotide. Alternatively, or additionally, the adjuvant formulations may include a saponin, a sterol, and a quaternary amine.

In the seventh aspect, the invention provides a vaccine composition comprising myostatin as the antigenic component, and an adjuvant formulation, said adjuvant formulation comprising an oily phase, said oily phase being present in the amount of at least 50% v/v of the composition; an immunostimulatory oligonucleotide and either: a polycationic carrier; or MPL-A or an analog thereof. In a set of embodiments according to this aspect of the invention, the adjuvant formulation comprises MPL-A or the analog thereof. In some embodiments of this set, the adjuvant formulation contains less than 0.5 ug of a sterol per 50 ul of said vaccine composition, and preferably does not contain cholesterol. The choice of myostatin depends on the subject species. In one selected embodiment, the select species is chicken and the source of myostatin is chicken myostatin.

In the eighth aspect, the invention provides a vaccine composition comprising an *A. pyogenes* (formerly known as *Arcanobacterium pyogenes, Actinomyces pyogenes* or *Corynebacterium pyogenes*; now known as *Trueperella pyogenes*) antigen and an adjuvant formulation, wherein the adjuvant formulation comprises an oily phase, said oily phase being present in the amount of at least 50% v/v of the composition; an immunostimulatory oligonucleotide and a polycationic carrier.

In the ninth aspect, the invention provides a vaccine composition comprising an *E. coli* antigen, a BRV antigen or a BCV antigen, and an adjuvant formulation, wherein said adjuvant formulation comprises an oily phase present in the amount of at least 50% v/v of said vaccine composition, an immunostimulatory oligonucleotide and at least one of a polycationic carrier and a source of aluminum.

In the tenth aspect, the invention provides a vaccine composition comprising a *Rhipicephalus microplus* antigen and an adjuvant, said adjuvant being selected from the group consisting of: a) an aqueous adjuvant comprising an immunostimulatory oligonucleotide, a saponin, a sterol, a quaternary amine, a polyacrylic polymer, and a glycolipid; and b) an oil-based adjuvant, comprising an oily phase present in the amount of at least 50% v/v of the vaccine composition and comprising an immunostimulatory oligonucleotide and a polycationic carrier.

In the eleventh aspect, the invention provides a vaccine composition comprising a Foot-and-Mouth Disease Virus (FMDV) antigen and an adjuvant formulation, said adjuvant formulation comprising an oily phase present in the amount of at least 50% v/v of said vaccine composition, an immunostimulatory oligonucleotide and a polycationic carrier. In different embodiments, the Foot-and-Mouth Disease Virus antigen may be of either wild-type FMDV, genetically modified and/or attenuated FMDV strains, or recombinantly expressed FMDV structural proteins such as virus like particles (VLPs) of serotypes A, C, O, Asia1, SAT1, SAT2, or SAT3.

In the twelfth aspect, the invention provides a method of generation of diagnostic or therapeutic antibodies, the method comprising immunizing a source animal with the adjuvant formulation according to any of the embodiments according to the first aspect of the invention, and antigen, followed by extracting a source of the antibodies from the source animal and if needed, purifying the antibodies.

In certain embodiments, the source animal is a rat, a mouse, a guinea pig, a hamster, a cattle animal, a goat, a rabbit, a hourse a swine animal or an ovine. In some other embodiments, the source animal is a cat or a dog.

In some embodiments, particularly suitable for polyclonal antibodies, the source of the antibodies is a serum or milk. In embodiments suitable for monoclonal antibodies, the suitable source of antibodies is a spleen cell.

In certain embodiments, the adjuvant formulation comprises an immunostimulatory oligonucleotide and a polycationic carrier. The adjuvant may optionally contain a source of aluminum, comprising the source of aluminum, which may be an aluminum hydroxide gel. In certain embodiments, the immunostimulatory oligonucleotide is a CpG and the polycationic carrier is DEAE dextran.

In certain embodiments, the antigen may be selected from FeLVgp70, Bovine Parainfluenza-3 BPI-3 (HN protein), *Histophilus somni* p31, *Bordetella* FHA, Parapox, BVDV1 gp53, BVDV2 gp53, Clostridia toxins, Canine Circovirus, *Brachyspira hyodysenteriae* (swine species) Antigens; whole cell inactivated and Pepsin Digest inactivated.

The invention also provides the methods of use of the vaccines according to the third through twelfth aspects of the instant invention.

DETAILED DESCRIPTION OF SELECTED EMBODIMENTS

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater, unless about is used in reference to time intervals in weeks where "about 3 weeks," is 17 to 25 days, and about 2 to about 4 weeks is 10 to 40 days.

"Adjuvant" means any substance that increases the humoral or cellular immune response to an antigen. Adjuvants are generally used to accomplish two objectives: the controlled release of antigens from the injection site, and the stimulation of the immune system.

"Adjuvant formulation" refers to formulations having adjuvanting properties.

"Alkyl" refers to both straight and branched saturated hydrocarbon moieties.

"Amine" refers to a chemical compound containing nitrogen. Amines are a group of compounds derived from ammonia by substituting hydrocarbon groups for the hydrogen atoms. "Quaternary amine" refers to an ammonium based compound with four hydrocarbon groups.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that is recognized by the animal's immune system and generates an immune response. The term includes killed, inactivated, attenuated, or modified live bacteria, viruses, or parasites. The term "antigen" also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Bacterin" means a suspension of one or more killed bacteria which may be used as a component of a vaccine or immunogenic composition.

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Cellular immune response" or "cell mediated immune response" is one mediated by T-lymphocytes or other white blood cells or both, and includes the production of cytokines, chemokines and similar molecules produced by activated T-cells, white blood cells, or both; or a T lymphocyte or other immune cell response that kills an infected cell.

"Companion animals" refers to dogs, cats and equines.

"Consisting essentially" as applied to the adjuvant formulations refers to formulation which does not contain unrecited additional adjuvanting or immunomodulating agents in the amounts at which said agent exert measurable adjuvanting or immunomodulating effects.

"Delayed type hypersensitivity (DTH)" refers to an inflammatory response that develops 24 to 72 hours after exposure to an antigen that the immune system recognizes as foreign. This type of immune response involves mainly T cells rather than antibodies (which are made by B cells).

"Dose" refers to a vaccine or immunogenic composition given to a subject. A "first dose" or "priming vaccine" refers to the dose of such a composition given on Day 0. A "second dose" or a "third dose" or an "annual dose" refers to an amount of such composition given subsequent to the first dose, which may or may not be the same vaccine or immunogenic composition as the first dose.

The term "emulsifier" is used broadly in the instant disclosure. It includes substances generally accepted as emulsifiers, e.g., different products of TWEEN® or SPAN® product lines (fatty acid esters of polyethoxylated sorbitol and fatty-acid-substituted sorbitan surfactants, respectively), and different solubility enhancers such as PEG-40 Castor Oil or another PEGylated hydrogenated oil.

"Humoral immune response" refers to one that is mediated by antibodies.

"Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus an immunogenic composition would be any composition that induces an immune response.

"Immunostimulatory molecule" refers to a molecule that stimulates a non-antigen-specific immune response.

"Lipids" refers to any of a group of organic compounds, including the fats, oils, waxes, sterols, and triglycerides that are insoluble in water but soluble in nonpolar organic solvents, are oily to the touch, and together with carbohydrates and proteins constitute the principal structural material of living cells.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

The term "Poly I:C" refers to naturally occurring polymers of polyinosinic:polycytadylic acids as well as synthetic forms thereof, e.g., with stabilized backbone and preferably having TLR-3 agonist activity.

"Reactogenicity" refers to the side effects elicited in a subject in response to the administration of an adjuvant, an immunogenic, or a vaccine composition. It can occur at the site of administration, and is usually assessed in terms of the development of a number of symptoms. These symptoms can include inflammation, redness, and abscess. It is also assessed in terms of occurrence, duration, and severity. A "low" reaction would, for example, involve swelling that is only detectable by palpitation and not by the eye, or would be of short duration. A more severe reaction would be, for example, one that is visible to the eye or is of longer duration.

"Room Temperature" means a temperature from 18 to 25° C.

"Saponin" refers to a group of surface-active glycosides of plant origin composed of a hydrophilic region (usually several sugar chains) in association with a hydrophobic region of either steroid or triterpenoid structure.

"Steroids" refers to any of a group of organic compounds belonging to biochemical class of lipids, which are easily soluble in organic solvents and slightly soluble in water. Steroids comprise a four-fused ring system of three fused cyclohexane (six-carbon) rings plus a fourth cyclopentane (five-carbon) ring.

"Sterols" refers to compounds in animals which are biologically produced from terpenoid precursors. They comprise a steroid ring structure, having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble.

"Subject" refers to any animal for which the administration of an adjuvant composition is desired. It includes mammals and non-mammals, including primates, livestock, companion animals, laboratory test animals, captive wild animals, aves (including in ova), reptiles, and fish. Thus, this term includes but is not limited to monkeys, humans, swine; cattle, sheep, goats, equines, mice, rats, guinea pigs, hamsters, rabbits, felines, canines, chickens, turkeys, ducks, other poultry, frogs, and lizards.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual, p. 25-46 (1996).

"Therapeutically effective amount" refers to an amount of an antigen or vaccine that would induce an immune response in a subject receiving the antigen or vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

"Treating" refers to preventing a disorder, condition, or disease to which such term applies, or to preventing or reducing one or more symptoms of such disorder, condition, or disease.

"Treatment" refers to the act of "treating" as defined above.

"Triterpeniods" refers to a large and diverse class of naturally occurring organic molecules, derived from six five-carbon isoprene (2-methyl-1,3-butadiene) units, which can be assembled and modified in thousands of ways. Most are multicyclic structures which differ from one another in functional groups and in their basic carbon skeletons. These molecules can be found in all classes of living things.

"Vaccine" refers to a composition that includes an antigen, as defined herein. Administration of the vaccine to a subject results in an immune response, generally against one or more specific diseases. The amount of a vaccine that is therapeutically effective may vary depending on the particular antigen used, or the condition of the subject, and can be determined by one skilled in the art.

Adjuvant Formulations and Methods of Making

The instant application discloses several adjuvant formulations suitable for the instant invention. The common feature of these adjuvants is the presence of oil and one or more emulsifiers, wherein the oily phase comprises more than 50% of the vaccine composition encompassing the adjuvant formulations disclosed therein.

Multiple oils and combinations thereof are suitable for use of the instant invention. These oils include, without limitations, animal oils, vegetable oils, as well as non-metabolizable oils. Non-limiting examples of vegetable oils suitable in the instant invention are corn oil, peanut oil, soybean oil, coconut oil, and olive oil. Non-limiting example of animal oils is squalane. Suitable non-limiting examples of non-metabolizable oils include light mineral oil, straight chained or branched saturated oils, and the like.

In a set of embodiments, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

Typically, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80 etc), if any such emulsifiers are present. The volume of the oily phase is calculated as a sum of volumes of the oil and the emulsifier(s). Thus, for example, if the volume of the oil is 40% and the volume of the emulsifier(s) is 12% of a composition, then the oily phase would be present at 52% v/v of the composition. Similarly, if the oil is present in the amount of about 45% and the emulsifier(s) is present in the amount of about 6% of a composition, then the oily phase is present at about 51% v/v of the composition.

It also should be understood that since the adjuvants of the instant invention form only a part of the vaccines of the instant invention, oily phase is present in an amount from 50% to 95% by volume; preferably, in an amount of greater than 50% to 85%; more preferably, in an amount from 50% to 60%, and more preferably in the amount of 50-52% v/v of each of the adjuvants of the instant invention.

In a subset of embodiments, applicable to all adjuvants/vaccines of the instant invention, the volume percentage of the oil and the oil-soluble emulsifier together is at least 50%, e.g., 50% to 95% by volume; preferably, in an amount of greater than 50% to 85%; more preferably, in an amount from 50% to 60%, and more preferably in the amount of 50-52% v/v of the vaccine composition. Thus, for example and without limitations, the oil may be present in the amount of 45% and the lipid-soluble emulsifier would be present present in the amount of greater than 5% v/v. Thus, the volume percentage of the oil and the oil-soluble emulsifier together would be at least 50%.

In yet another subset, applicable to all vaccines of the invention, volume percentage of the oil is over 40%, e.g., 40% to 90% by volume; 40% to 85%; 43% to 60%, 44-50% v/v of the vaccine composition.

Emulsifiers suitable for use in the present emulsions include natural biologically compatible emulsifiers and non-natural synthetic surfactants. Biologically compatible emulsifiers include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

In additional embodiments, the emulsifiers used herein do not include lecithin, or use lecithin in an amount which is not immunologically effective.

Non-natural, synthetic emulsifiers suitable for use in the adjuvant formulations of the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate).

Generally speaking, the emulsifier(s) may be present in the vaccine composition in an amount of 0.01% to 40% by volume, preferably, 0.1% to 15%, more preferably 2% to 10%.

Additional ingredients present in the instant adjuvant formulations include cationic carriers, immunostimulatory oligonucleotides, monophospholipid A and analogs thereof (MPL-A), Polyinosinic:polycytidylic acid (poly I:C), saponins, quaternary ammoniums, sterols, glycolipids, a source of aluminum (e.g., REHYDRAGEL® or VAC 20® wet gel) and combinations thereof.

Suitable cationic carriers include, without limitations, dextran, dextran DEAE (and derivatives thereof), PEGs, guar gums, chitosan derivatives, polycellulose derivatives like hydroxyethyl cellulose (HEC) polyethylenimene, poly aminos like polylysine and the like.

Suitable immunostimulatory oligonucleotides include ODN (DNA-based), ORN (RNA-based) oligonucleotides, or chimeric ODN-ORN structures, which may have modified backbone including, without limitations, phosphorothioate modifications, halogenations, alkylation (e.g., ethyl- or methyl-modifications), and phosphodiester modifications. In some embodiments, poly inosinic-cytidylic acid or derivative thereof (poly I:C) may be used.

CpG oligonucleotides are a recently described class of pharmacotherapeutic agents that are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). These CpG motifs are not seen in eukaryotic DNA, in which CG dinucleotides are suppressed and, when present, usually methylated, but are present in bacterial DNA to which they confer immunostimulatory properties.

In selected embodiments, the adjuvants of the instant invention utilize a so-called P-class immunostimulatory oligonucleotide, more preferably, modified P-class immunostimulatory oligonucleotides, even more preferably, E-modified P-class oligonucleotides. P-class immunostimulatory oligonucleotides are CpG oligonucleotides characterized by the presence of palindromes, generally 6-20 nucleotides long. The P-Class oligonucleotides have the ability to spontaneously self-assemble into concatamers either in vitro and/or in vivo. These oligonucleotides are, in a strict sense, single-stranded, but the presence of palindromes allows for formation of concatamers or possibly stem-and-loop structures. The overall length of P-class immunostimulatory oligonucleotides is between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In one aspect of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-Methylation, modification with proynyl-dU, inosine modification, 2-bromovinyl attachment (preferably to uridine).

The P-class immunostimulatory oligonucleotides may also contain a modified internucleotide linkage including, without limitations, phosphodiesther linkages and phosphorothioate linkages. The oligonucleotides of the instant invention may be synthesized or obtained from commercial sources.

P-Class oligonucleotides and modified P-class oligonucleotides are further disclosed in published PCT application no. WO2008/068638, published on Jun. 12, 2008. Suitable non-limiting examples of modified P-class immunostiumulatory oligonucleotides are provided below (In SEQ ID NOs 1-10, "*" refers to a phosphorothioate bond and "_" refers to a phosphodiester bond). In SEQ ID NOs 11-14, all bonds are phosphodiester bonds.

```
SEQ ID NO: 1   5' T*CG*T*CG*A*CG*A*T*CG*G*C*G*CG*C*
               G*C*C*G 3'

SEQ ID NO: 2   5' T*C_G*A*C*G*T*C*G*A*T*C*G*G*C*G*
               C*G*C*G*C*C*G 3'

SEQ ID NO: 3   5' T*C*G*A*C*G*T*C*G*A*T*C*G*G*C*G*
               C*G*C*G*C*C*G*T 3'

SEQ ID NO: 4   5' JU*C_G*A*C*G*T*C*G*A*T*C*G*G*C*G
               *C*G*C*G*C*C*G 3'

SEQ ID NO: 5   5' JU*C_G*A*C*G*T*C*G*A*T*C*G*G*C*G
               *C*G*C*G*C*C*G*T 3'

SEQ ID NO: 6   5' JU*C*G*A*C*G*T*C*G*A*T*C*G*G*C*G
               *C*G*C*G*C*C*G*T 3'

SEQ ID NO: 7   5' EU*C_G*A*C*G*T*C*G*A*T*C*G*G*C*G
               *C*G*C*G*C*C*G 3'

SEQ ID NO: 8   5' JU*C_G*T*C*G*A*C*G*A*T*C*G*G*C*G
               *G*C*C*G*C*C*G*T 3'

SEQ ID NO: 9   5' JU*C*G*T*C*G*A*C*G*A*T*C*G*G*C*G
               *G*C*C*G*C*C*G*T 3'

SEQ ID NO: 10  5' T*C_G*T*C_G*A*C_G*A*T*C_G*G*C*G*
               C_G*C*G*C*C*G 3'

SEQ ID NO: 11  5'-UUGUUGUUGUUGUUGUUGUU-3'

SEQ ID NO: 12  5'-UUAUUAUUAUUAUUAUUAUU-3'

SEQ ID NO: 13  5'-AAACGCUCAGCCAAAGCAG-3'

SEQ ID NO: 14  5'-dTdCdGdTdCdGdTdTdTdTrGrUrUrGrUr
               GrUdTdTdT-3'
```

The amount of P-class immunostimulatory oligonucleotide for use in the adjuvant compositions depends upon the nature of the P-class immunostimulatory oligonucleotide used and the intended species.

Suitable analogs of MPL-A include, without limitations can be bacterial derived natural LPS altered or unaltered in structure or synthetic, Glucopyranosyl Lipid Adjuvant (GLA), pertactin, varying substitutions at 3-O-position of the reducing sugar, synthetic forms of lipid A analog with low endotoxicity.

Sterols share a common chemical core, which is a steroid ring structure[s], having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble. In view of these chemical similarities, it is thus likely that the sterols sharing this chemical core would have similar properties when used in the vaccine compositions of the instant invention. Sterols are well known in the art and can be purchased commercially. For example cholesterol is disclosed in the Merck Index, 12th Ed., p. 369. Suitable sterols include, without limitations, β-sitosterol, stigmasterol, ergosterol, ergocalciferol, and cholesterol.

Suitable saponins include triterpenoid saponins. These triterpenoids a group of surface-active glycosides of plant origin and share common chemical core composed of a hydrophilic region (usually several sugar chains) in association with a hydrophobic region of either steroid or triterpenoid structure. Because of these similarities, the saponins sharing this chemical core are likely to have similar adjuvanting properties. Triterpenoids suitable for use in the adjuvant compositions can come from many sources, either plant derived or synthetic equivalents, including but not limited to, *Quillaja saponaria*, tomatine, *ginseng* extracts, mushrooms, and an alkaloid glycoside structurally similar to steroidal saponins.

If a saponin is used, the adjuvant compositions generally contain an immunologically active saponin fraction from the bark of *Quillaja saponaria*. The saponin may be, for example, Quil A or another purified or partially purified saponin preparation, which can be obtained commercially. Thus, saponin extracts can be used as mixtures or purified individual components such as QS-7, QS-17, QS-18, and QS-21. In one embodiment the Quil A is at least 85% pure. In other embodiments, the Quil A is at least 90%, 91%, 92%, 93%, 94%, 95%, 96%, 97%, 98%, or 99% pure.

Quaternary amine compounds are ammonium based compounds with four hydrocarbon groups. In practice, hydrocarbon groups are generally limited to alkyl or aryl groups. In a set of embodiments, the quaternary amine compounds are composed of four alkyl chains, two of which are C10-C20 alkyls and the remaining two are C1-C4 alkyls. In one set of embodiments, the quaternary amine is Dimethyldioctadecylammonium bromide, chloride or pharmaceutically acceptable counterion (DDA).

Suitable glycolipids are generally those which activate the Th2 response. The glycolipids include, without limitations, those encompassed by Formula I and that are generally described in US Publication 20070196384 (Ramasamy et al).

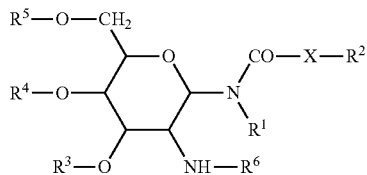

Formula I

In the structure of Formula I, $R^1$ and $R^2$ are independently hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenylalany, L-prolyl, L-seryl, L-threonyl, L-tyrosyl, L-tryptophanyl, and L-valyl or their D-isomers.

In a set of embodiments, the suitable glycolipid is N-(2-Deoxy-2-L-leucylamino-b-D-glucopyranosyl)-N-octadecyldodecanoylamide or an acetate thereof.

Aluminum is a known adjuvant or a component of adjuvant formulations and is commercially available in such forms as Reheis, Inc, Brentag alhydrogel REHYDRAGEL® or VAC 20¹ wet gel. REHYDRAGEL® is a crystalline aluminum oxyhydroxide, known mineralogically as boehmite. It is effective in vaccines when there is a need to bind negatively charged proteins. The content of $Al_2O_3$ ranges from 2% to 10% depending on grade, and its viscosity is 1000-1300 cP. Generally, it may be described as an adsorbent aluminum hydroxide gel. VAC® 20 wet gel is a white or almost white, translucent, viscous colloidal gel. In certain embodiments, the content of $Al_2O_3$ is about 2% w/v.

In other embodiments, the source of aluminum can also be prepared by precipitated aluminum hydroxide processes.

In certain set of embodiments, in addition to the oil and the optional one or more emulsifiers, the adjuvant formulations also comprise (or consist essentially, or consist) a combination of monophosphoryl lipid A (MPL-A) or an analog thereof, a sterol, and an immunostimulatory oligonucleotide. The adjuvants containing these ingredients are referred to as "TCMO". The TCMO adjuvant formulation may also optionally include poly I:C ("TCMYO") and/or a saponin. Thus, adjuvant formulations comprising, or consisting essentially of, or consisting of a combination of monophosphoryl lipid A (MPL-A) or an analog thereof, a sterol, and an immunostimulatory oligonucleotide and saponin are referred to as "QTCMO." In addition, the adjuvant formulations may also include poly I:C. Such adjuvants are referred to as "QTCMYO".

In a set of embodiments, TCMO adjuvants comprise light mineral oil in the amount of 40% to 50% v/v of the total volume of the vaccine composition. The emulsifiers include TWEEN-80 and SPAN-80, total amount 0.1% to 40% v/v of the total volume of the vaccine composition, provided that sorbitan monooleate and oil together comprise about 50.5% to 52% v/v of the composition. The immunostimulatory oligonucleotide is an ODN, preferably, a palindrome containing ODN, optionally, with a modified backbone.

In certain embodiments, one dose of TCMO contains between about 1 ug and about 400 ug of the immunostimulating oligonucleotide, between about 1 ug and about 1000 ug of the sterol, between about 0.1 ug and 500 ug MPL-A or the analog thereof.

The amounts of other compounds per dose are selected based on the subject species.

For example, in some embodiments suitable for cattle, sheep or adult swine, one dose of TCMO would contain between about 50 and 400 ug (e.g., 50-300, or 100-250 ug, or about 50 to about 100 ug for adult pigs and about 100 to about 250 ug for cattle) of the immunostimulatory oligonucleotide, between about 100 and about 1000 ug (e.g., 200-1000, 250-700 ug, or about 400-500 ug) of the sterol, such as cholesterol, and between about 5 and about 500 ug (e.g., 5-100 ug, or 5-50 ug, or 10-25 ug) of MPL-A or the analog thereof.

In some embodiments suitable for companion animals or piglets, one dose of TCMO would contain between about 5 and 100 ug (e.g., 10-80, or 20-50 ug) of the immunostimulatory oligonucleotide, between about 5 and 100 ug (e.g., 10-80, or 20-50 ug) of the sterol such as cholesterol, and between about 0.5 and about 200 ug (e.g., 1-100 ug, or 5-50 ug, or 5-20 ug) of MPL-A or the analog thereof.

In some embodiments suitable for poultry, one dose of TCMO adjuvant would contain between about 0.1 and about 5 ug (e.g., 0.5-3 ug, or 0.9-1.1 ug) of immunostimulatory oligonucleotide, between about 0.5 and about 50 ug (e.g., 1-20 ug, or 1-10 ug) of the sterol such as cholesterol, and between about 0.1 to 10 ug (e.g., 0.5-5 ug, or 1-5 ug) of MPLA or the analog thereof.). MPL-A is present in the amount of 0.1 ug/dose to 2,000 ug/dose.

In certain embodiments, TCMO adjuvants are prepared as follows:
a) Sorbitan monooleate, MPL-A and cholesterol are dissolved in light mineral oil. The resulting oil solution is sterile filtered;
b) The immunostimulatory oligonucleotide and Polyoxyethylene (20) sorbitan monooleate are dissolved in aqueous phase, thus forming the aqueous solution;
c) The aqueous solution is added to the oil solution under continuous homogenization thus forming the adjuvant formulation TCMO.

In TCMYO adjuvants, the cholesterol, oil, optional emulsifiers, MPL-A, and the immunostimulatory oligonucleotides are present as in the TCMO adjuvant formulation for the respective species. Poly I:C may be present generally in the amount between about 1 ug and about 100 ug per dose.

More specifically, poly I:C may be present in the amount of 5-100 ug per dose (e.g., 5-50 ug, or 10-30 ug) in certain embodiments suitable for cattle, adult swine, or sheep. In certain embodiments suitable for companion animals or piglets, one dose of TCMYO contains between about 1 and about 50 ug (e.g., 5-50 ug, or 10-20 ug) of poly I:C. In certain embodiments suitable for poultry vaccines, one dose of TCMYO contains between about 1 and about 10 ug (e.g., 1-5 ug, or 3-5 ug) of poly I:C.

In certain embodiments, TCMYO adjuvants are prepared similarly to the TCMO adjuvants, and the poly I:C is added to the aqueous solution.

In a set of embodiments, in QTCMO adjuvants, the cholesterol, oil, optional emulsifiers, MPL-A, and the immunostimulatory oligonucleotides are present as in the TCMO adjuvant formulation for the respective species. A saponin is preferably Quil A or a purified fraction thereof, and may be present in the amounts of between about 0.1 ug and about 1000 ug per dose.

More specifically the saponin may be present in the amount of of 0.1 to 5 ug per 50 ul of the vaccine composition (e.g., 0.5-30 ug per 50 ul of the composition, or more preferably 1-10 ug) per dose in certain embodiments suitable for poultry vaccines. In certain embodiments suitable for applications in companion animals and piglets, the saponin, e.g., Quil A or a purified fraction thereof is present in the amounts between about 10 and about 100 ug per dose (e.g., 10-50 ug or 20-50 ug per dose). In certain embodiments suitable for cattle, adult swine, or sheep, the saponin, such as Quil A or a purified fraction thereof, is present in the amount of between about 100 and about 1000 ug per dose (e.g., 200-800 ug, or 250-500 ug per dose).

In certain embodiments, QTCMO adjuvants are prepared similarly to TCMO adjuvants, and the saponin is added to the aqueous solution.

In a set of embodiments, in QTCMYO adjuvants, the saponin is present as in QTCMO adjuvant, and the rest of the ingredients are present as in TCMYO, for the respective species.

In certain embodiments, QTCMYO adjuvants are prepared similarly to TCMYO adjuvants, and the saponin is added to the aqueous solution.

In alternative embodiments, in addition to the oil and the optional emulsifier(s), the adjuvant formulations also comprise (or consist essentially of, or consist of) a combination of monophosphoryl lipid A (MPL-A) or an analog thereof and a polycationic carrier. These adjuvants are referred to as "XOM".

In a set of embodiments, in XOM adjuvants for companion animals or piglets, the polycationic carrier is present in the amount of 1-50 mg per dose (e.g., 1-25 mg per dose, or 10-25 mg per dose), and the MPL-A or the analog thereof is present in the amount of between about 1-50 ug per dose (e.g., 1-25 ug per dose, or 10-25 ug per dose).

In certain embodiments suitable for cattle, sheep and adult pigs, the polycationic carrier is present in the amount of between about 5 and about 500 mg per dose (e.g., 10-500 mg, or 10-300 mg, or 50-200 mg per dose) and the MPL-A or the analog thereof is present in the amount of between about 1 and about 100 ug per dose (e.g., 5-100 ug, or 5-50 ug, or 10-30 ug).

In certain embodiments suitable for companion animals and piglets, the polycationic carrier is present in the amount of between about 1 and about 50 mg per dose (e.g., 1-25 mg per dose, or 10-25 mg per dose), and MPL-A or the analog thereof is present in the amount of between about 0.5 and about 200 ug (e.g., 1-100 ug, or 5-50 ug, or 5-20 ug) per dose.

In certain embodiments suitable for poultry vaccines, the polycationic carrier is present in the amount of between about 0.5 and 25 mg per dose (e.g., 1-20 mg, or 1-10 mg or 5-10 mg), and the MPL-A or the analog thereof is present in the amount between about 0.5 and 10 ug per dose (e.g., 1-10 ug, or 1-5 ug, or 2-5 ug).

In certain embodiments, XOM adjuvants are prepared as follows:
a) Sorbitan monooleate, MPL-A and cholesterol are dissolved in light mineral oil. The resulting oil solution is sterile filtered;
b) Dextran DEAE and Polyoxyethylene (20) sorbitan monooleate are dissolved in aqueous phase, thus forming the aqueous solution;
c) The aqueous solution is added to the oil solution under continuous homogenization thus forming the adjuvant formulation XOM.

In additional alternative embodiments, in addition to the oil and the emulsifier(s), the adjuvant formulations also comprise (or consist essentially of, or consist of) a combination of an immunostimulatory oligonucleotide and a polycationic carrier, with a proviso that if said polycationic carrier is dextran DEAE, then the antigen is not E. coli J-5 bacterin. These adjuvants are referred to as "TXO". In certain embodiments, vaccines adjuvanted with TXO contain antigen(s) comprising pathogens affecting cattle, sheep, horses or swine. In other embodiments, the antigens are derived from said pathogens. In other embodiments, vaccines adjuvanted with TXO contain antigen(s) comprising pathogens affecting, poultry or cats, or the antigens may be derived from such pathogens. In a set of embodiments, the TXO adjuvants may also include a source of aluminum, such as $Al(OH)_3$ gel. The TXO adjuvants with aluminum are referred to as "TXO-A".

In a set of embodiments, in TXO adjuvants, the immunostimulatory oligonucleotide, preferably an ODN, preferably containing a palindromic sequence, and optionally with a modified backbone, may be present in the amount of 0.5-400 ug per dose, and the polycationic carrier may be present in the amount of 0.5-400 mg per dose. The dosages wary depending on the subject species.

For example, in certain embodiments suitable for cattle, sheep or adult swine, one dose of TXO would comprise between about 50 and 400 ug (e.g., 50-300, or 100-250 ug, or about 50 to about 100 ug for adult pigs and about 100 to about 250 ug for cattle) of the immunostimulatory oligonucleotide, and the polycationic carrier may be present in the amount of between about 5 and about 500 mg per dose (e.g., 10-500 mg, or 10-300 mg, or 50-200 mg per dose).

In certain embodiments suitable for companion animals or piglets, one dose of TXO would comprise between about 5 and 100 ug (e.g., 10-80 ug, or 20-50 ug) of the immunostimulatory oligonucleotide, while the polycationic carrier may be present in the amount of 1-50 mg per dose (e.g., 1-25 mg per dose, or 10-25 mg per dose).

In certain embodiments suitable for poultry, one dose of TXO adjuvant would between about 0.1 and about 5 ug (e.g., 0.5-3 ug, or 0.9-1.1 ug) of immunostimulatory oligonucleotide, and the polycationic carrier may be present in the amount of between 0.5 and 25 mg per dose (e.g., 1-20 mg, or 1-10 mg or 5-10 mg).

In certain embodiments, TXO adjuvants are prepared as follows:
a) Sorbitan monooleate is dissolved in light mineral oil. The resulting oil solution is sterile filtered;
b) The immunostimulatory oligonucleotide, Dextran DEAE and Polyoxyethylene (20) sorbitan monooleate are dissolved in aqueous phase, thus forming the aqueous solution; and
c) The aqueous solution is added to the oil solution under continuous homogenization thus forming the adjuvant formulation TXO.

In a set of embodiments, in TXO-A adjuvants, the immunostimulatory oligonucleotide is present as in the TXO adjuvant, the source of aluminum is present in the amount of up to 40% v/v (e.g., 35%, 30%, 25%, 20%, 15%, 10%, 5%, 1%). In a set of embodiments, the source of aluminum is present at 2%-20% v/v of the vaccine composition, more preferably between about 5% and about 17% v/v.

In certain embodiments, TXO-A adjuvants are prepared similarly to TXO adjuvants, and the source of aluminum is added to the aqueous solution.

In additional embodiments, the adjuvants of the instant invention contain the oil, optional emulsifier(s), the immunostimulatory oligonucleotide and the source of aluminum. These compounds are present in the ranges disclosed for TXO-A adjuvant, except that the polycationic carrier is absent in TOA. TOA adjuvant is prepared similarly to TXO adjuvant, except the aqueous phase contains the source of aluminum rather than DEAE dextran.

In certain embodiments, in addition to the oil and the emulsifier(s), the adjuvant formulations also comprise (or consist essentially of, or consist of) a combination of a polycationic carrier and a source of Aluminum. This adjuvant is referred to as AXO. These compounds may be present in amounts similar to those present in an adjuvant TXO-A for the respective species, and adjuvant AXO may be prepared similarly to TXO-A, but without addition of the immunostimulating oligonucleotide.

In certain other embodiments, in addition to the oil and the emulsifier(s), the adjuvant formulations also comprise (or consist essentially of, or consist of) a combination of a saponin and sterol. This adjuvant is referred to as QCO. The nature and the amounts of the ingredients of QCO are similar to the amounts of the saponin, the sterol, the oil and the emulsifier(s) in adjuvant QTCMO. QCO may be prepared by adding an aqueous solution comprising the saponin the sterol and, preferably, the water soluble emulsifier into an oily phase, comprising the oil and, preferably, the oil-soluble emulsifier under continuous homogenization.

In yet further alternative embodiments, in addition to the oil and the emulsifier(s), the adjuvant formulations also comprise (or consist essentially of, or consist of) a combination of a quaternary amine, a glycolipid, MPL-A or an analog thereof, and poly I:C. These adjuvants are referred to as "ODYRM".

In ODYRM adjuvants, the oil is generally a mixture of phospholipids such as phosphatidyl cholines. AMPHIGEN® is a suitable example of such oil, and would be present in the amount similar to the amount of oil, as described above.

In a set of embodiments, in ODYRM adjuvants, the quaternary amine, e.g., DDA, is present in the amount of between about 1 ug and about 200 ug per dose, poly I:C is present in the amount of between about 0.5 ug and 100 ug per dose, the glycolipid is present in the amount of between about 0.5 ug and about 2000 ug per dose, and the MPL-A or the analog thereof is present in the amount of between about 0.5 ug and 100 ug per dose.

More specifically, in certain embodiments suitable for administration to cattle, adult swine, or sheep, the quaternary amine may be present in the amount of between about 50 ug and about 200 ug per dose (e.g., 50-150 ug, or about 100 ug), poly I:C may be present in amounts of between about 1 ug and about 100 ug per dose (e.g., 1-50 ug or 5-50 ug), the glycolipid may be present in the amount of between about 500 ug and about 2000 ug per dose (e.g., 500-100 ug or about 1000 ug), and MPLA or the analog thereof may be present in the amount of between about 5 ug and about 100 ug per dose (e.g., 5-50 ug, or 10-50 ug).

In certain embodiments suitable for administration to companion animals and piglets, the quaternary amine may be present in the amount between about 5 and about 500 ug per dose (e.g., 10-100 ug per dose, or 20-50 ug per dose), the poly I:C may be present in the amount of between about 5 ug and about 25 ug per dose (e.g., 50-20 ug, or about 10 ug), the glycolipid may be present in the amount of between about 10 and about 100 ug per dose (e.g., 20-100 ug or 25-50 ug), and the MPL-A or the analog thereof may be present in the amount of between about 5 and about 50 ug per dose (e.g., 5-20 ug, or 10-20 ug).

In certain other embodiments, suitable for poultry vaccines, one dose would contain between about 1 ug and about 10 ug of the quaternary ammonium compound (e.g., 5-10 ug, or about 5 ug), between about 0.5 and about 10 ug of poly I:C (e.g., 1-10 ug or 1-5 ug), between about 0.5 and 10 ug of the glycolipid (e.g., 1-10 ug or 5-10 ug or 1-5 ug), and between about 0.5 ug and about 5 ug of MPL-A or the analog thereof (e.g., 0.5-5 ug or 1-5 ug).

In certain embodiments, ODYRM adjuvants are prepared as follows:
a) Sorbitan monooleate, MPL-A are dissolved in light mineral oil. The resulting oil solution is sterile filtered and dispersed in water with some surfactant, ethanol and acetic acid;
b) Polyoxyethylene (20) sorbitan monooleate, quaternary amine, e.g., DDA, and poly I:C are dissolved in aqueous phase, thus forming the aqueous solution; and
c) The aqueous solution is added to the oil solution under continuous homogenization thus forming the adjuvant formulation ODYRM.

In yet further set of embodiments, in addition to the oil and the emulsifier(s), the adjuvant formulations also comprise (or consist essentially of, or consist of) a combination of a saponin, a sterol, a quaternary amine, a polycationic carrier, with a proviso that if said polycationic carrier is dextran DEAE, then the antigen is not *E. coli* J-5 bacterin. These adjuvants are referred to as "QCDXO".

In QCDXO adjuvants, in certain embodiments, the saponin, e.g., Quil A may be present in the amounts of between about 0.1 ug and about 1000 ug per dose, the sterol, e.g., cholesterol, is present between about 1 ug and about 1000 ug per dose, the quaternary amine, e.g., DDA, is present in the amount of between about 1 ug and about 200 ug per dose, and the polycationic carrier may be present in the amount of 0.5-400 mg per dose. The dosages wary depending on the subject species.

In certain embodiments suitable for cattle, sheep, and adult swine, the saponin is present in the amount of between about 100 and about 1000 ug per dose (e.g., 200-800 ug, or 250-500 ug per dose), sterol is present in the amounts between about 100 and about 1000 ug (e.g., 200-1000, 250-700 ug, or about 400-500 ug), the quaternary amine may be present in the amount of between about 50 ug and about 200 ug per dose (e.g., 50-150 ug, or about 100 ug), and the polycationic carrier may be present in the amount of between about 5 and about 500 mg per dose (e.g., 10-500 mg, or 10-300 mg, or 50-200 mg per dose).

In certain embodiments suitable for applications in companion animals and piglets, the saponin, e.g., Quil A or a purified fraction thereof is present in the amounts between about 10 and about 100 ug per dose (e.g., 10-50 ug or 20-50 ug per dose), the sterol is present in the amounts between about 5 and 100 ug (e.g., 10-80, or 20-50 ug), the quaternary amine may be present in the amount between about 5 and about 500 ug per dose (e.g., 10-100 ug per dose, or 20-50 ug per dose), and and the polycationic carrier may be present in the amount of 1-50 mg per dose (e.g., 1-25 mg per dose, or 10-25 mg per dose.

In some embodiments suitable for poultry vaccines, the saponin may be present in the amount of of 0.1 to 5 ug per 50 ul of the vaccine composition (e.g., 0.5-30 ug per 50 ul of the composition, or more preferably 1-10 ug) per dose, the sterol may be present in the amounts between about 0.5 and about 50 ug (e.g., 1-20 ug, or 1-10 ug), the quaternary amine may be present in the amount between about 5 and about 500 ug per dose (e.g., 10-100 ug per dose, or 20-50 ug per dose) and the polycationic carrier may be present in the amount of between 0.5 and 25 mg per dose (e.g., 1-20 mg, or 1-10 mg or 5-10 mg).

In certain embodiments, QCDXO adjuvants are prepared as follows:
a) Sorbitan monooleate is dissolved in oil. The resulting oil solution is sterile filtered;
b) Polyoxyethylene (20) sorbitan monooleate, quaternary amine, e.g., DDA, the polycationic carrier, the sterol and the saponin are dissolved in aqueous phase, thus forming the aqueous solution; and
c) The aqueous solution is added to the oil solution under continuous homogenization thus forming the adjuvant formulation QCDXO.

Sometimes, it is impossible or impracticable to concentrate the antigen, particulary in scaled up commercial applications, and low-concentrations of antigen solutions have to be used. Thus in some embodiments, the vaccine compositions of the instant invention comprise the adjuvant formulations as described above, wherein the content of the oily phase in these adjuvant formulations is diluted and wherein the vaccine composition is a water-in-oil emulsion.

In practice, it is possible to create a water-in-oil emulsion wherein the oily phase is less than 50% v/v.

Briefly, first, the adjuvant formulation of the instant invention is prepared as described above. In said adjuvant formulation, the oily phase comprises over 50% v/v of the adjuvant formulation. The amounts of ingredients other than the oil and the emulsifier(s) are scaled up respectively, based on the final target concentration and desired dilution. For example, if one aims to prepare a vaccine composition where the adjuvant formulation comprises 80% v/v, the amounts of ingredients other than the oil are scaled up by the factor of 1.25 (1/0.8). The amounts of emulsifiers, if any (e.g., TWEEN® 80 and/or SPAN® 80) do not necessarily need to be scaled up, but preferably, the volume ratio between the oil and the emulsifier(s) is kept the same in the adjuvant formulation and in the final vaccine composition.

Antigen solution is then added to the adjuvant formulation.

Water-in-oil emulsion's integrity can be maintained as long as the dispersed spherical water droplets are not present in a more concentrated form than the maximum packing fraction for random packing of monodisperse droplets, i.e.: 0.64. See Tadros, *Emulsion Formation, Stability and Rheology*, 1$^{st}$ ed. 2013, Wiley-VCH GmbH & Co KGaA. As long as the total volume fraction occupied by the aqueous droplets does not exceed 0.64, i.e.: 64% v/v. Conversely this implies that the oily phase should not drop below 36% v/v.

Accordingly, in different embodiments of this aspect of the invention vaccine formulations are provided, comprising the antigen compound, and the diluted adjuvant formulation according to the previously described embodiments, wherein the oily phase comprises over 36% of the vaccine composition v/v, and wherein the vaccine composition is a water-in-oil emulsion. Without limitations, adjuvant formulations suitable for this aspect of the invention include TCMO, TCMYO, QTCMO, QTCMYO, XOM, TXO, TXO-A, TAO, AXO, QCO, ODYRM, QCDXO. The volume of the oily phase is, in different embodiments, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, or 50% v/v of the vaccine composition.

The concentration of the oily phase should be sufficiently high to create a depot effect and protect the antigen and immunomodulator(s) from a rapid degradation by the host's immune system, preferably 20% or more v/v of the vaccine composition.

Accordinghly, in another aspect, in the vaccine compositions of the instant invention, the amounts of the oily phase in the adjuvant formulations are diluted such that the vaccine formulation is an oil-in-water emulsion or a water-in-oil-in-water emulsion, with the oily phase comprising 20% or more v/v of the vaccine composition. The amounts of ingredients other than the oil and the emulsifiers are scaled up respectively, based on the final target concentration and desired dilution. For example, to prepare a vaccine composition where the adjuvant formulation comprises 33.3% v/v, the amounts of ingredients other than the oil and the emulsifier(s) are scaled up by the factor of 3 (1/0.333). The amounts of emulsifiers, if any (e.g., TWEEN® 80 and/or SPAN® 80) do not need to be scaled up, but preferably, the volume ratio between the oil and the emulsifier(s) is kept the same in the adjuvant formulation and in the final vaccine composition.

In different embodiments, the vaccine composition is an oil-in-water emulsion or an water-in-oil-in-water emulsion, wherein the oily phase comprises 21% v/v, 22% v/v, 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, or 50% v/v of the vaccine composition.

Adjuvant formulations suitable for this aspect of the invention include TCMO, TCMYO, QTCMO, QTCMYO, XOM, TXO, TXO-A, TAO, AXO, QCO, ODYRM, QCDXO, with a proviso that the oily phase in the adjuvant formulation may be below 50% v/v, but above 20% v/v of the final vaccine composition.

Antigens and Diseases

The compositions can contain one or more antigens. The antigen can be any of a wide variety of substances capable of producing a desired immune response in a subject, including, without limitations, one or more of viruses (inactivated, attenuated, and modified live), bacteria, parasites, nucleotides (including, without limitation nucleic-acid based antigens, e.g., DNA vaccines), polynucleotides, peptides, polypeptides, recombinant proteins, synthetic peptides, protein extract, cells (including tumor cells), tissues, polysaccharides, carbohydrates, fatty acids, teichioc acid, peptidoglycans, lipids, or glycolipids, individually or in any combination thereof.

The antigens used with the adjuvants of the invention also include immunogenic fragments of nucleotides, polynucleotides, peptides, polypeptides, that can be isolated from the organisms referred to herein.

Live, modified-live, and attenuated viral strains that do not cause disease in a subject have been isolated in non-virulent form or have been attenuated using methods well known in the art, including serial passage in a suitable cell line or exposure to ultraviolet light or a chemical mutagen. Inactivated or killed viral strains are those which have been inactivated by methods known to those skilled in the art, including treatment with formalin, betapropriolactone (BPL), binary ethyleneimine (BEI), sterilizing radiation, heat, or other such methods.

Two or more antigens can be combined to produce a polyvalent composition that can protect a subject against a wide variety of diseases caused by the pathogens. Currently, commercial manufacturers of vaccines, as well as end users, prefer polyvalent vaccine products. While conventional adjuvants are often limited in the variety of antigens with which they can be effectively used (either monovalently or polyvalently), the adjuvants described herein can be used effectively with a wide range of antigens, both monovalently and polyvalently. Thus, the antigens described herein can be combined in a single composition comprising the adjuvants described herein.

Some examples of bacteria which can be used as antigens with the adjuvant compositions include, but are not limited to, *Aceinetobacter calcoaceticus, Acetobacter paseruianus, Actinobacillus pleuropneumoniae, Aeromonas hydrophila, Alicyclobacillus acidocaldarius, Arhaeglobus fulgidus, Bacillus pumilus, Bacillus stearothermophillus, Bacillus subtilis, Bacillus thermocatenulatus, Bordetella bronchiseptica, Burkholderia cepacia, Burkholderia glumae, Campylobacter coli, Campylobacter fetus, Campylobacter jejuni, Campylobacter hyointestinalis, Chlamydia psittaci, Chlamydia trachomatis, Chlamydophila* spp., *Chromobacterium viscosum, Erysipelothrix rhusiopathieae, Listeria monocytogenes, Ehrlichia canis, Escherichia coli, Haemophilus influenzae, Haemophilus somnus, Helicobacter suis, Lawsonia intracellularis, Legionella pneumophilia, Moraxellsa* sp., *Mycobactrium bovis, Mycoplasma hyopneumoniae, Mycoplasma mycoides* subsp. *mycoides* LC, *Clostridium perfringens, Odoribacter denticanis, Pasteurella* (Mannheimia) *haemolytica, Pasteurella multocida, Photorhabdus luminescens, Porphyromonas gulae, Porphyromonas gingivalis, Porphyromonas salivosa, Propionibacterium acnes, Proteus vulgaris, Pseudomonas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, *Alcaliges eutrophus, Psychrobacter immobilis, Rickettsia prowazekii, Rickettsia rickettsia, Salmonella enterica* all serovars, including for example: *Salmonella enterica Typhimurium, Salmonella enterica Bongori, Salmonella enterica Dublin, Salmonella enterica Choleraseuis,* and *Salmonella enterica* Newport, *Serratia marcescens, Spirlina platensis, Staphlyoccocus aureus, Staphyloccoccus epidermidis, Staphylococcus hyicus, Streptomyces albus, Streptomyces cinnamoneus, Streptococcus uberis, Streptococcus suis, Streptomyces exfoliates, Streptomyces scabies, Sulfolobus acidocaldarius, Syechocystis* sp., *Vibrio cholerae, Borrelia burgdorferi, Treponema denticola, Treponema minutum, Treponema phagedenis, Treponema refringens, Treponema vincentii, Treponema palladium, Trueperella pyogenes* and *Leptospira* species, such as the known pathogens *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona,* and *Leptospira bratislava,* and combinations thereof.

Both inactivated viruses and attenuated live viruses may be used in the adjuvant compositions. Some examples of viruses which can be used as antigens include, but are not limited to, Avian herpesviruses, Bovine herpesviruses, Canine herpesviruses, Equine herpesviruses, Feline viral rhinotracheitis virus, Marek's disease virus, Ovine herpesviruses, Porcine herpesviruses, Porcine Epidemic Diarrhea virus (PEDv), Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus, and combinations thereof.

Examples of peptide antigens include *Bordetella bronchiseptica* p68, GnRH, IgE peptides, Fel dl, and cancer antigens, and combinations thereof. Examples of other antigens include nucleotides, carbohydrates, lipids, glycolipids, peptides, fatty acids, lipoteichoic and teichoic acid, and peptidoglycans, and combinations thereof.

Some examples of parasites which can be used as antigens with the adjuvant compositions include, but are not limited to, *Anaplasma, Fasciola hepatica* (liver fluke), Coccidia, *Eimeria* spp., *Neospora caninum, Toxoplasma gondii,* Giardia, *Dirofilaria* (heartworms), *Ancylostoma* (hookworms), *Cooperia, Haemonchus contortus* (Barber pole worm)*Ostertagia ostertagi*(stomach worm), *Dictyocaulus viviparous* (lung worms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis, Hammondia,* and *Isopsora,* and combinations thereof. Also contemplated are external parasites including, but not limited to, ticks, including *Ixodes, Rhipicephalus, Dermacentor, Amblyomma, Boophilus, Hyalomma,* and *Haemaphysalis* species, and combinations thereof.

The amount of antigen used to induce an immune response will vary considerably depending on the antigen used, the subject, and the level of response desired, and can be determined by one skilled in the art. For vaccines containing modified live viruses or attenuated viruses, a therapeutically effective amount of the antigen generally ranges from about $10^2$ Tissue Culture Infective Dose (TCID) $_{50}$ to about $10^{10}$ TCID$_{50}$, inclusive. For many such viruses, a therapeutically effective dose is generally in the range of about $10^2$ TCID$_{50}$ to about $10^8$ TCID$_{50}$, inclusive. In some embodiments, the ranges of therapeutically effective doses are about $10^3$ TCID$_{50}$ to about $10^6$ TCID$_{50}$, inclusive. In some other embodiments, the ranges of therapeutically effective doses are about $10^4$ TCID$_{50}$ to about $10^5$ TCID$_{50}$, inclusive.

For vaccines containing inactivated viruses, a therapeutically effective amount of the antigen is generally at least about 100 relative units per dose, and often in the range from about 1,000 to about 4,500 relative units per dose, inclusive. In other embodiments, the therapeutically effective amount of the antigen is in a range from about 250 to about 4,000 relative units per dose, inclusive, from about 500 to about 3,000 relative units per dose, inclusive, from about 750 to about 2,000 relative units per dose, inclusive, or from about 1,000 to about 1,500 relative units per dose, inclusive.

A therapeutically effective amount of antigen in vaccines containing inactivated viruses can also be measured in terms of Relative Potency (RP) per mL A therapeutically effective amount is often in the range from about 0.1 to about 50 RP per mL, inclusive. In other embodiments, the therapeutically effective amount of the antigen is in a range from about 0.5 to about 30 RP per mL, inclusive, from about 1 to about 25 RP per mL, inclusive, from about 2 to about 20 RP per mL, inclusive, from about 3 to about 15 RP per mL, inclusive, or from about 5 to about 10 RP per mL, inclusive.

The number of cells for a bacterial antigen administered in a vaccine ranges from about $1\times10^6$ to about $5\times10^{10}$ colony forming units (CFU) per dose, inclusive. In other embodiments, the number of cells ranges from about $1\times10^7$ to $5\times10^{10}$ CFU/dose, inclusive, or from about $1\times10^8$ to $5\times10^{10}$ CFU/dose, inclusive. In still other embodiments, the number of cells ranges from about $1\times10^2$ to $5\times10^{10}$ CFU/dose, inclusive, or from about $1\times10^4$ to $5\times10^9$ CFU/dose, inclusive, or from about $1\times10^5$ to $5\times10^9$ CFU/dose, inclusive, or from about $1\times10^6$ to $5\times10^9$ CFU/dose, inclusive, or from about $1\times10^6$ to $5\times10^8$ CFU/dose, inclusive, or from about $1\times10^7$ to $5\times10^9$ CFU/dose, inclusive.

The number of cells for a parasite antigen administered in a vaccine ranges from about $1\times10^2$ to about $1\times10^{10}$ per dose, inclusive. In other embodiments, the number of cells ranges from about $1\times10^3$ to about $1\times10^9$ per dose, inclusive, or from about $1\times10^4$ to about $1\times10^8$ per dose, inclusive, or from about $1\times10^5$ to about $1\times10^7$ per dose, inclusive, or from about $1\times10^6$ to about $1\times10^8$ per dose, inclusive.

It is well known in the art that with conventional adjuvants, a substantially greater amount of inactivated viruses than modified live or attenuated viruses is needed to stimulate a comparable level of serological response. However, it has been surprisingly found that with the adjuvant compositions described herein, approximately the same amounts of inactivated virus and modified live virus stimulate similar levels of serological response. In addition, smaller amounts of modified live, attenuated, and inactivated virus are needed with the adjuvants described herein when compared with conventional adjuvants to achieve the same level of serological response. These unexpected findings demonstrate conservation of resources and reduction of cost during preparation of immunogenic and vaccine compositions. For vaccines with wide utility, the manufacture of millions of doses per year is required, so these savings can be substantial.

Administration of the Compositions

Dose sizes of the compositions typically range from about 1 mL to about 5 mL, inclusive, depending on the subject and the antigen. For example, for a canine or feline, a dose of about 1 mL is typically used, while in cattle a dose of about 2-5 mL is typically used. However, these adjuvants also can be formulated in microdoses, wherein doses of about 100 .mu.L can be used.

The routes of administration for the adjuvant compositions include parenteral, oral, oronasal, intranasal, intratracheal, topical, subcutaneous, intramuscular, transcutaneous, intradermal, intraperitoneal, intraocular, intravenous administration and in ova. Any suitable device may be used to administer the compositions, including syringes, droppers, needleless injection devices, patches, and the like. The route and device selected for use will depend on the composition of the adjuvant, the antigen, and the subject, and such are well known to the skilled artisan.

Use of the Compositions

One of the requirements for any vaccine adjuvant preparation for commercial use is to establish the stability of the adjuvant solution for long periods of storage. Provided herein are adjuvant formulations that are easy to manufacture and stable for at least 18 months. In one embodiment, the formulations are stable for about 18 months. In another embodiment, the formulations are stable for between about 18 to about 24 months. In another embodiment the formulations are stable for about 24 months. Accelerated testing procedures also indicate that the formulations described herein are stable.

An advantageous feature of the present adjuvant compositions is that they can be safely and effectively administered to a wide range of subjects. In the art, it is expected that combinations of adjuvants will demonstrate more reactogenicity than the individual components. However, the compositions described herein show decreased reactogenicity when compared to compositions in which any one or two of the components are used, while the adjuvant effect is maintained. It has also been surprisingly found that the adjuvant compositions described herein demonstrate safety improvements when compared with other adjuvant compositions.

The adjuvant compositions described herein are useful for inducing a desired immune response in a subject. They are efficacious in multiple species. A suitable subject is any animal for which the administration of an adjuvant composition is desired. It includes mammals and non-mammals, including primates, livestock, companion animals, laboratory test animals, captive wild animals, aves (including in ova), reptiles, and fish. Thus, this term includes but is not limited to monkeys, humans, swine; cattle, sheep, goats, equines, mice, rats, guinea pigs, hamsters, rabbits, felines, canines, chickens, turkeys, ducks, other poultry, frogs, and lizards.

The adjuvants described herein can be used to show serological differentiation between infected and vaccinated animals. Thus, they can be used in a marker vaccine in which the antigen in the vaccine elicits in the vaccinated animals a different antibody pattern from that of the wild-type virus. A marker vaccine is generally used in conjunction with a companion diagnostic test which measures the difference in antibody patterns and demonstrates which animals have been vaccinated and which animals are infected with the wild-type virus. Such technology is useful in the control and eradication of viruses from a subject population.

The present invention also provides novel vaccine compositions useful in protecting against infection and disease caused by Nipah virus and/or Hendra virus, using antigen provided from Hendra virus G protein (and fragments, dimers, multimers, and modified forms thereof), all of which are adjuvanted as described herein. In certain embodiments, the adjuvant is selected from the group consisting of TXO, TAO, and TXO-A. Such vaccines are useful in preventing infection and disease in, for example, horses, dogs, swine and humans. In a most preferred embodiment, both swine and dogs are protected from both Hendra and Nipah virus.

Recurrent outbreaks of NiV resulting in significant numbers of human fatalities have recently been problematic, see, for example, Butler, Nature, vol. 429, at page 7 (2000); and Gurley et al., Emerging Infectious Diseases, vol. 13(7), pp. 1031-1037 (2007). Case studies have linked disease in humans to zoonotic transmission from swine, see Parashar et al., J. Infect. Dis. vol 181 pp. 1755-1759 (2000). Hendra virus has also clearly been linked to deaths in humans, via transmission from horses. There is presently one licensed vaccine for the prevention of infection or disease caused by Hendra virus (Equivac® HeV; Zoetis) approved for use in horses, although no licensed vaccine exists for preventing Nipah virus infection. There remains a need for Nipah virus or Hendra virus vaccines that can be clinically effective.

Paramyxoviruses such as Hendra virus and Nipah virus possess two major membrane-anchored glycoproteins in the envelope of the viral particle. One glycoprotein is required for virion attachment to receptors on host cells and is designated as either hemagglutinin-neuraminidase protein (HN) or hemagglutinin protein (H), and the other is glycoprotein (G), which has neither hemagglutination nor neuraminidase activities. The attachment glycoproteins are type II membrane proteins, where the molecule's amino (N) terminus is oriented toward the cytoplasm and the protein's carboxy (C) terminus is extracellular. The other major glycoprotein is the fusion (F) glycoprotein, which is a trimeric class I fusogenic envelope glycoprotein containing two heptad repeat (HR) regions and a hydrophobic fusion peptide. Hendra virus and Nipah virus infect cells through a pH-independent membrane fusion process into receptive host cells, through the concerted action of their attachment G glycoprotein and F glycoprotein following receptor binding.

That Hendra virus G glycoprotein could potentially cross protect against infection and disease by Nipah virus is suggested by K. Bossart et al., Journal of Virology, vol. 79, pp. 6690-6702 (2005), and B. Mungall et al., Journal of Virology, vol. 80, pp. 12293-12302 (2006). However, prior work does not provide vaccine compositions that are actually clinically effective in this regard, for any mammalian species. Accordingly, the present invention encompasses an immunogenic composition comprising Hendra virus G protein, an adjuvant as described according to the practice of the present invention, and one or more excipients, in an amount effective to elicit clinically effective protection against Hendra and/or Nipah virus.

In regard of Hendra virus G glycoprotein polypeptides that are useful in the practice of the present invention, and the recombinant expression thereof, reference is made to the entire disclosure of published international patent applications WO 2012/158643 and WO2006/085979 where such information is clearly set forth. Preferred examples of specific Hendra virus G protein polypeptides useful herein are disclosed in WO 2012/158643, and include, for example: full length G protein (SEQ ID NO:2 thereof); a soluble fragment thereof (encoding amino acids 73-604 of SEQ ID NO:2 of WO 2012/158643); and an additional fragment disclosed therein having an Ig(kappa) leader sequence (SEQ ID NO 16 of WO 2012/158643). Generally, the soluble forms of the Hendra virus G glycoprotein comprises all or part of the ectodomain, and are produced by deleting all or part of the transmembrane domain of the G glycoprotein, and all or part of the cytoplasmic tail. Preferably, the encoding gene sequence is codon optimized for expression.

In some embodiments, the Hendra G glycoprotein may be in dimeric and/or tetrameric form. Such dimers depend upon the formation of disulfide bonds formed between cysteine residues in the G glycoprotein. Such disulfide bonds can correspond to those formed in the native G glycoprotein, or different disulfide bonds can be formed resulting in different dimeric and/or tetrameric forms of the G glycoprotein which enhance antigenicity. Additionally, non-dimerized and tetramerized forms are also useful according to the practice of the present invention, again taking into account that G glycoprotein provides numerous conformation-dependent epitopes (i.e. that arise from a tertiary three dimensional structure) and that preservation of numerous of such natural epitopes is accordingly highly preferred so as to impart a neutralizing antibody response.

Generally speaking, construction of expression vectors for the Hendra G proteins can be as described in Example 1 of WO 2012/158643, with resultant protein expression from CHO cells being as described in Example 2 thereof, or alternatively, using a Vaccinia system (see Example 3 thereof) or 293 cells (see Example 4 thereof). In a specific preferred example, the soluble G protein is provided as amino acids 73-604 of the native Hendra virus G glycoprotein (see SEQ ID NO: 2 in WO 2012/158643). Dimerization thereof occurs spontaneously, concomitant with expression from CHO cells, and resultant G protein is approximately 50% dimer and 50% tetramer, with little remaining monomer. Expression in 293F cells leads to about 70% dimer. The resultant protein fractions are mixed with adjuvants as described throughout the present specification. As described in WO2012/158643, preferred doses of antigen for large animals are in the range of 50-200 micrograms per dose, with 100 micrograms being a most preferred dose. For smaller animals, such as dogs, lesser amounts are needed, such as 25-50 micrograms, as will be appreciated by those skilled in the art.

In addition, adjuvants according to any of the embodiments described above may be used for generation of diagnostic or therapeutic antibodies. In this aspect of the invention, a source animal is immunized with a formulation containing the adjuvant compositions of the instant invention and an antigen. The choice of the antigen is determined by the person who needs to obtain said therapeutic or diagnostic antibodies and includes, without limitations, viruses, bacteria, viral particles, extracts, recombinant antigens, cell wall structures and the like. Antigens may also include venoms for preparation of medicines against snake bites.

The antigens suitable for this aspect of the invention may be of a feline, a canine, an equine, a porcine, a bovine, an ovine or avian origin. In certain embodiments, the antigen may be selected from FeLVgp70, Bovine Parainfluenza-3 BPI-3 (HN protein), *Histophilus somni* p31, *Bordetella* FHA, Parapox, BVDV1 gp53, BVDV2 gp53, Clostridia toxins, Canine Circovirus, *Brachyspira hyodysenteriae* (swine species) Antigens; whole cell inactivated and Pepsin Digest inactivated.

A certain time after immunization, a source of antibodies is extracted from the source animal (e.g., mice, rats, hamsters, swine, guinea pigs, rabbits, goats, sheep, poultry, cattle, horses). In certain other embodiments, the source animal is a cat or a dog. The source of antibodies ultimately depends on whether monoclonal or polyclonal antibodies are needed. For polyclonal antibodies, one may consider using serum or milk. For monoclonal antibodies, spleen cells are suitable source. Such antibodies may be used for diagnostic, research, or therapeutic purposes, including, without limitations, anti-venom, transplant rejection medications, Serum Neutralization assays, ELISAs, EUSPOTs, Western blots, Cell-based assays, potency assays, and Immunohistochemistry. The invention provides monoclonal and polyclonal antibodies extracted from the source animal for use in diagnostic and therapeutic applications, including without limitatins, anti-venom, transplant rejection medications, Serum Neutralization assays, ELISAs, ELISPOTs, Western blots, Cell-based assays, potency assays, and Immunohistochemistry.

In certain embodiments, immunizations with the compositions of the instant invention would elicit sufficiently high serology titers to the desired antigen (over 1000, or more preferably, over 5000, or more preferably, over 10000, or more preferably, over 50000, or more preferably, over 100000, or more preferably, over 250000, or more preferably, over 500000, or more preferably, over 1000000) in at least one animal (preferably at least 2 animals, or at least three animals, or in 50% of treated animals, or in at least 75% of treated animals, or, most preferably, in every animal treated) thus resulting in sufficient amount of antibodies for diagnostic or research applications.

Typically, antibodies of the Immunoglobulin G (IgG) isotype are used in these applications, although antibodies of other isotypes, e.g., Immunoglobulin M (IgM), are also employed. The antibody source ultimately depends on whether a polyclonal or a monoclonal antibody is desired. For polyclonal antibodies, one may use serum or milk as the source of the antibodies. For monoclonal antibodies, splenocytes is the proper antibody source. Further purification of the antibodies, if needed, or preparation of monoclonal antibodies have been described in literature extensively and one of ordinary skill in the art would have no undue difficulties in performing these procedures. Further, antibodies may be adapted to the target species, if needed (e.g., canonized or felinized). Again, the techniques for doing so are well known in the art and do not need to be described in this application.

Applications of Antibodies

The antibodies would be suitable as reagents for Serum Neutralization assays, ELISAs, ELISPOTs, Western blots, Cell-based assays, potency assays, and Immunohistochemistry. These techniques have been known in the field.

The antibodies of the instant invention may also be used as therapeutic agents, e.g., in transplant rejection, e.g., for generation of antithymocyte globulin (ATG) agents. Currently, two such agents are on the market: Atgam® and Thymoglobulin®. Methods of making anti-thymocyte globulins in general have been described in US20040023340.

It may also be used for the preparation of anti-venom medicines. In these embodiments, snake venom components would be used as antigens. The venoms and components thereof are also well known in the art.

Animals of many species may be used as source animals, including, without limitations, poultry, mice, rats, hamsters, guinea pigs, rabbits, dogs, cats, sheep, goats, swine, cattle, and equine species. The choice of the source animal depends on the task at hand and judgment of the person of ordinary skill in the art.

Specific non-limiting embodiments are as follows:

In a first embodiment, the invention provides an adjuvant formulation comprising an oily phase and an aqueous phase, wherein the oily phase comprises at least 50% of the formulation v/v, wherein said formulation comprises at least one of monophosphoryl lipid A (MPL-A) or an analog thereof and an immunostimulatory oligonucleotide, with provisos that:
  a) if said immunostimulatory oligonucleotide is absent, then the formulation comprises:
    i. a poly I:C, a glycolipid, and, optionally, a quaternary amine; or
    ii. a polycationic carrier;
  b) if said monophosphoryl lipid A (MPL-A) or the analog thereof is absent, then the formulation comprises a source of aluminum.

In the second embodiment, the invention provides the adjuvant formulation of the first embodiment, wherein the immunostimulatory oligonucleotide, if present, is a CpG or an oligoribonucleotide; the polycationic carrier, if present, is selected from the group consisting of dextran, dextran DEAE (and derivatives thereof), PEGs, guar gums, chitosan derivatives, polycellulose derivatives like hydroxyethyl cellulose (HEC) polyethylenimene, poly aminos; and the quaternary amine, if present, is selected from the group consisting of DDA and avridine.

In the third embodiment, the invention provides the adjuvant formulation according to the first or the second embodiment, wherein the immunostimulatory oligonucleotide if present, is the CpG, the polycationic carrier, if present, is dextran DEAE, and the quaternary amine, if present, is DDA.

In the fourth embodiment, the invention provides the adjuvant formulation according to any one of first through third embodiments, wherein the glycolipid, if present, comprises a compound of formula I

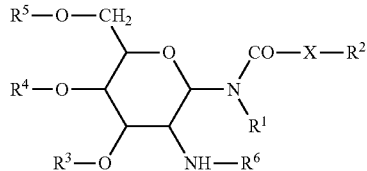

Formula I wherein, $R^1$ and $R^2$ are independently hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

In the fifth embodiment, the invention provides the adjuvant formulation of the fourth embodiment, wherein the glycolipid is N-(2-Deoxy-2-L-leucylamino-b-D-glucopyranosyl)-N-octadecyldodecanoylamide or a salt thereof.

In the sixth embodiment, the invention provides the adjuvant formulation of the fifth embodiment, wherein the salt is an acetate.

In the seventh embodiment, the invention provides the adjuvant formulation of any one of fists thought fourth embodiments, comprising both said monophosphoryl lipid A (MPL-A) or the analog thereof, and further comprising at least one of a sterol and a poly I:C.

In the eighth embodiment, the invention provides the adjuvant formulation according to the seventh embodiment, comprising the sterol and further comprising a saponin.

In the ninth embodiment, the invention provides the adjuvant formulation of any one of the senventh and the eighth embodiments, wherein the saponin, if present, is a triterpenoid saponin, and the sterol, if present, is selected from the group consisting of ergosterol, lanosterol and cholesterol.

In the tenth embodiment, the invention provides the adjuvant formulation according to the ninth embodiment, wherein the saponin, if present, is Quil A, and the sterol, if present, is cholesterol.

In the eleventh embodiment, the invention provides the adjuvant formulation according to the seventh embodiment, comprising the poly I:C, and further comprising at least one of the quaternary amine and the glycolipid.

In the twelfth embodiment, the invention provides the adjuvant formulation of any one of the first-eleventh embodiments, comprising the MPL-A or the analog thereof in the amount of 0.5-100 ug per dose.

In the thirteenth embodiment, the invention provides the adjuvant formulation according to the twelfth embodiment, wherein the MPL-A or the analog thereof is present in the amount of 5-50 ug per dose, or 5-20 ug per dose, or 1-5 ug per dose.

In the fourteenth embodiment, the invention provides the adjuvant formulation of any one of the first-thirteenth embodiments, comprising the immunostimulatory oligonucleotide in the amount of 0.5 to 400 ug per dose.

In the fifteenth embodiment, the invention provides the adjuvant formulation of the fourteenth embodiment, wherein the immunostimulatory oligonucleotide is present in the amount of about 100 to about 250 ug per dose or about 20 to about 50 ug per dose, or about 1 ug per dose.

In the sixteenth embodiment, the invention provides the adjuvant formulation of any one of first through fifteenth embodiments, comprising the polycationic carrier in the amount of between about 0.5 and about 400 mg per dose.

In the seventeenth embodiment, the invention provides the adjuvant formulation of the sixteenth embodiment, wherein said polycationic carrier is present in the amount of 50-300 mg per dose or 1-25 mg per dose, or 1-10 mg per dose.

In the eighteenth embodiment, the invention provides the adjuvant formulation of any one of the first-seventeenth embodiment, comprising the glycolipid in the amount of between about 0.5 and about 2000 ug per dose.

In the nineteenth embodiment, the invention provides the adjuvant formulation of the eighteenth embodiment, wherein the glycolipid is present in the amount of about 1000 ug per dose, or 25-50 ug per dose, or 1-10 ug per dose.

In the twentieth embodiment, the invention provides the adjuvant formulation of any one of the first-nineteenth embodiments, comprising the sterol in the amount of between about 0.1 and about 1000 ug per dose.

In the twenty-first embodiment, the invention provides the adjuvant formulation according to the twentieth embodiment, wherein the sterol is present in the amount of 250-500 ug per dose, or 20-50 ug per dose, or 1-10 ug per dose.

In the twenty-second embodiment, the invention provides the adjuvant formulation of any one of first through twenty-first embodiment, comprising the saponin in the amount of between 0.1 and 1000 ug per dose.

In the twenty-third embodiment, the invention provides the adjuvant formulation of the twenty-second embodiment, wherein the saponin is present in the amount of 250-500 ug per dose, or 20-50 ug per dose, or 1-10 ug per dose.

In the twenty-fourth embodiment, the invention provides the adjuvant formulation of any one of first through twenty-third embodiment, comprising the poly I:C is in the amount of between about 0.5 and about 100 ug per dose.

In the twenty fifth embodiment, the invention provides the adjuvant formulation of the twenty-fourth embodiment, wherein the poly I:C is present in the amount of 5-50 ug per dose, or 5-20 ug per dose, or 1-5 ug per dose.

In the twenty-sixth embodiment, the invention provides the adjuvant formulation of any one of first through twenty-fifth embodiment, comprising the source of aluminum, which is an aluminum hydroxide gel.

In the twenty-seventh embodiment, the invention provides the adjuvant formulation of twenty-sixth embodiment, wherein said source of aluminum is present in the amount of 5%-20% v/v of the formulation.

In the twenty-eighth embodiment, the invention provides the adjuvant formulation of the twenty-seventh embodiment, wherein said source of aluminum is present in the amount of 10% v/v of the formulation.

In the twenty-ninth embodiment, the invention provides the adjuvant formulation of any one of the first through twenty-eighth embodiment, wherein the oily phase comprises an oil and an oil-soluble emulsifier.

In the thirtieth embodiment, the invention provides the adjuvant formulation of any one of the first through the twenty-ninth embodiment, wherein said oily phase is present in the amount of up to 85% v/v.

In the thirty-first embodiment, the invention provides the adjuvant formulation according to the thirtieth embodiment, wherein said oily phase is present in the amount of 51%.

In the thirty-second embodiment, the invention provides the adjuvant formulation of any one of the twenty-ninth through the thirty-first embodiments, wherein the oil comprises 40-84% v/v of the formulation, and the oil-soluble emulsifier comprises 1-11% v/v of the formulation.

In the thirty-third embodiment, the invention provides the adjuvant formulation of the thirty-second embodiment, wherein the oil comprises 45% v/v of the formulation, and the oil-soluble emulsifier comprises 6% v/v of the formulation.

In the thirty-fourth embodiment, the invention provides the adjuvant formulation according to any one of the first through thirty-third embodiment, wherein said oil is selected from the group consisting of squalane, vegetable oils, triglycerides, non-metabolizable straight-chain alkane oils, and any combination thereof.

In the thirty-fifth embodiment, the invention provides the adjuvant formulation according to the thirty-fourth embodiment, wherein said oil is a light mineral oil.

In the thirty-sixth embodiment, the invention provides a vaccine composition comprising an effective amount of an antigen and the adjuvant formulation according to any one of the first through the thirty-fifth embodiment, wherein the oily phase of the composition is at least 50% v/v.

In the thirty-seventh embodiment, the invention provides a vaccine composition comprising an effective amount of an antigen and an adjuvant formulation comprising an oily phase and an aqueous phase, wherein the oily phase comprises at least 50% of the formulation v/v, a polycationic carrier, and a. a combination of a saponin and a sterol, and optionally, a quaternary amine; with provisos that if said adjuvant formulation consists essentially of DEAE dextran, Quil A, Cholesterol, and DDA, the antigen is not *E. coli* J-5 bacterin; or b. an immunostimulatory oligonucleotide, with a proviso that if said adjuvant formulation consists essentially of DEAE dextran and the immunostimulatory oligonucleotide, the antigen comprises a pathogen affecting cattle, sheep, horses, or swine or is derived from said pathogen, and is not *E. coli* J-5 bacterin.

In the thirty-eighth embodiment, the invention provides the vaccine composition according to the thirty-seventh embodiment, wherein the saponin, if present, is a triterpenoid saponin, the sterol, if present, is selected from the group consisting of ergosterol, lanosterol and cholesterol, the polycationic carrier, if present, is selected from the group consisting of dextran, dextran DEAE (and derivatives thereof), PEGs, guar gums, chitosan derivatives, polycellulose derivatives like hydroxyethyl cellulose (HEC) polyethylenimene, poly aminos, and the quaternary amine, if present, is selected from the group consisting of DDA and avridcine.

In the thirty-ninth embodiment, the invention provides the vaccine composition according to the thirty-eighth embodiment, wherein the saponin is Quil A, the sterol is cholesterol, the polycationic carrier is dextran DEAE, and the quaternary amine is DDA.

In the fortieth embodiment, the invention provides the vaccine composition of any one of thirty-seventh though thirty-ninth embodiments, wherein the immunostimulatory oligonucleotide is a CpG.

In the forty-first embodiment, the invention provides the vaccine composition of any one of thirty-seventh through fourtieth embodiment, wherein said polycationic carrier is present in the amount of between about 0.5 and about 400 mg per dose.

In the forty-second embodiment, the invention provides the vaccine composition of the forty-first embodiment, wherein said polycationic carrier is present in the amount of 50-300 mg per dose or 1-25 mg per dose, or 1-10 mg per dose.

In the forty-third embodiment, the invention provides the vaccine composition of any one of thirty-seventh through forty-second embodiments, comprising the saponin in the amount of between about 0.1 and about 1000 ug per dose.

In the forty-fourth embodiment, the invention provides the vaccine composition of the forty-third embodiment, wherein the saponin is present in the amount of 250-500 ug per dose, or 20-50 ug per dose, or 1-10 ug per dose.

In the forty-fifth embodiment, the invention provides the vaccine composition of any one of thirty-seventh through forty-fourth embodiments, comprising the sterol in the amount of between about 0.1 and about 1000 ug per dose.

In the forty-sixth embodiment, the invention provides the vaccine composition of the forty-fifth embodiment, wherein the sterol is present in the amount of 250-500 ug per dose, or 20-50 ug per dose, or 1-10 ug per dose.

In the forty-seventh embodiment, the invention provides the vaccine composition of any one of thirty-seventh through forty-sixth embodiments, comprising the quaternary amine in the amount of between about 1 and about 200 ug per dose.

In the forty-eighth embodiment, the invention provides the vaccine composition of forty-seventh embodiment, wherein the quaternary amine is present in the amount of about 100 ug per dose or between about 10 and about 100 ug per dose or about 5 ug per dose.

In the forty-ninth embodiment, the invention provides the vaccine composition of any one of of thirty-seventh through forty-eighth embodiments, comprising the immunostimulatory oligonucleotide in the amount of between about 0.5 ug and about 400 ug per dose.

In the fiftieth embodiment, the invention provides the vaccine composition of the forty-ninth embodiment, wherein the immunostimulatory oligonucleotide is present in the amount of 100-250 ug per dose, or 20-50 ug per dose or about 1 ug per dose.

In the fifty-first embodiment, the invention provides the vaccine composition of any one of thirty-seventh through fiftieth embodiments, wherein the oily phase comprises an oil and an oil-soluble emulsifier.

In the fifty-second embodiment, the invention provides the vaccine composition of any one of thirty-seventh through fifty-first embodiments, wherein said oily phase is present in the amount of up to 85% v/v.

In the fifty-third embodiment, the invention provides the vaccine composition of the fifty-second embodiment, wherein said oily phase is present in the amount of 51% v/v.

In the fifty-fourth embodiment, the invention provides the vaccine composition of any one of fifty-first through fifty-third embodiments, wherein the oil comprises 40-84% v/v of the vaccine composition, and the oil-soluble emulsifier comprises 1-11% v/v of the vaccine composition.

In the fifty-fifth embodiment, the invention provides the vaccine composition of the fifty-third embodiment, wherein the oil comprises 45% v/v of the formulation, and the oil-soluble emulsifier comprises 6% v/v of the formulation.

In the fifty-sixth embodiment, the invention provides a vaccine composition comprising an *Eimeria maxima* or *Clostridium perfringens* antigen and an adjuvant formulation which comprises:

a) an oily phase, said oily phase being present in the amount of at least 50% v/v of the composition; a polycationic carrier, and optionally, an immunostimulatory oligonucleotide; or b) an oily phase, said oily phase being present in the amount of at least 50% v/v of the composition; an immunostimulatory oligonucleotide, a sterol, and monophosphoryl lipid A (MPL-A) or an analog thereof.

In the fifty-seventh embodiment, the invention provides the vaccine composition of the fifty-sixth embodiment, comprising antigens against *Eimeria maxima* and *Clostridium perfringens*.

In the fifty-eighth embodiment, the invention provides the vaccine composition of claim the fifty-sixth embodiment or the fifty-seventh embodiment, wherein said polycationic carrier is DEAE-Dextran.

In the fifty-ninth embodiment, the invention provides a use of the vaccine composition according to claims fifty-sixth through fifty-eighth embodiment for treatment or prevention of infections caused by *Eimeria maxima* or *Clostridium perfringens* in poultry.

In the sixtieth embodiment, the invention provides a vaccine composition comprising a *Neospora* antigen and an adjuvant formulation comprising an oily phase, said oily phase being present in the amount of at least 50% v/v of the composition; and a) monophosphoryl lipid A (MPL-A) or an analog thereof; or b) a combination of an immunostimulatory oligonucleotide and a polycationic carrier.

In the sixty-first embodiment, the invention provides the vaccine composition of the sixtieth embodiment, comprising the combination of the immunostimulatory oligonucleotide and dextran DEAE.

In the sixty-second embodiment, the invention provides the vaccine composition of the sixtieth embodiment, comprising monophosphoryl lipid A (MPL-A) or the analog thereof, and further comprising the immunostimulatory oligonucleotide.

In the sixty-third embodiment, the invention provides the vaccine of the sixty-second embodiment, further comprising a sterol.

In the sixty-fourth embodiment, the invention provides the vaccine of the sixty-third embodiment, wherein the sterol is cholesterol.

In the sixty-fifth embodiment, the invention provides the vaccine according to any one of sixtieth though sixty-fourth embodiment, wherein the *Neospora* antigen is a *Neospora caninum* antigen.

In the sixty-sixth embodiment, the invention provides use of the vaccine according to any one of sixtieth though sixty-fifth embodiment for treatment or prevention of an infection caused by *Neospora*.

In the sixty-seventh embodiment, the invention provides a vaccine composition comprising a *Chlamydophila abortis* antigen and an adjuvant formulation comprising an oily phase, said oily phase being present in the amount of at least 50% v/v of the composition; a sterol; an immunostimulatory oligonucleotide; monophosphoryl lipid A (MPL-A) or an analog thereof; and poly I:C.

In the sixty-eighth embodiment, the invention provides use of the vaccine according to the sixty-seventh embodiment for treatment or prevention of an abortion caused by *C. abortis* in ewes.

In the sixty ninth embodiment, the invention provides a vaccine composition comprising myostatin and an adjuvant formulation, said adjuvant formulation comprising an oily phase, said oily phase being present in the amount of at least 50% v/v of the composition, an immunostimulatory oligonucleotide and either:
 a) a polycationic carrier; or
 b) MPL-A or an analog thereof.

In the seventieth embodiment, the invention provides the vaccine composition of the sixty-ninth embodiment comprising MPL-A or the analog thereof, wherein said formulation contains less than 0.5 ug of a sterol per 50 ul of said composition.

In the seventy-first embodiment, the invention provides the vaccine composition of the seventieth embodiment, which contains no sterol.

In the seventy-second embodiment, the invention provides the vaccine composition of the seventieth embodiment, wherein the sterol is cholesterol.

In the seventy-third embodiment, the invention provides a use of the vaccine according to any one of embodiments 69 through 72 for lowering an amount of myostatin in an animal.

In the seventy-fourth embodiment, the invention provides the use according to the seventy-third embodiment, wherein said animal is a poultry animal.

In the seventy-fifth embodiment, the invention provides a vaccine composition comprising an *Trueperella pyogenes* antigen and an adjuvant formulation, wherein the adjuvant formulation comprises an oily phase, said oily phase being present in the amount of at least 50% v/v of the composition; an immunostimulatory oligonucleotide and a polycationic carrier.

In the seventy-sixth embodiment, the invention provides the vaccine composition of the seventy-fifth embodiment, wherein the *Trueperella pyogenes* antigen is pyolysin.

In the seventy-seventh embodiment, the invention provides the use of the vaccine composition of the seventy-fourth or the seventy-fifth embodiment for treatment or prevention of an infection caused by *Trueperella pyogenes*.

In the seventy-eighth embodiment, the invention provides a vaccine composition comprising an *E. coli* antigen, a BRV antigen or a BCV antigen, and an adjuvant formulation, wherein said adjuvant formulation comprises an oily phase present in the amount of at least 50% v/v of said vaccine composition, an immunostimulatory oligonucleotide and at least one of a polycationic carrier and a source of aluminum.

In the seventy-ninth embodiment, the invention provides the vaccine composition of the seventy-eighth embodiment, comprising *E. coli* antigen, a BRV antigen and a BCV antigen.

In the eightieth embodiment, the invention provides the vaccine composition of the seventy-eighth or seventy-ninth embodiment wherein
 a. *E. coli* antigen, if present, is selected from the group consisting of *E. coli* K99, *E. coli* F41 and a combination thereof;
 b. BRV antigen, if present, is selected from the group consisting of BRV G6, BRV G10 and a combination thereof.

In the eighty-first embodiment, the invention provides the vaccine composition according to any one of seventy-eighth through eightieth embodiment, wherein the polycationic carrier, if present, is dextran DEAE, and the immunostimulatory oligonucleotide is a CpG.

In the eighty-second embodiment, the invention provides the vaccine composition according to any one of seventy-eighth through eighty-first embodiment, comprising the source of aluminum, which is an aluminum hydroxide gel.

In the eighty-third embodiment, the invention provides the vaccine composition of the eighty-second embodiment, wherein said source of aluminum is present in the amount of 5%-20% v/v.

In the eighty-fourth embodiment, the invention provides the vaccine composition of the the eighty-third embodiment, wherein said source of aluminum is present in the amount of 10%-17% v/v.

In the eighty-fifth embodiment, the invention provides a use of the vaccine composition according to any one of the seventy-eighth through eighty-fourth embodiment for treatment or prevention of enteritis caused by *E. coli*, BCV or BRV in a bovine animal.

In the eighty-sixth embodiment, the invention provides the use according to the ninety-first embodiment, wherein said vaccine causes at least a six-month-long immunity to said antigen(s).

In the eighty-seventh embodiment, the invention provides a vaccine composition comprising a *Rhipicephalus microplus* antigen and an adjuvant, said adjuvant being selected from the group consisting of:
 a) an aqueous adjuvant comprising an immunostimulatory oligonucleotide, a saponin, a sterol, a quaternary amine, a polyacrylic polymer, and a glycolipid; and
 b) an oil-based adjuvant, comprising an oily phase present in the amount of at least 50% v/v of the vaccine composition and comprising an immunostimulatory oligonucleotide and a polycationic carrier.

In the eighty-eigthth embodiment, the invention provides the vaccine composition of eighty-seventh embodiment, wherein the saponin is Quil A, the sterol is cholesterol, the quaternary amine is DDA, the glycolipid is N-(2-Deoxy-2-L-leucylamino-b-D-glucopyranosyl)-N-octadecyldodecanoylamide or a salt thereof, and the immunostimulatory oligonucleotide is a CpG.

In the eighty-ninth embodiment, the invention provides the vaccine composition of the eighty-seventh embodiment, wherein the polycationic carrier is dextran DEAE and the immunostimulatory oligonucleotide is a CpG.

In the ninetieth embodiment, the invention provides the vaccine composition of any one of the eighty-seventh to eighty-ninth embodiment, wherein the *Rhipicephalus microplus* antigen is Bm86 protein.

In the ninety-first embodiment, the invention provides a use of the vaccine composition according to any one of the eighty-seventh to ninetieth embodiment for treatment or prevention of an infection caused by *Rhipicephalus microplus*.

In the ninety-second embodiment, the invention provides a vaccine composition comprising a Foot-and-Mouth Disease (FMD) antigen and an adjuvant formulation, said adjuvant formulation comprising an oily phase present in the amount of at least 36% v/v of said vaccine composition, an immunostimulatory oligonucleotide and a polycationic carrier, wherein said vaccine composition is a water-in-oil emulsion. In different embodiments, said Foot-and-Mouth Disease Virus antigen may be of either wild-type FMDV, genetically modified and/or attenuated FMDV strains, or recombinantly expressed FMDV structural proteins such as virus like particles (VLPs) of serotypes A, C, O, Asia1, SAT1, SAT2, or SAT3.

In the ninety-third embodiment, the invention provides the vaccine composition of the ninety-second embodiment, wherein the immunostimulatory oligonucleotide is a CpG, and the polycationic carrier is DEAE dextran.

In ninety-fourth embodiment, the invention provides the vaccine composition of the ninety-second or ninety-third embodiment, wherein the antigen is the invention provides the vaccine composition of claim the ninety-eighth or ninety-ninth embodiment, wherein the antigen is derived from the genetically modified FMD-LL3B3D platform virus which is attenuated in cattle and pigs, specifically FMD-LL3B3D-A24 Cruzeiro.

In the ninety-fifth embodiment, the invention provides a use of the vaccine composition of any one of the ninety-second or ninety-fourth embodiment for treatment or prevention of FMD in cattle.

In the ninety-sixth embodiment, the invention provides a vaccine composition comprising a *Streptococcus uberis* (*S. uberis*) antigen and an adjuvant formulation comprising an oily phase, said oily phase being present in the amount of at least 50% v/v of the composition; a polycationic carrier; and
   a) an immunostimulatory oligonucleotide;
   b) a combination comprising a saponin, a sterol, and a quaternary amine; or
   c) a combination thereof.

In the ninety-seventh embodiment, the invention provides a vaccine composition of the ninety-sixth embodiment, wherein the antigen is a *S. uberis* adhesion molecule or an immunogenic fragment thereof.

In the ninety-eighth embodiment, the invention provides a use of the vaccine according to any one of ninety sixth or ninety-seventh embodiment for treatment or prevention of an infection caused by *S. uberis*.

The following examples are presented as illustrative embodiments, but should not be taken as limiting the scope of the invention. Many changes, variations, modifications, and other uses and applications of this invention will be apparent to those skilled in the art.

EXAMPLES

Example 1. Development of Recombinant Vaccination Strategy to Enhance Immunity Against Necrotic Enteritis The aim of the study was to evaluate the effects of in vivo vaccination with adjuvanted recombinant clostridia vaccine against live challenge infection with *Eimeria maxima* and *Clostridium perfringens* in Necrotic Enteritis Disease Model.

Materials and Methods
Recombinant Proteins:
Full-length coding sequences for genes encoding *C. perfringens* (ATCC 13124, American Type Culture Collection, Manassas, Va.) NetB and EF-Tu were cloned by PCR into the pET32a(+) vector with an $NH_2$-terminal polyhistidine epitope tag. Cloned genes were transformed into competent *Escherichia coli*, the bacteria were cultured for 16 h at 37° C., and induced for 5 h at 37° C. with 1.0 mM isopropyl O-D-thiogalactopyranoside (Amresco, Cleveland, Ohio). Bacteria were harvested by centrifugation at 10,000 rpm for 10 min at 4° C., resuspended in PBS, disrupted by sonication, and centrifuged at 10,000 rpm for 15 min. The supernatant was incubated for 1 h at 22° C. with Ni-NTA agarose (Qiagen, Valencia, Calif.), the resin was washed with PBS, and purified clostridial proteins were eluted with 250 mM imidazole in PBS, pH 9.2. Protein purity was confirmed on Coomassie blue-stained SDS-acrylamide gels. Protein concentration was determined using a commercial kit from Sigma.

Animals:
One-day-old Broiler birds (Ross/Ross) hatched at the Longeneckers Hatchery (Elizabethtown, Pa.) were be transported to the BARC-East, Building 1082 and the chicks were housed in Petersime starter brooder units according to the established guidelines of BARC Small Animal Care Committee. Birds were kept in brooder pens in an *Eimeria*-free facility and transferred into large hanging cages in a separate location where they were infected and kept until the end of experimental period for the live challenge infection study. All procedures regarding transportation, measuring body weight, infection, and collecting blood and spleen were approved by the BARC Small Animal Care Committee (SOP attached). ARS BARC Small Animal Care Committee established guidelines for animal experiments at BARC and conducts regular inspection of all animal facilities.

Immunization:
The primary immunization was performed by subcutaneously injecting one-day old broiler chicks with 100 ul vaccine (Ag 100 ug/dose). The secondary immunization was performed by subcutaneously injecting s even-day-old broiler chicks were injected subcutaneously with 100 ul vaccine (Ag 100 ug/dose).

*Eimeria* Challenge:
BARC strains of *Eimeria* spp. which have been maintained in the Animal Parasitic Diseases Laboratory and propagated according to the established procedure. *E. maxima* (41A) was be cleaned by floatation on 5% sodium hypochlorite, washed three times with PBS, and viability enumerated by trypan blue using a hemocytometer. The oocyst number is based on only sporulated oocysts. Six days after booster immunization, chickens were inoculated esophageally with 10,000 of *E. Maxima* using an inoculation needle.

*C. perfringens* Challenge:
Four days after *Eimeria* infection, birds of NE Groups were inoculated esophageally with $1 \times 10^9$ CFU *Clostridium perfringens* each using an inoculation needle.

Analysis:
Birds were weighed on the day of arrival, just before challenge with EM, before challenge with *C. perfringens*, 2 days post C.P, and 10 days post C.P. challenge to calculate the weight gain.

For scoring intestinal lesions, birds (5 birds/group) were sacrificed two days post C.P. infection. Approximately 20 cm intestinal segments extending 10 cm anterior and posterior to diverticulum were obtained and cut longitudinally. Lesion scores were evaluated by 2 independent observers from 0 to 4 in ascending order of severity of the lesion.

Two major *C. perfringens* virulence factors in chickens are alphatoxin and the NetB (necrotic enteritis B-like) toxin, both of which are implicated in the pathogenesis of NE. Additional *C. perfringens* proteins that may be involved in bacterial pathogenesis and host protective immunity including pyruvate: ferredoxin oxidoreductase (PFO) and elongation factor G (EF-G) were previously reported to induce protective immunity against experimental challenge infection with *C. perfringens*. Accordingly antibody titres to these factors were determined as described below.

Five birds per group were selected at random for blood that was collected by cardiac puncture immediately following euthanasia. Sera were obtained by low speed centrifugation and used in an enzyme-linked immunosorbent assay (EUSA) to measure a-toxin-, NetB-, EF, and PFO-specific antibody levels. Briefly, 96-well microtiter plates were coated overnight with 1.0 pg/well of purified recombinant a-toxin-, NetB-, EF, and PFO proteins. The plates were washed with PBS containing 0.05% Tween (PBS-T) and blocked with PBS containing 1% BSA. Sera (100 pl/well) were incubated for 2 hr at room temperature with gentle agitation. The plates were washed with PBS-T, and bound antibody was detected with peroxidase-conjugated rabbit anti-chicken IgG (Sigma, St. Louis, Mo.) and peroxidase-specific substrate. Optical density (OD) at 450 nm was measured with an automated microplate reader (Bio-Rad, Richmond, Calif.).

Statistical analysis: All values are expressed as mean±SEM. Mean values for body weight gain and lesion score are compared among groups by the Turkey test following ANOVA using SPSS 15.0 for Windows (SPSS Inc., Chicago, Ill.). Differences among means will be considered significant at p<0.05.

The Experimental Design is illustrated in table 1.

TABLE 1

| Group # | Bird (Number) | Protein (100 μg/bird) | Adjuvant | Infection for NE (EM + CP)* |
|---|---|---|---|---|
| 1 | 15 | – | 10 mM Buffer | – |
| 2 | 15 | – | 10 mM Buffer | + |
| 3 | 15 | NetB (50 μg) + EF-Tu (50 μg) | 10 mM Buffer | + |
| 4 | 15 | NetB (50 μg) + EF-Tu (50 μg) | 1. TXO | + |
| 5 | 15 | NetB (50 μg) + EF-Tu (50 μg) | 2. TCMO | + |
| 6 | 15 | NetB (50 μg) + EF-Tu (50 μg) | 3. XO | + |
| 7 | 15 | NetB (50 μg) + EF-Tu (50 μg) | 4. XOM | + |
| 8 | 15 | NetB (50 μg) + EF-Tu (50 μg) | 5. SP-OIL | + |
| 9 | 15 | NetB (50 μg) + EF-Tu (50 μg) | 6. 5% AMPHIGEN ® | + |
| 10 | 15 | NetB (50 μg) + EF-Tu (50 μg) | 7. 5% AMPHIGEN ® + poly I:C | + |
| 11 | 15 | NetB (50 μg) + EF-Tu (50 μg) | 8. 5% AMPHIGEN ® + CpG | + |
| 12 | 15 | NetB (50 μg) + EF-Tu (50 μg) | 9. 5% AMPHIGEN ® + DEAE Dextran | + |
| 13 | 15 | NetB (50 μg) + EF-Tu (50 μg) | 10. 5% AMPHIGEN ® + DDA | + |

*Chickens were orally infected with $1.0 \times 10^4$ oocysts/bird of E. maxima (EM) at day 14 post-hatch and with $1.0 \times 10^9$ CFU/bird of C. perfringens (CP) at day 18.

The compositions of the adjuvants were as follows (per 50 ul):

TXO: SEQ ID NO: 8 was present in the amount of 1 ug, Dextran DEAE was present in the amount of 5 ug, light mineral oil was present in the amount of 51% v/v of the composition TCMO: SEQ ID NO: 8 was present in the amount of 1 ug, cholesterol was present in the amount of 1 ug, MPL-A was present in the amount of 1 ug/50 ul dose, light mineral oil was present in the amount of 51% v/v of the composition XO: Dextran DEAE was present in the amount of 5 ug, light mineral oil was present in the amount of 51% v/v of the composition.

XOM: Dextran DEAE was present in the amount of 5 ug, light mineral oil was present in the amount of 51% v/v of the composition, MPL-A was present in the amount of 1 ug.

5% AMPHIGEN®+poly I:C: poly I:C was present in the amount of 1 ug.

5% AMPHIGEN®+CpG: SEQ ID NO: 8 was present in the amount of 1 ug.

5% AMPHIGEN®+DEAE Dextran: DEAE dextran was present in the amount of 25 ug

5% AMPHIGEN®+DDA: DDA was present in the amount of 1 ug.

The body weight gain was significantly decreased by EM and CP infection in the NE control group (P<0.05). However, the body weight gain generally increased in the groups immunized with recombinat CP proteins (Net B+EF) by 4~21%. The significant difference with NE control was found in Prot TCMO group which were imunized with CP proteins conjugated with TCMO adjuvant.

TABLE 2

| Body weight gain | | | |
|---|---|---|---|
| Group | Treatment | Mean | SEM |
| 1 | Cont | 347.93 | 9.387 |
| 2 | NE cont | 286.36 | 14.436 |
| 3 | Prot | 317.86 | 7.828 |
| 4 | Prot TXO | 316.42 | 8.826 |
| 5 | Prot TCMO | 345.73 | 11.745 |
| 6 | Prot XO | 334.67 | 8.605 |
| 7 | Prot XOM | 331.17 | 11.387 |
| 8 | Prot SPO | 304.09 | 10.330 |
| 9 | Prot AMP | 310.09 | 9.479 |
| 10 | Prot AMPPIC | 314.86 | 9.571 |
| 11 | Prot AMP CPG | 313.82 | 11.976 |
| 12 | Prot AMP DEAE | 299.20 | 15.000 |
| 13 | Prot AMP DDA | 301.25 | 10.440 |

TABLE 3

| Lesion score | | | |
|---|---|---|---|
| Group | | Mean | SEM |
| 2 | NE cont | 3.0 | 0.0 |
| 3 | Prot | 2.7 | 0.2 |
| 4 | Prot TXO | 2.5 | 0.2 |
| 5 | Prot TCMO | 2.6 | 0.2 |
| 6 | Prot XO | 1.7 | 0.2 |
| 7 | Prot XOM | 2.4 | 0.2 |
| 8 | Prot SPO | 2.4 | 0.2 |
| 9 | Prot AMP | 1.7 | 0.1 |
| 10 | Prot AMPPIC | 2.1 | 0.1 |
| 11 | Prot AMP CPG | 2.3 | 0.2 |
| 12 | Prot AMP DEAE | 2.1 | 0.1 |
| 13 | Prot AMP DDA | 2.2 | 0.2 |

Six days after EM infection and 2 days after CP infection, serum antibody responses against a-toxin, Net-B, EF, and PFO were evaluated. The results are provided in Table 4. Briefly, CP protein generally increased Ab titers against CP antigens in the birds immunized with CP proteins. Ab responces to Net B, EF,and PFO antigens were much higher than to a-toxin.

TABLE 4

Ab responses to Net B, EF, and PFO antigens

| Groups | ε-toxin Mean | SEM | Net B Mean | SEM | EF Mean | SEM | PFO Mean | SEM |
|---|---|---|---|---|---|---|---|---|
| 2 NE cont | .36 | .02 | .33 | .01 | .21 | .01 | .22 | .01 |
| 3 Prot | .40 | .04 | .44 | .05 | .40 | .09 | .36 | .05 |
| 4 Prot TXO | .39 | .03 | .41 | .04 | .56 | .05 | .40 | .03 |
| 5 Prot TCMO | .34 | .02 | .42 | .03 | .48 | .06 | .40 | .06 |
| 6 Prot XO | .34 | .02 | .53 | .05 | .38 | .07 | .36 | .04 |
| 7 Prot XOM | .33 | .02 | .40 | .04 | .55 | .03 | .41 | .04 |
| 8 Prot SPO | .30 | .01 | .33 | .02 | .19 | .02 | .20 | .02 |
| 9 Prot AMP | .37 | .01 | .33 | .00 | .22 | .03 | .32 | .07 |
| 10 Prot AMPPIC | .32 | .02 | .53 | .06 | .36 | .10 | .33 | .02 |
| 11 Prot AMP CPG | .42 | .02 | .41 | .02 | .24 | .08 | .28 | .01 |
| 12 Prot AMP DEAE | .38 | .02 | .53 | .05 | .17 | .02 | .23 | .03 |
| 13 Prot AMP DDA | .41 | .01 | .58 | .02 | .45 | .03 | .36 | .03 |

Example 2: Hen Anti-Myostatin Vaccine

Myostatin is a secreted growth differentiation factor that is a member of the TGF beta protein family that inhibits muscle differentiation and growth. Myostatin is produced primarily in skeletal muscle cells, circulates in the blood and acts on muscle tissue, by binding a cell-bound receptor called the activin type II receptor. Accordingly, inhibition of myostatin results in animals having an increased amount of meat/muscle. One approach to lowering the amount of myostatin in an animal is to generate an anti-myostatin immune response, which can be conveniently measured by the titers of anti-myostatin antibody. In this example, a hen model was used.

Cobb 500 Parent Stock and Ross 308 hens (age 12 to 10 weeks, respectively) were primed with a vaccine containing Myostatin Conjugated Peptide and an adjuvant formulation. The adjuvant formulations used in the study are shown in Table 5.

TABLE 5

Treatment groups.

| Treatment | Adjuvant | Carrier | Dose |
|---|---|---|---|
| T01 | CFA/IFA | CRM | 50 ug |
| T02 | IFA/CFA | CRM | 50 ug |
| T03 | CFA/IFA | KLH/CRM | 50 ug |
| T04 | TCMO | KLH/CRM | 50 ug |
| T05 | TCMO | CRM | 200 ug/50 ug |
| T06 | TMO | CRM | 200 ug/50 ug |
| T07 | TCMO | CRM | 50 ug |
| T08 | MO | CRM | 50 ug |
| T09 | TMO | CRM | 50 ug |
| T10 | TXO | CRM | 50 ug |

The designation "200 ug/50 ug" refers to the amount of antigen in prime/boost dose, volume 0.2 ml.

The components in the adjuvants are as described in Table 6.

Cobb 500 Parent Stock and Ross 308 hens were primed on week 12 or 10 and boosted on week 18. The serum titers of anti-myostatin antibody were measured by ELISA before the vaccination and every two weeks after the prime until 22 and 20 weeks of age, respectively.

Groups T06, T07, T09 and T10 produced the highest responses (antibody mean geometric titers between 50000 and 15000 on week 22). Among these four groups, Cobb 500 birds in Groups T06 and T07 demonstrated mean geometric titers above 100,000.

TABLE 6

| Adjuvant Name | Adjuvant Components | Adjuvant Concentration/dose |
|---|---|---|
| TCMO | SEQ ID NO: 8/Cholesterol/ MPLA/oil | 10 ug/10 ug/5 ug/Drakeol 5 oil (45%), SPAN ® 80 (6.3%) & TWEEN ® 80 (1.45%) |
| MO (20:80 W:O) | MPLA (20:80 W:O) low viscosity emulsion | MPLA-5 ug/Drakeol 6 mineral oil, SPAN & TWEEN 80 |
| TMO (20:80 W:O) Use MO emulsion and admix CpG and conjugated peptides | SEQ ID NO: 8/MPLA (20:80 W:O) low viscosity emulsion | 10 ug/5 ug/Drakeol 6 mineral oil, SPAN & TWEEN 80 |
| TXO | SEQ ID NO: 8/DEAE-Dextran | 10 ug/20 ug/Drakeol 5 mineral oil, (45%), SPAN ® 80 (6.3%) & TWEEN ® 80 (1.45%) |

Example 3. Vaccines Against *T. pyogenes*

*Truepurella pyogenes* (formerly *Arcanobacterium pyogenes*, and formerly *Actinomyces pyogenes* and also *Corynebacterium pyogenes*) often cause severe clinical metritis in cattle characterized by thick, purulent secretion. The foul odor sometimes associated with this condition is probably caused by anaerobic bacteria that are also present but not detected by routine cultural methods. The disease is most frequent in dry cows or heifers before or at the time of calving, and occasionally occurs in lactating animals as a sequel to teat or udder injury. Economically important diseases caused by this organism include metritis, and abortion in dairy cows and liver abscesses in feedlot cattle. Pyolysin (PLO), a cholesterol-dependent cytolysin expressed by *Truepurella pyogenes*, is an important host-protective antigen.

Angus crossbred cattle of approximately 14 months of age were used in this study. Animals were in overall good health and free of any complicating disease at enrollment. Animals had ad libitum access to feed and water.

Formulations: All bacteria (*E. coli* and *T. pyogenes*) at $1 \times 10^9$ per dose. Pyolysin was administered at 150 micrograms per dose to animals in groups T02-T07. Group T01 was used as a control.

Adjuvant formulations tested in this study were as follows:

ISC/Poly IC—ISC 1000 μg/Poly I:C 50 μg in a 2 mL dose

ISC/CpG—ISC 1000 μg/100 μg CpG (SEQ ID NO: 8) in a 2 mL dose

TXO—CpG 100 g (SEQ ID NO: 8)/DEAE Dextran/Mineral oil 5LT NF in a 2 mL dose

QCDCRT—Quil A 150 μg/cholesterol 150 μg/DDA 100 g/CARBOPOL® (polyacrylic polymer) 0.0375%/R1005 1000 μg/CpG (SEQ ID NO: 8) 100 μg in a 2 mL dose QAC—Quil A 500 μg/cholesterol 500 μg/AMPHIGEN® (lecithin oil emulsion) 2.5% in a 2 mL dose Pyolysin antibody was measured using an indirect ELISA, antigen on the plate followed by serum sample (primary antibody) followed by anti-bovine IgG conjugate was measured at days 0, 28, and 56.

All samples and controls were diluted 1:2000, and response determined by calculation of the ratio of the OD of the sample to the OD of the positive control (Pos ctrl was a pool of serum from convalescent animals). Antibody was detected by HRP-conjugated sheep anti-bovine IgG.

TABLE 7

Study design

| Treatment Group | Number of Animals | Treatment* | Day | Dose | Dose units | Route† | Uterine Challenge |
|---|---|---|---|---|---|---|---|
| T01 | 8 | Saline | 0, 28 | 2 | mL | SC, SC | Day 56 $5 \times 10^8$ |
| T02 | 8 | *E. coli* + T (A). pyogenes + PLO in ISC/Poly:IC | 0, 28 | 2 | mL | IN, SC | Day 56 $5 \times 10^8$ |
| T03 | 8 | *E. coli* + T (A). pyogenes + PLO in ISC/CpG | 0, 28 | 2 | mL | IN, SC | Day 56 $5 \times 10^8$ |
| T04 | 8 | *E. coli* + T (A). pyogenes + PLO in TXO | 0, 28 | 2 | mL | SC, SC | Day 56 $5 \times 10^8$ |
| T05 | 8 | *E. coli* + T (A). pyogenes + PLO in QCDCRT | 0, 28 | 2 | mL | IN, SC | Day 56 $5 \times 10^8$ |
| T06 | 8 | *E. coli* + T (A). pyogenes + PLO in QAC | 0, 28 | 2 | mL | SC, SC | Day 56 $5 \times 10^8$ |
| T07 | 8 | PLO in ISC/Poly:IC | 0, 28 | 2 | mL | IN, SC | Day 56 $5 \times 10^8$ |

*E. coli strain 51323 + T (A). pyogenes strain 51496, PLO = pyolysin
†SC = Subcutaneous, IN = Intranasal.

The results are shown in Table 8

TABLE 8

| | LSM of IgG to PLO (Time Point is Day on Study) | | |
|---|---|---|---|
| Treatment No. | Day 00 | Day 28 | Day 56 |
| T01 | 0.216 | 0.226 | 0.208 |
| T02 | 0.274 | 0.245 | 0.444 |
| T03 | 0.252 | 0.229 | 0.451 |
| T04 | 0.205 | 0.506* | 0.590* |
| T05 | 0.291 | 0.246 | 0.373 |
| T06 | 0.243 | 0.512* | 0.687* |
| T07 | 0.315 | 0.280 | 0.624 |

Groups T04 and T06 (adjuvants TXO and QAC) performed significantly better than control (P<0.05). In addition, multiple trends among different treatment groups (selected as differences where P<0.1) have been found. These trends are summarized in Table 9.

TABLE 9

Differences between the groups on days 0 (first parameter), 28 (second parameter), 56 (third parameter). "Y" indicates that P <0.1.

| | T01 | T02 | T03 | T04 | T05 | T06 | T07 |
|---|---|---|---|---|---|---|---|
| T01 | X | X | X | X | X | X | X |
| T02 | N, N, Y | X | X | X | X | X | X |
| T03 | N, N, Y | N, N, N | X | X | X | X | X |
| T04 | N, Y, Y | Y, Y, Y | N, Y, N | X | X | X | X |
| T05 | Y, N, Y | N, N, N | N, N, N | Y, Y, N | X | X | X |
| T06 | N, Y, Y | N, Y, Y | N, Y, Y | N, N, Y | N, Y, Y | X | X |
| T07 | Y, N, Y | N, N, Y | N, N, N | Y, Y, N | N, N, N | Y, Y, Y | X |

Example 4. Evaluation of Pyolysin Vaccine Formulations in Lactating Dairy Cows Against Metritis Challenge The objective of this study was to evaluate the efficacy of native and recombinant pyolysin vaccine formulations, adjuvanted with TXO, in non-pregnant lactating Holstein or Holstein cross dairy cows, using an artificial metritis challenge model.

Animals were in overall good health, free of any complicating diseases, and did not receive any chemotherapy, systemic antibiotic or other anti-inflammatory medication during the seven (7) days preceding and post vaccination and challenge. They were in their $1^{st}$ to $3^{rd}$ parity, had no previous history of metritis, and were not culture positive for *T. pyogenes* pre-challenge (day −1 or 0). Animals that developed clinically significant concurrent disease during the study were removed.

Animals had ad libitum access to feed for at least 20 hours in each 24-hour period, the only exception being when they were milked. A basal custom blended feed ration, representative of the industry for lactation, was used. Animals were acclimated for at least 7 days prior to the start of the study. The formulated vaccines administered to the cows (n=20 per group) contained the following components: T01—Saline; T02—TXO+native pyolysin (nPLO); T03—TXO+recombinant pyolysin (rPLO). Recombinant pyolysin was obtained by cloning, expression, and purification of the antigen from *Corynebacterium glutamicum*. The purified protein was then inactivated by treatment with formalin. Native pyolysin, expressed and purified from *Trueperella pyogenes*, was also inactivated by treatment with formalin. The TXO adjuvant contained CpG oligonucleotides, DEAE-Dextran, mineral oil, and the surfactants Span 80 and Tween 80.

On the day of vaccination, the appropriate IVP (Table 10) was administered via the subcutaneous route. Vaccine was administered in the neck on Day 0, and on the opposite side of the neck on Day 28. The site of vaccine administration was evaluated on Study Days 0, 1, 2, 3, 7, 28, 29, 30, 31, 35, 49 and 77 for injections site reactions. On the day of vaccination, site of administration was evaluated to confirm that no swellings were present prior to vaccine administration. On Study Day 28, 49 & 77 both sides of the neck were observed. Injection site evaluations were recorded. Rectal temperature were also measured and recorded on Study Days 0 (prior to the $1^{st}$ vaccination), 1, 2, 3, 7, 28 (prior to the $2^{nd}$ vaccination), 29, 30, 31 and 35 during the vaccination phase. Rectal temperature were also measured and recorded on Challenge Days 0 through 28.

Post-vaccination clinical observations were recorded on Study Days 0, 1, 2, 3, 7, 28, 29, 30, 31 and 35 (during the vaccination phase). In addition, clinical observations were observed and recorded during the Challenge phase starting on Day 49 through 77.

Antibody responses to pyolysin were determined by EUSA on Study Days 0, 28, 49, and last day of the study (d77). A hemolytic inhibition assay was also performed on each serum sample. This assay measures the anti-pyolysin antibody response, which correlates with the biological activity (protection).

TABLE 10

| Group | # of Animals | Treatment | Day | Route |
|---|---|---|---|---|
| T01 | 20 | Saline | 0, 28 | SQ |
| T02 | 20 | TXO + Native Pyolysin | 0, 28 | SQ |
| T03 | 20 | TXO + Recombinant Pyolysin | 0, 28 | SQ |

Prior to challenge, the ovarian cycle of all cows was synchronized. Progesterone was administered prior to challenge, and daily throughout the 28 day challenge phase. Using a sterile cannula similar to a breeding cannula, 10 mL of an *Escherichia coli* challenge strain and 10 mL of a *Trueperella pyogenes* challenge strain (predetermined challenge doses), each taken up in a separate syringe, was infused into the uterus of all cows on challenge day 0. To ensure complete delivery of challenge material, the cannula was flushed out with 10 mL of sterile culture media.

Challenge was considered successful if at least 60% of the animals in treatment group T01 (control group) developed metritis. The presence of metritis would be indicated by the presence of a mucopurulent uterine/vaginal discharge with a score of 2 2. (This scoring system was adopted from the method described by Sheldon et al., Theriogenology, 65:1516-1530, 2006; in which scores of 0 and 1 were considered normal.)

The primary variable was the presence of a mucopurulent uterine/vaginal discharge with a score of 2 2, which indicates the presence of metritis. The uterine/vaginal discharge was collected using an aseptic Simcro MetriCheck™ device with an aseptic cup, and scored beginning on Challenge Day 0 through 28 (study day 49 through 77).

A treatment was considered efficacious if only T01 cows developed clinical metritis, or if the duration and/or proportion of days of mucopurulent vaginal discharge (score 2 2) was significantly shorter (p=<0.1) compared to controls. If there was no significant difference between groups for duration and proportion of days with metritis, then the frequency of *T. pyogenes* isolation from the uterine bacterial swab was used as supportive data for vaccine efficacy. Safety of respective vaccines was assessed based on injection site evaluations, rectal temperatures and any adverse effects on lactation.

Metritis data collected (vaginal/uterine discharge present, Yes/No; vaginal/uterine discharge score) was summarized for each animal at each time-point, and utilized to determine the frequency distributions of each category for each treatment at each time-point. Frequency distributions of whether an animal was Normal/Abnormal (Normal is a score=0 or 1; Abnormal is a score 2 2) for each metritis sign (e.g. vaginal/uterine discharge score) were summarized by treatment and time-point. Whether an animal ever had an abnormal (a score 2 2) uterine discharge score was summarized by treatment, using a generalized linear mixed model (Proc Glimmix), with a binomial error distribution and a logit link function. The statistical model included the fixed effect of treatment, and the random effect of batch. Contrasts were made between treatment groups. This was repeated for each metritis variable described in this paragraph. If Proc Glimmix did not converge for a metritis variable, then Fisher's Exact Test was utilized instead to compare treatment groups.

Duration of an abnormal score (for each metritis variable) was determined for each animal, and calculated as "(last time-point abnormal minus first time-point abnormal)+1". Duration of the abnormal score was set to zero for animals that had no time-points with an abnormal score for that metritis variable. Duration of the abnormal score was calculated as "(last scheduled time-point of data collection minus first time-point abnormal)+1" for animals that were removed from the study prior to the last scheduled data collection time-point for that metritis variable. Duration of abnormal score (for each metritis variable) was log transformed, and then analyzed with a general linear mixed model with fixed effect: treatment, and random effect: residual. Linear combinations of the parameter estimates were used in a priori contrasts after testing for a significant (P50.10) treatment effect. Comparisons were made between treatments. Back-transformed least squares means, their standard errors and their 90% confidence intervals were calculated for each treatment group from least squares parameter estimates obtained from the analyses.

Proportion of days with an abnormal score (for each metritis variable), as well as proportion of days with both a normal *E. coli* and *T. pyogenes* absent from the discharge (absent is considered a value <=1+), were determined for each animal. Each was then transformed using the arc sin square root transformation prior to analysis. These transformed proportion-of-days variables were then each analyzed with a general linear mixed model with fixed effect: treatment, and random effect: residual. Linear combinations of the parameter estimates were used in a priori contrasts after testing for a significant (P<0.10) treatment effect. Comparisons were made between treatments. Back-transformed least squares means, their standard errors, and their 90% confidence intervals were calculated for each treatment group from least squares parameter estimates obtained from the analyses. Frequency distributions of whether an animal had *E. coli* present (present is considered a value >1+), *T. pyogenes* present (present is considered a value >1+), and both *E. coli* and *T. pyogenes* present (present is considered a value >1+), were summarized by treatment at each timepoint.

Results. The antibody response to pyolysin was assessed by ELISA, measuring serum IgG levels. The results (Table 11), presented as least square mean (LSM) titers, indicate that titers were significantly higher in cows in T02 and T03, versus T01, on study days 28, 49 and 77. They also suggest that there were no statistically significant differences between the titers of groups T02 and T03. With respect to antibody titers in the uterus, also assessed by ELISA, the results (Table 12) demonstrated that there were significantly higher titers on days 49 and 77 in cows within T02 and T03, versus those in T01, on those same days. As for hemolytic-inhibiting antibodies, the results in table 13 indicate that animals in T02 had significantly higher titers on study days 49 and 77 than those in groups T01 and T03.

TABLE 11

LSM[1] of Serum IgG Titers S:P ratio

|  | Day 0 | Day 28 | Day 49 | Day 77 |
|---|---|---|---|---|
| T01 | 0.250 $^a$ | 0.197 $^a$ | 0.178 $^a$ | 0.366 $^a$ |
| T02 | 0.226 $^a$ | 0.645 $^b$ | 0.782 $^b$ | 0.820 $^b$ |
| T03 | 0.224 $^a$ | 0.626 $^b$ | 0.725 $^b$ | 0.746 $^b$ |

[1]Different superscripts represent significant differences between groups.

TABLE 12

LSM[1] of IgG anti-PLO in Uterus

|  | Day 49 | Day 77 |
|---|---|---|
| T01 | 0.033$^a$ | 0.120$^a$ |
| T02 | 0.433$^b$ | 0.353$^b$ |
| T03 | 0.444$^b$ | 0.382$^b$ |

[1]Different superscripts represent significant differences between groups.

TABLE 13

LSM[1] of HI Antibody S:P ratio in Serum

|  | Day 0 | Day 28 | Day 49 | Day 77 |
|---|---|---|---|---|
| T01 | 0.09 $^a$ | 0.10 $^a$ | 0.11 $^a$ | 0.12 $^a$ |
| T02 | 0.08 $^a$ | 0.78 $^b$ | 2.75 $^c$ | 1.12 $^c$ |
| T03 | 0.09 $^a$ | 0.77 $^b$ | 2.13 $^b$ | 0.84 $^b$ |

[1]Different superscripts represent significant differences between groups.

Regarding the primary variable assessed, the level of mucopurulent uterine/vaginal discharge (Vaginal Discharge Score, or VDS), when the duration of metritis was measured, it was significantly shorter in group T02, versus groups T01 and T03, as measured at 7 and 10 days following challenge with bacteria (Tables 14, 15).

TABLE 14

Duration of Metritis (VDS ≥ 2); LSM[1]

|  | Week 1 (days 50 to 56) | Challenge Day 0 to 10 |
|---|---|---|
| T01 | 4.2$^a$ | 7.1$^a$ |
| T02 n-PLO | 2.2$^b$ | 4.2$^b$ |
| T03 r-PLO | 4.3$^{a,c}$ | 7.4$^{a,c}$ |

[1]Different superscripts represent significant differences between groups.

TABLE 15

|  | P values; 1$^{st}$ 7 days | P values; 1$^{st}$ 10 days | Treatment Differences |
|---|---|---|---|
| T01 v T02 | 0.0096 | 0.0276 | YES |
| T01 v T03 | 0.8658 | 0.6962 | NO |
| T02 v T03 | 0.0063 | 0.0109 | YES |

As for the % of days that metritis was evident (i.e. a VDS >2) within 10 days following challenge (Tables 16 and 17), it is evident that group T02 had fewer abnormal days, compared to groups T01 and T03. Also, it was demonstrated that *T. pyogenes* was most frequently isolated from cows in group T03 (data not shown). Thus, the vaccine effect was most prominent in group T02 (native pyolysin+TXO).

TABLE 16

% Days Normal

|  | Week 1 | Challenge Day 0 to 10 |
|---|---|---|
| T01 | 70 ± 6.7% | 75 ± 6.1% (25%) |
| T02 | 44.3 ± 10.4% | 53.1 ± 9.7% (46.9%) |
| T03 | 67.2 ± 6.4% | 73.4 ± 5.7% (26.6%) |

TABLE 17

|  | P values; 1$^{st}$ 7 days | P values; 1$^{st}$ 10 days |
|---|---|---|
| T01 v T02 | 0.0472 | 0.0594 |
| T01 v T03 | 0.7712 | 0.8204 |
| T02 v T03 | 0.0699 | 0.0790 |

An additional study was conducted to evaluate the efficacy of experimental metritis vaccines, in novel adjuvant formulations, in pregnant dairy cows. In this study, pregnant cows were vaccinated during the dry period. Efficacy was measured during the first 10 days after calving (parturition).

Pregnant Holstein or Holstein cross cows, in their 1$^{st}$ through 3$^{rd}$ lactation, were selected for the study. All selected cows were in overall good health, had no previous history of metritis, and had a known expected calving date. They were also free of any complicating diseases, and did not receive any chemotherapy, systemic antibiotic, or other anti-inflammatory medication during the seven (7) days preceding and following vaccination. Animals that developed clinically significant concurrent disease at any time during the study were removed. During the course of the study, animals had ad libitum access to feed at least 20 hours in each 24-hour period, the only exception being during milking. Animals also had ad libitum access to water throughout the study.

The vaccines administered to the groups (n=15/group) were as follows: animals in T01 received a 2 ml vaccine consisting of saline; those in T02 received a 2 ml vaccine consisting of ISCOMS/Poly I:C+nPLO; those in T03 received a 2 ml vaccine consisting of TXO+nPLO; those in T04 received a 2 ml vaccine consisting of TXO+*Escherichia coli*+*Trueperella pyogenes*+nPLO. (All vaccine antigens were formalin-inactivated.)

Following their arrival, animals were allowed to acclimate for 7 days. Approximately 2 months prior to calving (Study Day 0), animals received the first vaccination, subcutaneously in the left side of the neck, except that animals in group T02 received the vaccine intranasally (Table 18). Twenty-eight days later, all animals received the second vaccination, subcutaneously in the right side of the neck (Table 18). Beginning with the first vaccination, all cows were dried off.

TABLE 18

| Group | # of Animals | Treatment | Day | Route |
|---|---|---|---|---|
| T01 | 15 | Saline | 0, 28 | SC, SC |
| T02 | 15 | ISC + Pyolysin (PLO) | 0, 28 | IN, SC |
| T03 | 15 | TXO + Pyolysin (PLO) | 0, 28 | SC, SC |
| T04 | 15 | TXO + *E. coli* + *T. pyogenes* + Pyolysin (PLO) | 0, 28 | SC, SC |

Beginning on the day of calving, and continuing for 21 days afterwards, the presence of a uterine/vaginal discharge was assessed, and if present, collected and assigned a score, with a score of >2 indicating the presence of metritis. Approximately 30 mL of blood was collected (Study Days 0, 28, and 49), for determination of antibody responses to *E. coli*, *T. pyogenes*, and pyolysin by ELISA. Any adverse reactions, not otherwise captured as part of the procedural data collection, were documented.

The primary variable was the presence of a mucopurulent uterine/vaginal discharge; a score of ≥2 would indicate the presence of metritis. A treatment was considered efficacious if only T01 cows developed clinical metritis, or if the duration of mucopurulent vaginal discharge (score ≥2) was significantly shorter (p=<0.1) compared to controls. If present, a mucopurulent discharge was collected post-parturition.

Comparisons were made between treatments at each time point. Least squares means (back-transformed for serology data), their standard errors, and their 90% confidence intervals were calculated from least squares parameter estimates obtained from the analyses. Ranges and number of animals with data were calculated for each treatment group at each time-point.

Metritis data collected (vaginal/uterine discharge present, Yes/No; vaginal/uterine discharge score; clinical signs) were summarized for each animal at each time-point, and were utilized to determine the frequency distributions of each category for each treatment at each time-point. Frequency distributions of whether an animal was Normal/Abnormal (normal is a score=0 or 1; abnormal is a score ≥2) for each metritis sign (e.g. vaginal/uterine discharge score) was summarized by treatment and time-point. Whether an animal ever had an abnormal (a score ≥2) uterine discharge score was summarized by treatment, and analyzed using a generalized linear mixed model (Proc Glimmix), with a binomial error distribution and a logit link function. The statistical model included the fixed effect of treatment and the random effects of batch, and block within batch. Contrasts were made between treatment groups (this was repeated for each metritis variable described in this paragraph). If Proc Glimmix does not converge for a metritis variable, then Fisher's Exact Test was utilized instead to compare treatment groups.

Duration of an abnormal score (for each metritis variable) was determined for each animal, and was calculated as "(last time-point abnormal minus first time-point abnormal)+1". Duration of the abnormal score was set to zero for animals that had no time-points with an abnormal score for that metritis variable. Duration of the abnormal score was calculated as "(last scheduled time-point of data collection minus first time-point abnormal)+1" for animals that were removed from the study prior to the last scheduled data collection time-point for that metritis variable. Duration of abnormal score was analyzed with a general linear mixed model with fixed effect: treatment, and random effects batch, block within batch and the residual. Linear combinations of the parameter estimates were used in a priori contrasts after testing for a significant (P ≤ 0.10) treatment effect. Comparisons were made between treatments. Least squares means, their standard errors, and their 90% confidence intervals, were calculated for each treatment group from least squares parameter estimates obtained from the analyses.

Results. All cows which delivered twins were removed from the study, as such an event predisposes a cow to metritis, and can skew the data. Cows removed included 6 from control group T01, 2 each from groups T02 and T03, and 1 from group T04. Of the remaining cows in each group, the incidence of metritis, and estimated days of metritis were calculated. As can be seen in Table 19, the incidence of metritis in groups T03 and T04 was numerically lower compared to the other groups. The data also indicated that groups T03 and T04 had a shorter duration of metritis in the first 10 days following parturition than did the animals in groups T01 and T02. Thus, it can be concluded that native pyolysin, whether alone or in combination with *E. coli* and *T. pyogenes* bacterins, when adjuvanted with TXO, is effective in reducing the incidence of natural metritis in cattle.

TABLE 19

| Group (# animals) | Metritis Incidence (%) | Estimate Days LSMs | lower 90% CI | upper 90% CI |
|---|---|---|---|---|
| T01 (8) | 100 | 5.2 | 3.6 | 17.3 |
| T02 (13) | 100 | 6.7 | 5.1 | 8.7 |
| T03 (13) | 84.6 | 3.7 | 2.1 | 6.2 |
| T04 (14) | 78.6 | 3.5 | 2.0 | 5.7 |

Example 5. Mastitis Vaccines in Cattle

*E. Coli* bacterin J-5 is a known antigen for treatment of mastitis. In this study, different adjuvants combined with J-5 bacterins have been evaluated for anti-mastitis effects.

The study design is summarized in Table 20. Calving occurred on ~day 49. Samples of blood and milk were taken on days zero, 7, 28, 35, 49, 63, 70, and 84. The cows were challenged on day 70.

TABLE 20

| Treatment Group | Number of Animals | Treatment | Day | Dose | Dose units | Route |
|---|---|---|---|---|---|---|
| T01 | 20 | Saline | 0, 28 | 5.0 | mL | SC |
| T02 | 20 | Escherichia Coli Bacterin, J-5 strain (ENVIROCOR ®) | 0, 28 | 5.0 | mL | SC |
| T03 | 20 | E. coli TXO | 0, 28 | 5.0 | mL | SC |
| T04 | 20 | E. coli VACCIMAX ®-CpG | 0 | 2.0 | mL | SC |
| T05 | 20 | E. coli VACCIMAX ®-Poly I:C | 0 | 2.0 | mL | SC |

The duration of infection caused by E. Coli in groups T01-T06 was as follows: T01—252.1 hrs, T02—213 hrs, T03—191.6 hrs, T04—190.2 hrs, T05—198.7 hrs. The treatments with VACCIMAX® provided the shortest duration of infection. VACCIMAX® is an oil-in-water emulsion comprising multilamellar liposomes, wherein the antigen is packaged between the bilayers of the liposomes.

The protective effects of the treatments were also assessed by determining the stratified mitigated fraction. The higher is the stratified mitigated fraction, the greater is the protective effect. Again, the formulations with VACCIMAX® had the greatest effect (13.95-17.19 times over control), but the treatment with TXO was also effective (6.24 times over control).

Whole cell serum J-5 specific IgG total antibody responses were measured using indirect capture ELISA. The results are summarized in Tables 21 and 22.

TABLE 21

| contrast | stratified mitigated fraction | 90% confidence interval |
|---|---|---|
| T01 vs T02 | 2.1 | −14.9 to 33.3 |
| T01 vs T03 | 13.1 | −15.4 to 62.9 |
| T01 vs T04 | 30.5 | 6.4 to 47.9 |
| T01 vs T05 | 36.1 | 7.6 to 68 |

TABLE 22

| | Time Point | | | | |
|---|---|---|---|---|---|
| | Period 0 | Period 1 | Period 2 | Period 3 | Period 4 |
| T01 | 4996 [a] | 6787 [a] | 4457 [a] | 4049 [a] | 16303 [a] |
| T02 | 4425 [a] | 15106 [b] | 12498 [bc] | 20281 [c] | 51040 [c] |
| T03 | 4815 [a] | 27806 [c] | 28982 [d] | 27612 [c] | 49968 [c] |
| T04 | 3465 [a] | 17969 [bc] | 7495 [ab] | 6318 [ab] | 22010 [ab] |
| T05 | 4477 [a] | 18012 [bc] | 18404 [cd] | 7805 [b] | 17626 [ab] |

Period 0 = at 1st vaccination, 1 = at Day 28, 2 = at Day 49, 3 = prior to challenge, 4 = end of challenge.
Treatment groups with the same letter within each time point are not significantly different at alpha = 0.10

Example 6: Neospora Caninum Vaccine

Neospora caninum is a coccidian parasite that was identified as a species in 1988. It is an important cause of spontaneous abortion in infected livestock. In addition to being an important cause of cattle abortions, neosporosis is a significant disease in dogs throughout the world. If the disease is caught early, dogs may be successfully treated with clindamycin and other antiprotozoan drugs. However, the disease is often fatal to young puppies. Preventative vaccines have been tested on cattle. An inactivated vaccine was made commercially available but had mixed results. A live vaccine using attenuated N. caninum tachyzoites has been more successful but is expensive to produce. In this study, the inventors determined the effects of different adjuvants on the properties of a vaccine against N. canimum using N. caninum cyclophilin (NcCYP) and profilin (NcPro) as antigens.

Eight to 10 weeks old female BALB/c mice were used for this experiment. All animals were immunized twice at 3 week intervals with rNcCyP and rNcProf in the presence of indicated adjuvant. Three weeks after the second immunization, all animals were euthanized and spleen and blood were collected. NcCyP/NcProf-specific splenocyte proliferative response was determined with a proliferation assay (3 to 4-day). NcCyP/NcProf-specific splenocyte cytokine response was determined by stimulating the splenocytes with Neospora antigen for 48 h and the cytokine levels in supernatant determined by cytokine-specific ELISAs. Serum antibody levels were determined by ELISA. The animals were treated as summarized in Table 23.

TABLE 23

| Treatment | Adjuvant | Amounts (prepared as a 2 ml dose and 1/10th of the 2 mls was used/mouse dose.) | Antigen (Neospora caninum cyclophilin (NcCyP) | Amount administered to mice at a time, ul |
|---|---|---|---|---|
| T01 | QCDCRT | Quil-A (250 ug/2 ml), Cholesterol (250 ug/2 ml), DDA (100 ug/2 ml), Carbopol (0.075% v/v/2 ml), R1005 (1,000 ug/2 ml), CpG (SEQ ID NO: 8; 250 ug/2 ml) | (100 ug/2 ml dose) | 100 |
| T02 | TXO | CpG (SEQ ID NO: 8; 250 ug/2 ml), DEAE-Dextran (100 mg/2 ml), Mineral oil (50% v/v/2 ml), SPAN (1.5% v/v/2 ml), TWEEN 80 (7% v/v/2 ml) | NcCyP (100 ug/2 ml dose) | 100 |
| T03 | TCMO | CpG (SEQ ID NO: 8; 250 ug/2 ml), Mineral oil (50% v/v/2 ml), SPAN (1.5% v/v/2 ml), TWEEN 80 (7% v/v/2 ml), MPLA (25 ug/2 ml) | NcCyP (100 ug/2 ml dose) | 100 |
| T04 | QCDCRTc | Quil-A (250 ug/2 ml), Cholesterol (250 ug/2 ml), DDA (100 ug/2 ml), Carbopol (0.075% v/v/2 ml), R1005 (1,000 ug/2 ml), with "Tc" = Chimeric-ODN/ORN SEQ ID NO: 14 (250 ug/2 ml) | NcCyP (100 ug/2 ml dose) | 100 |
| T05 | ISCX | ISC = ISCOM (100 ug/2 ml), DEAE-Dextran (100 mg/2 ml) | NcCyP (100 ug/2 ml dose) | 100 |
| T06 | Negative Control | Normal saline | N/A | N/A |

The properties of the treatment groups above are summarized in Table 24.

TABLE 24

| | Splenocytes, stimulation index (mean +/− SEM) | IFNg production by Splenocytes (pg/ml) (mean +/− SEM) | Total IgG, OD at 1:16000 (mean +/− SEM) | IgG2a, OD at 1:2000 (mean +/− SEM) | IgG1, OD at 1:2000 (mean +/− SEM) |
|---|---|---|---|---|---|
| T01 (QCDCRT) | 8.0 +/− 7.0 | 23.0 +/− 15.3 | 0.2076 +/− 0.0547 | 0.6155 +/− 0.264 | 0.3823 +/− 0.03145 |
| T02 (TXO) | 62.9 +/− 59.0 | 680.5 +/− 446.7 | 0.279 +/− 0.06855 | 0.6742 +/− 0.192 | 0.7675 +/− 0.08285 |
| T03 (TCMO) | 92.1 +/− 46.4 | 961.5 +/− 205.5 | 0.2722 +/− 0.0581 | 0.6217 +/− 0.3393 | 0.972 +/− 0.199359048 |
| T04 (QCDCRTc) | 2.2 +/− 0.9 | 18.1 +/− 15.0 | 0.10780 +/− 0.01125 | 0.2584 +/− 0.03315 | 0.4404 +/− 0.0693 |
| T05(ISCX) | 5.4 +/− 3.6 | 84.4 +/− 49.4 | 0.1313 +/− 0.018 | 0.2255 +/− 0.0206 | 0.6486 +/− 0.23585 |
| T06(Control) | 1 +/− 2 | 12.0 +/− 7.3 | 0.0778 +/− 0.0033 | 0.18127 +/− 0.00959 | 0.22 +/− 0.012 |

Taken together, these data demonstrate superior results obtained using TXO and TCMO.

Example 7. The Effects of Different Adjuvants on Immune Responses to Reproductive Tract Infection with *Chlamydophila abortus*

*C. abortus* is an intracellular bacterium causing abortion in sheep and goats. Infection generally occurs during exposure of naTve ewes to aborted material (e.g., placenta, fluids, fetus). The bacterium bay be latent in infected ewes until breeding and during mid- or late gestation, it is present in placenta and causes necrotizing placentitis even despite antibody response. After the abortion, ewes are typically immune to reinfection.

It is believed that vaccination can be beneficial before exposure as it prevents the initial infection and prevents homing of the bacteria to placenta. Higher IFNg associated with the antibody response in post-abortion immunity is a key correlate of protection. IFNg may also be associated with persistence seen in the non-pregnant ewes.

Ewes were vaccinated on days zero and 28 and challenged on day 49. Animals were sacrificed on day 63 and necropsy was conducted. On day zero, vaginal and whole blood samples were taking for qPCR. Blood was sampled weekly for serology results and on days zero, 7, 28, and 35 for cytokines and Elispot measurements.

Treatment groups are presented in Table 25.

TABLE 25

| Group | Adjuvant | Composition |
|---|---|---|
| A | TCMYO | CpG (SEQ ID NO: 8, 100 ug/ds), Cholesterol (100 ug/ds), MPLA (100 ug/ds), Poly I:C (50 ug/ds) thickened with 45% mineral oil with 6.3% SPAN ® 80 and QS with TWEEN ® 80 (1.45%) and water |
| B | TCXMO | CpG (SEQ ID NO: 8, 100 ug/ds), Cholesterol (100 ug/ds), MPLA (100 ug/ds), DEAE-Dextran (100 mg/ds), thickened with 45% mineral oil with 6.3% SPAN ® 80 and QS with TWEEN ® 80 (1.45%) and water |
| C | TCMO | CpG (SEQ ID NO: 8, 100 ug/ds), Cholesterol (100 ug/ds), MPLA (100 ug/ds) thickened with 45% mineral oil with 6.3% SPAN ® 80 and QS with TWEEN ® 80 (1.45%) and water |
| D | No adjuvant (saline) | Normal saline |
| E | No vaccination | N/A |
| F | No infection or vaccination | N/A |

The antigen was prepared from an aborted ovine fetus kidney and propagated on McCoy cells. Elementary bodies were purified by centrifugation and sonication. The antigen was fixed at 100 ug/dose in 0.1% formaldehyde in 0.9% sodium chloride for vaccination.

TABLE 26

| Group | Avg. OD on day: 0 | 7 | 14 | 28 | 35 | 42 | 49 | 56 | 63 |
|---|---|---|---|---|---|---|---|---|---|
| A | 0.055 | 0.090 | 0.060 | 0.192 | 0.266 | 0.374 | 0.314 | 0.315 | 0.395 |
| B | 0.015 | 0.052 | 0.073 | 0.137 | 0.204 | 0.234 | 0.234 | 0.364 | 0.460 |
| C | 0.057 | 0.075 | 0.065 | 0.217 | 0.347 | 0.494 | 0.481 | 0.487 | 0.584 |
| D | 0.040 | 0.079 | 0.074 | 0.034 | 0.079 | 0.078 | 0.074 | 0.044 | 0.109 |
| E | 0.042 | 0.082 | 0.056 | 0.022 | 0.038 | 0.032 | 0.039 | 0.008 | 0.170 |
| F | 0.051 | 0.095 | 0.055 | 0.016 | 0.033 | 0.029 | 0.038 | 0.015 | 0.033 |

Serology results were obtained using Chek-it ELISA kit and are summarized in Table 26 above.

IFNg, IL-2 and IL-4 expression levels in Sheep PMBC stimulated with *Chlamydia* AG were determined. The results are in Table 27.

TABLE 27

IFNg, IL-2 and IL-4 expression levels in Sheep PMBC stimulated with *Chlamydia* AG

| Group | IFNg Day 7 | Day 28 | Day 35 | IL-2 Day 7 | Day 28 | Day 35 | IL-4 Day 7 | Day 28 | Day 35 |
|---|---|---|---|---|---|---|---|---|---|
| A | 18.08 | 4.20 | 10.77 | 4.79 | 7.62 | 8.53 | 3.26 | 3.01 | 1.53 |
| B | 1.67 | 2.05 | 2.52 | 4.08 | 7.35 | 5.63 | 2.26 | 1.12 | 3.24 |
| C | 1.39 | 1.77 | 2.61 | 1.18 | 1.78 | 8.09 | 1.48 | 0.94 | 1.09 |
| D | 1.58 | 4.58 | 2.70 | 0.87 | 2.73 | 3.27 | 0.64 | 1.27 | 1.24 |
| E | 2.52 | 2.42 | 2.14 | 2.53 | 1.95 | 1.68 | 1.44 | 1.38 | 1.35 |
| F | 0.83 | 1.20 | 2.05 | 0.74 | 3.13 | 3.71 | 1.91 | 2.11 | 1.47 |

Response of Ovine PBMCs to *Chlamydia abortus* antigen is summarized in Table 28.

TABLE 28

Response of Ovine PBMCs to *Chlamydia abortus* antigen

| Group | Mean SFC × $10^6$ cells Day 0 | Day 28 | Day 35 | Fold Increase Day 0 | Day 28 | Day 35 |
|---|---|---|---|---|---|---|
| A | 20.5 | 50.0 | 97.0 | 1.0 | 12.1 | 19.5 |
| B | 7.5 | 38.0 | 14.0 | 1.0 | 26.8 | 14.0 |
| C | 1.0 | 13.0 | 33.5 | 1.0 | 12.8 | 28.8 |

TABLE 28-continued Response of Ovine PBMCs to *Chlamydia abortus* antigen

| | Mean SFC × 10⁶ cells | | | Fold Increase | | |
|---|---|---|---|---|---|---|
| Group | Day 0 | Day 28 | Day 35 | Day 0 | Day 28 | Day 35 |
| D | 31.0 | 49.5 | 33.5 | 1.0 | 33.8 | 33.8 |
| E | 15.5 | 19.5 | 6.0 | 1.0 | 2.3 | 0.7 |
| F | 10.0 | 7.0 | 6.0 | 1.0 | 0.8 | 0.4 |

In addition, the amount of white blood cells was analyzed (data not shown). A 2-way ANOVA indicates that Group F had significantly higher WBC amount than Group A and B and that Group E had significantly higher WBC amount than Group B.

Nodules at the injection times were also analyzed. As expected, Groups A-C had bigger nodules than Groups C-D. Among the three adjuvant used (Groups A-C), Group C had the biggest nodule size, followed by Group B, followed by Group A.

The volume of nodules was determined. Again, groups A-C had greater nodule volumes than group D-F. Among groups A-C, Group A had the smallest volume. The nodules in Groups A and B had more hemorrhaging and/or nectrotic tissue. The nodules in Group C had more fibrosis. Cellular characteristics are similar in all three nodules, though Group C may have more lymphocytic component.

Example 8. Addition of Aluminum to TXO Results in an Improved Stability

The current TXO blend formulation contains 50 mg/ml of DEAE Dextran. Dextran, when present at high concentrations in subcutaneous injections, can cause injection site reactions in the animals. Hence it is proposed to try varying concentrations for DEAE Dextran to check if safety and good therapeutic value can be obtained without compromising the stability of the vaccine formulation.

Characterization and stability tests are important as they inform us whether this vaccine can be formulated consistently and with a good shelf life for manufacturing. Viscosity tests are performed at a range of shear rates in order to look for shear thinning (drop in apparent viscosity as shear rate goes up) or shear thickening (increase in apparent viscosity as shear rate goes up), which is a flow characteristic of Non-Newtonian fluids. Syringe force tests are performed to ensure that the vaccine will be easy to draw out and easy to administer over a large number of doses in the field.

Since the immunostimulating oligonucleotide is not expected to alter the stability of the formulation, it was not added to the adjuvant mixtures in this example. AXO (Aluminum+Dextran+Oil) blends of varying REHYDRA-GEL® (5% to 16%) and DEAE Dextran (50 mg/ml-10 mg/ml) concentrations are formulated tested for viscosity, syringe force and settling using an XO (Dextran+Oil) blend as a control. The tested compositions were as follows:

Approximately 10 ml of sample was filled into each of five 15-ml Corning centrifuge tubes and left still over a week in order to observe an accelerated settling effect on the emulsions due to the tubes' narrow dimensions and conical bottom. The samples were also tested for syringeability and viscosity. The results are shown below.

TABLE 29

| | | Aqueous Phase | | | Organic phase | |
|---|---|---|---|---|---|---|
| LOT | DEAE Dextran | REHYDRAGEL® 2% w/v Al₂O₃ | TWEEN80 | 10 mM PBS | Mineral Oil | SPAN 80 |
| 124008-65 | 50 mg/ml | 0 | 1.45% v/v | q.s | 45% v/v | 6.3% v/v |
| 124008-95 | 50 mg/ml | 5% v/v | 1.45% v/v | q.s | 45% v/v | 6.3% v/v |
| 124008-83 | 20 mg/ml | 10% v/v | 1.45% v/v | q.s | 45% v/v | 6.3% v/v |
| 124008-89 | 10 mg/ml | 16% v/v | 1.45% v/v | q.s | 45% v/v | 6.3% v/v |

These data indicate that upon subjection to accelerated settling in the centrifuge tubes, the blend with 16% REHYDRAGEL® is the most stable. Further, from previous work by the inventors, it was known that higher DEAE Dextran concentration is associated with higher viscosities and possible shear thinning. The results of these experiments indicate that the addition of REHYDRAGEL® more than compensates for anticipated loss in the shear thinning (pseudoplastic) properties afforded by DEAE Dextran. It was also observed that even though the 16% REHYDRAGEL® formulation had a higher syringe force, it was not noticeably harder to inject (syringe force for water is 3N).

TABLE 30

| Lot | Viscocity (cP) | Syringe Force (Newtons) | Settling observations (Day 7) |
|---|---|---|---|
| 124008-65 | 180 | 6.5 | Thin layer of aq. Phase observed at top |
| 124008-95 | 160 | 6.5 | Slight settling observed |
| 124008-83 | 180 | 6.5 | Thin layer of aq. Phase observed at top |
| 124008-89 | 180 | 7.5 | No Settling observed |

From the overall data, it is apparent that the blend with 16% REHYDRAGEL® and 10 mg/ml DEAE Dextran is optimal for use in vaccine formulations, particularly those requiring binding of free endotoxin and/or where longer emulsion shelf-life may be desired.

Example 9. BRV, BCV, and *E. coli* Antigens

In this example, the inventors research the use of adjuvants of the instant invention in vaccines against enteritis. Enteritis is caused by bacterial, viral and/or parasitic infections. Cattle, particularly, newborn dairy and beef calves are vulnerable to calf scours because they are subject to many stresses during the first few hours of life when their immune systems aren't fully developed. Fluid loss due to calf scours results in dehydration and often, death. Animals that survive calf scours often remain weak and perform poorly throughout their lives. Agents associated with scours include bacteria, particularly *E. coli* K99 and F41, and viruses, such as Bovine Coronavirus (BCV) and Bovine Rotavirus (BRV).

Ten-month old Holstein steers were used in this study. The animals were seronegative or low tittered for *E. coli* (K99 and F41), BRV (B223 and Lincoln) and BCV.

Treatment groups were as follows:

TABLE 31

| Group | N | Antigen | Adjuvant | Amounts per dose | Rt | Volume (ml) |
|---|---|---|---|---|---|---|
| T01 | 10 | Saline | N/A | NA (Commercial product) | SQ | 2 |
| T02 | 10 | ROTAVEC ® (*E coli* K99, BRV G6 and BCV | Mineral Oil + Alum | NA (Commercial product) | IM | 2 |
| T03 | 10 | *E. coli* K99/F41; BRV G6/G10, BCV (all inactivated) | Quil A + Cholesterol + REHYDRAGEL ®(15% v/v, 2% Al$_2$O$_3$ w/v) + CpG (SEQ ID NO: 8) | Quil-A (500 ug/2.5 ml dose), Cholesterol (200 ug/2.5 ml dose), REHYDRAGEL ® (15% v/v), CpG (100 ug/2.5 dose ml) | SQ | 2.5 |
| T04 | 10 | | Quil A + Cholesterol + REHYDRAGEL ®(15% v/v, 2% Al$_2$O$_3$ w/v) + CpG (SEQ ID NO: 8) + AMPHIGEN ® | Quil-A (500 ug/2.5 ml dose), Cholesterol (200 ug/2.5 ml dose), REHYDRAGEL ® (15% v/v), CpG (100 ug/2.5 ml dose), Amphigen (2.5% v/v) | SQ | 2.5 |
| T05 | 10 | | TXO + REHYDRAGEL ® (15% v/v, 2% Al$_2$O$_3$ w/v) | CpG (100 ug/5 ml dose), DEAE-Dextran (100 mg/5 ml dose), Mineral Oil (45% v/v), Span (6.3%), Tween (1.45% v/v) | SQ | 5 |
| T06 | 10 | | TO + REHYDRAGEL ® (15% v/v, 2% Al$_2$O$_3$ w/v) | CpG (100 ug/5 ml dose), Mineral Oil (45% v/v), Span (6.3%), Tween (1.45% v/v), REHYDRAGEL ®(15%) | SQ | 5 |

Blood samples were collected every 21 days for six months for serology. Injection site reactions were measured at Days 0 (pre-vaccination), 1, 2, 3, 7, 14, 21 and every 21 days thereafter. Responses to *E. coli* K96, *E. coli* F41, BRV Lincoln, BRV B223 and BCV were measured by quantifying antibody titers on selected days. The results are summarized below (different letters indicate differences at $\alpha$=0.1):

TABLE 32

| | Mean geometric titers against viruses (LSM) | | | | | | | | |
|---|---|---|---|---|---|---|---|---|---|
| | BRV G6 (Lincoln) Target titer >1255 | | | BRV G10 (B223), Target titer >1472 | | | BCV, Target titer >1107 | | |
| | Day 0 | Day 21 | Day 189 | Day 0 | Day 21 | Day 189 | Day 0 | Day 21 | Day 189 |
| T01 | 142.1 $^b$ | 208.1 $^a$ | 152.3 $^a$ | 430.5 $^a$ | 512.1 $^a$ | 588.5 $^a$ | 238.9 $^a$ | 430.6 $^a$ | 548.8 $^a$ |
| T02 | 129.2 $^b$ | 750.5 $^b$ | 349.9 $^b$ | 530.1 $^b$ | 1024.2 $^b$ | 675.7 $^{ab}$ | 349.8 $^b$ | 5997.1 $^b$ | 1398.9 $^b$ |
| T03 | 140.2 $^b$ | 3649.6 $^c$ | 533.9 $^b$ | 532.2 $^a$ | 2681.9 $^c$ | 985.6 $^{ab}$ | 348.4 $^{ab}$ | 7299.1 $^{bc}$ | 1106.1 $^b$ |
| T04 | 91.4 $^{ab}$ | 3128.8 $^c$ | 575.0 $^b$ | 492.7 $^a$ | 3511.8 $^{cd}$ | 1064.3 $^b$ | 298.8 $^{ab}$ | 7023.0 $^{bc}$ | 1448.3 $^b$ |
| T05 | 81.8 $^{ab}$ | 4705.6 $^c$ | 1498.9 $^c$ | 494.6 $^a$ | 9089.6 $^e$ | 2998.6 $^c$ | 326.3 $^{ab}$ | 10085.5 $^c$ | 2521.6 $^c$ |
| T06 | 39.1 $^a$ | 2682.1 $^c$ | 4706.4 $^d$ | 456.2 $^a$ | 6020.2 $^{de}$ | 4683.8 $^c$ | 237.2 $^a$ | 9556.2 $^c$ | 2298.9 $^c$ |

Treatments T05 and T06 resulted in the highest antibody titers from day 21 until the end of the study (day 189). Notably, commercial vaccine (ROTAVEC®) did not perform as well as T05 and T06 in inducing antibodies against the viral components of enteritis.

TABLE 33

Mean geometric titer of anti-E coli

| Group | E coli K99 pilus antigen (Target >742) | | | | E coli F41 pilus antigen (Target undetermined) | | | |
|---|---|---|---|---|---|---|---|---|
| | Day 0 | Day 21 | Day 106 | Day 189 | Day 0 | Day 21 | Day 106 | Day 189 |
| T01 | 35 $^a$ | 36 $^a$ | 82 $^a$ | 44 $^a$ | 187 $^a$ | 152 $^a$ | 142 $^a$ | 66 $^a$ |
| T02 | 41 $^a$ | 349 $^b$ | 4386 $^c$ | 2986 $^c$ | 152 $^a$ | 12801 $^c$ | 6970 $^d$ | 4223 $^e$ |
| T03 | 43 $^a$ | 588 $^{bc}$ | 686 $^b$ | 467 $^b$ | 200 $^a$ | 3200 $^b$ | 467 $^b$ | 200 $^b$ |
| T04 | 50 $^a$ | 588 $^{bc}$ | 1089 $^b$ | 686 $^b$ | 147 $^a$ | 3734 $^b$ | 800 $^b$ | 400 $^{cd}$ |
| T05 | 50 $^a$ | 1056 $^d$ | 3200 $^c$ | 2986 $^c$ | 264 $^a$ | 12801 $^c$ | 1600 $^c$ | 607 $^d$ |
| T06 | 54 $^a$ | 864 $^{cd}$ | 3456 $^c$ | 1601 $^c$ | 216 $^a$ | 1600 $^b$ | 800 $^b$ | 234 $^{bc}$ |

Treatments T02 and T05-T06 performed similarly well in eliciting response against K 99. Treatment T02 elicited the best response to *E. coli* F41. Treatment T05 was the second most effective in eliciting response to that antigen.

Taken together, these data demonstrate that T05 and T06 appear to be the most promising formulations. Both have delivered target IgG responses for multiple fractions through day 189. Both T05 and T06 appear to provide superior or equivalent serological efficacy compared to ROTAVEC® (T02, IM) by SQ administration. T03 and T04 retained elevated serological titers for the shorter duration than T05 and T06. With a single dose vaccination T03, T04, T05 and T06 delivered above the target level serum titers for BRV G6, BRV G10 and BCV. With a single dose vaccination T04, T05 and T06 delivered above the target level serum titers for *E. coli* K99. T04, T05 and T06 retained anti-virus serum titers above the target levels for 6 months. T05 and T06 retained anti-*E. coli* K99 serum titers above the target levels for 6 months. All formulations evaluated have demonstrated adequate safety in Holstein steers.

Rectal temperatures were measured on days zero, 1, 2, and 3. While there were statistically significant differences between group T01 (control) and groups T02-T06, the differences in temperatures (LSM) were not great (within one degree F.).

TABLE 34

| | Day 000 | Day 001 | Day 002 | Day 003 |
|---|---|---|---|---|
| T01 | 101.1 $^a$ (38.4) | 102.2 $^{ab}$ (39.0) | 102.0 $^a$ (38.9) | 102.3 $^b$ (39.1) |
| T02 | 101.7 $^b$ (38.7) | 102.6 $^{abc}$ (39.2) | 102.2 $^{ab}$ (39.0) | 101.8 $^a$ (38.8) |
| T03 | 101.8 $^b$ (38.8) | 102.7 $^{bc}$ (39.3) | 102.2 $^{ab}$ (39.0) | 101.9 $^a$ (38.8) |
| T04 | 101.3 $^{ab}$ (38.5) | 102.8 $^c$ (39.3) | 102.0 $^a$ (38.9) | 102.0 $^{ab}$ (38.9) |
| T05 | 101.7 $^b$ (38.7) | 102.3 $^{abc}$ (39.1) | 102.5 $^b$ (39.2) | 102.4 $^b$ (39.1) |
| T06 | 101.6 $^{ab}$ (38.7) | 102.1 $^a$ (38.9) | 102.4 $^b$ (39.1) | 102.1 $^{ab}$ (38.9) |

Preliminary testing of formulations in pregnant dairy cows has demonstrated safety. Groups T01, T03 and T05 were tested, 5 cows in each group. Thirteen of 15 cows have calved, 12 calves were normal, one was stillborn.

Example 10. Anti-Tick Vaccine

Experiment Design

Two vaccine formulations based on the Bm86 antigen were tested. One formulation contained an aqueous adjuvant (QCDCRT) and the other an oil-based adjuvant (TXO), as summarized below.

TABLE 35

| Group | Antigen | Adjuvant (80% volume) | Amounts of ingredients |
|---|---|---|---|
| T01 | N/A | None | N/A |
| T02 | *Rhipicephalus microplus* (formerly *Boophilus*) purified rBm86 protein (stock, 1.16 mg/ml) | QCDCRT | 250 ug Quil-A, 250 ug Cholesterol, 100 ug DDA, 0.0375% Carbopol, 1,000 ug R1005, 100 ug SEQ ID NO: 8 |
| T03 | | TXO | 100 ug SEQ ID NO: 8/ 100 mg DEAE-Dextran in mineral oil (45%), SPAN ® 80(6%) & TWEEN ® 80 (1.45%) |

Since the adjuvants were used at 80% volume, as described above, one dose of the vaccine composition administered to group T03 contained 100 ug SEQ ID NO: 8/100 mg DEAE-Dextran, 36% v/v of mineral oil, 4.8% v/v SPANe80, and 1.16% v/v TWEEN® 80. Since there was no oil in QCDCRT, the concentrations of the ingredients were the same as in Table 35.

Twenty-four calves were randomly assigned into one of three treatment groups of eight calves each. The calves of each treatment group were individually vaccinated with 2 cc of either one of the two Bm86+adjuvant formulations or saline (control group). Vaccinations occurred on day 0 and 28. On day 41, the cattle were placed into stanchion, and on day 42 were infested with 250 mg of *R. annulatus* larvae. The ticks used in this study were originally collected from a ranch in Val Verde County, Tex. All detaching engorged adult females were collected daily from individual calves on days 63-84. Calves were removed from stanchion on day 85. Collected ticks were counted and up to 10 from each calf were weighed and placed into an environmental chamber each day of collection for 13 days. Spent females were discarded 14 days after collection and the egg mass produced weighed. Fourteen days after the first hatch, the numbers of hatched and intact eggs were recorded and a determination of percent hatch was calculated. Before each injection with vaccine and for the following three days post injection, the injection site was monitored on each calf for lumps, and rectal temperatures were taken. Blood serum was collected from each calf on days −7, 0, 14, 28, 42, and 85 for the determination of Bm86 antibody titers throughout the study as determined by ELISA. Results Preliminary results show 98.6 and 99.6% control from T02 and T03 formulations, respectively, which is significantly higher than T01. These percent control calculations take into account only the reduction in engorged females and egg mass weight. Reduction in percent hatch will be determined at a later date and added to the final results. One of the 24 calves in the study produces a small lump after each injection (formulation containing the oil adjuvant). The lumps are less than 10 cm in length and 3 cm in depth. Lumps are soft and do not seem painful to the animal. There are no increases in rectal temperature from the treated animals throughout the study.

Serology results demonstrate statistically significant differences between each of the treatments on the respective time points except there was no statistical significance (p=0.114) between treatments with QCDCRT and TXO at 14 days time point. Both QCDCRT and TXO effectively increase BM86 antibody titers at each time point tested. TXO was superior to QCDCRT (p<0.05) at each time point tested except on day 14 (p=0.114).

TABLE 36

BM86 antibody titer, Back Transformed Least Square mean (Mean ± SEM)

| Group | N | Day 14 | Day 28 | Day 41 | Day 83 |
|---|---|---|---|---|---|
| T01 | 8 | 100 ± 46.42 | 100 ± 31.52 | 100 ± 17.05 | 100 ± 17.31 |
| T02 | 8 | 2018 ± 937 | 1179 ± 372 | 13532 ± 2308 | 4082 ± 707 |
| T03 | 8 | 5956 ± 2765 | 8404 ± 2649 | 28557 ± 4870 | 18638 ± 3227 |

Example 11. Foot-and-Mouth Disease (Guinea Pigs)

The goal of this study was to compare the humoral immune responses in guinea pigs vaccinated with trivalent FMD vaccines adjuvanted with different adjuvant formulations. Guinea pigs were vaccinated on days zero and 28 as summarized in Table 37.

In each dose of T03-T07, the antigen was a combination of FMVD Type O (9 ug), A (5 ug) and Asia1(5 ug/ml). Antigen composition in T02 is proprietary information of the manufacturer and thus was unavailable.

Blood samples were collected for serology study on days −3, 25, and 53. Serum titers of antibodies against serotypes O, A, and Asia 1 are summarized below.

While the responses against Sero types O and A were low even in positive control group (T02), the response against Asia 1 were higher in T07 (TXO adjuvant) than in the positive control group, and greater than in any other treatment. The low responses against serotypes O and A may be die to presence of low levels of O and A antigens in the formulation.

Notably, liposome-based VACCIMAX® groups (T03-T05) did not demonstrate significant response against any of the antigens (O, A, Asia1).

TABLE 37

| Group | N | Adjuvant/Ingredients | | Treatment days | Dose | RT |
|---|---|---|---|---|---|---|
| T01 | 24/22 | Saline | | 0, 28 | 0.2 ml | IM |
| T02 | 24/24 | Commercial vaccine- Raksha Monovalent FMDV vaccine (vet) (positive control) | Proprietary | 0, 28 | 0.2 ml | IM |
| T03 | 23/22 | VACCIMAX® S100/polyI: C | S100/Cholesterol, 12% w/v (60 mg/dose)/Poly I:C 100 µg/dose Water in Oil, 50% aqueous liposomes + 50% Marcol 52/ Montanide 888 | 0, 28 | 0.2 ml | IM |
| T04 | 23/23 | VACCIMAX® S100/Pam3Cys | Proprietary | 0, 28 | 0.2 ml | IM |
| T05 | 23/22 | VACCIMAX® (Biolipon 95)/ Pam3Cys | VacciMax Biolipon 95, 100 ug/ Poly I:C/ds, Water in Oil, 50% aqueous liposomes + 50% Marcol 52/ Montanide 888 | 0, 28 | 0.2 ml | IM |
| T06 | 24/24 | QCDCRT (80% volume) | 250 ug Quil-A, 250 ug Cholesterol, 100 ug DDA, 0.0375% Carbopol, 1,000 ug R1005, 100 ug SEQ ID NO: 8 | 0, 28 | 0.2 ml | IM |
| T07 | 24/23 | TXO (80% volume) | 100 ug SEQ ID NO: 8; 100 mg Dextran DEAE, 45% mineral oil, 6.3% SPAN®80, 1.45% TWEEN®80, QS water | 0, 28 | 0.2 ml | IM |

N represents the number of animals surviving for the first/second vaccination

Since adjuvants TXO and QCDCRT were used at 80% volume, as described above, one dose of the vaccine composition administered to group T07 contained 100 ug SEQ ID NO: 8/100 mg DEAE-Dextran, 36% v/v of mineral oil, 5.04% v/v SPAN® 80, and 1.16% v/v TWEEN® 80. Since there was no oil in QCDCRT, the concentrations of the ingredients were the same as in Table 37.

TABLE 38

| Group | Sero Type O SN titers, Geometric mean titer | | | Sero Type A SN titers, Geometric mean titer | | | Sero Type Asia1 SN titers, Geometric mean titer | | |
|---|---|---|---|---|---|---|---|---|---|
| | Day −3 | Day 28 | Day 56 | Day −3 | Day 28 | Day 56 | Day −3 | Day 28 | Day 56 |
| T01 | 4 | 4 | 4.1 | 4 | 4 | 4 | 4 | 4.1 | 4.1 |
| T02 | 4 | 9.6 | 49.9 | 4 | 7 | 14.1 | 4 | 14 | 266.9 |
| T03 | 4 | 4.8 | 13.8 | 4 | 4.1 | 9 | 4 | 5.9 | 24.3 |
| T04 | 4 | 4.1 | 10.3 | 4 | 4.5 | 5.8 | 4 | 4.3 | 9.7 |
| T05 | 4 | 4.1 | 8.1 | 4 | 4.5 | 4.7 | 4 | 4.3 | 13.6 |
| T06 | 4 | 4.1 | 5 | 4 | 4 | 4 | 4 | 4.2 | 5.1 |
| T07 | 4 | 5 | 9 | 4 | 5.6 | 43.1 | 4 | 19.8 | 320.8 |

Example 12. Foot-and-Mouth Disease (Cattle)

In this study, the effect of different adjuvants used in a vaccine against FMD in a challenge model was determined. Three adjuvants were studied. The vaccine was an ARS experimental vaccine against FMD in a challenge model developed by PIADC. FMD-LL3B3D-A24 Cruzeiro was used both as the antigenic component of the vaccine (10 ug) and wild type FMDV A-24 Cruzeiro was used as the challenge virus. The antigen was previously described e.g., in US20120315295 (Rieder at al, filed on Jun. 9, 2011 and published on Dec. 13, 2012). Briefly, FMD-LL3B3D-A24 Cruzeiro comprises a genetically modified FMDV (Foot-And-Mouth-Disease Virus). The FMDV is genetically modified, i.e., it is a leaderless virus containing a deletion of the leader ($L_{pro}$) protein coding region such that FMD viruses lacking this protein are attenuated in cattle and pigs. It also comprises mutations (negative markers) introduced in two non-structural viral proteins resulting in the elimination of two antigenic epitopes recognized by specific antibodies, one located in protein 3B and the other in protein 3D (replaced by the corresponding sequence of bovine rhinovirus that serves as negative antigenic epitope in these proteins), thus providing two possible targets for DIVA (Differentiation of naturally Infected from Vaccinated Animals) serological tests.

Four to seven bovines were used in each group. Total volume injected was 2 ml. Animals were vaccinated on day zero by an IM injection (2.0 ml per dose) and challenged on day 21 by intra-dermal route with wild type FMDV. Clinical scores were assessed on days 0, 3, 7, and 10 according to the following scale: no clinical signs: 0, vesicular foot lesions: 1 point for each foot affected. Maximum score is 4. The results of the experiment are as follows:

TABLE 39

| | | | Average clinical score | | | |
|---|---|---|---|---|---|---|
| Group | Adjuvant | Details/Per dose | Day 0 | Day 3 | Day 7 | Day 10 |
| T01 | Saline | N/A | 0 | 3.0 | 3.5 | 4.0 |
| T02 | MONTANIDE ® ISA 206 VG | A mineral oil based adjuvant which has been developed for the manufacture of Water-in-Oil-in-Water (W/O/W) emulsions. It comprises a high grade injectable mineral oil and an extremely refined emulsifier obtained from mannitol and purified oleic acid of vegetable origin. MONTANIDE ® ISA 206 VG is free of animal origin ingredients. The exact composition is proprietary to manufacturer (Seppic Inc) | 0 | 0 | 0 | 0 |
| T03 | QCDCRT (80% volume) | 250 ug Quil-A, 250 ug Cholesterol, 100 ug DDA, 0.0375% Carbopol, 1,000 ug R1005, 100 ug SEQ ID NO: 8 | 0 | 1.14 | 2.86 | 2.43 |
| T04 | TXO (80% volume) | 100 ug SEQ ID NO: 8/100 mg DEAE-Dextran in WO emulsion | 0 | 0 | 0 | 0 |

Differences between T01 and T02 and between T01 and T04 were statistically significant.

From the table above, it can be concluded that at least based on the clinical score, adjuvants TXO and MONTANIDE® ISA 206 VG are about equally efficient. However, serology analysis to measure serum neutralizing activity against FMDV-A24 demonstrates that group T04 (adjuvant TXO) had higher titers than group T02 (MONTANIDE® ISA 206 VG).

TABLE 40

Serum Neutralization titers Least Square Means (back-transformed)

| | Time point | | | |
|---|---|---|---|---|
| | Day 0 | Day 7 | Day 14 | Day 21 |
| T01 | $0.45^a$ | $0.45^a$ | $0.45^a$ | $0.45^a$ |
| T02 | $0.45^a$ | $1.60^c$ | $1.13^c$ | $1.20^b$ |
| T03 | $0.45^a$ | $1.10^b$ | $0.66^b$ | $0.61^a$ |
| T04 | $0.45^a$ | $2.21^d$ | $2.21^d$ | $2.21^d$ |

Different letters indicate statistically significant difference ($p \leq 0.05$)

These results demonstrate that TXO adjuvant was able to provide 100% protection against a challenge with a FMD causing agent in cattle and confer higher antibody titers than the saline control and the other two adjuvants tested.

The amount of FMDV RNA (copies per mL) was determined in nasal swabs and in serum. The data are provided in tables 41-44. Briefly, these data demonstrate that groups T02 and T04 resulted in lower amounts of FMDV in nasal swabs. Among T02 and T04, it is noted that animals in group T04 demonstrated earlier decrease (or lack of increase) in FMDV RNA amounts, thus again demonstrating superior properties of adjuvant TXO.

TABLE 41

FMDV in nasal swabs ("Shedding" FMDV RNA copy per ml measured by rRT-PCR; LS means)

Time Point

| | Day 21 | Day 22 | Day 23 | Day 24 | Day 25 | Day 26 | Day 27 | Day 28 | Day 29 | Day 30 | Day 31 |
|---|---|---|---|---|---|---|---|---|---|---|---|
| T01 | 1.35 | 1.75 | 6.16 | 7.09 | 6.88 | 6.13 | 5.19 | 4.98 | 2.51 | 1.81 | 1.35 |
| T02 | 1.35 | 1.49 | 4.63 | 5.31 | 5.62 | 4.14 | 2.21 | 1.84 | 1.58 | 2.66 | 1.83 |
| T03 | 1.35 | 1.92 | 3.54 | 4.66 | 5.39 | 5.27 | 3.12 | 1.87 | 1.56 | 1.84 | 1.84 |
| T04 | 1.35 | 1.59 | 3.97 | 5.05 | 4.47 | 3.75 | 2.31 | 1.61 | 1.56 | 2.58 | 1.55 |

TABLE 42

Statistical significance (nasal swabs)

$P \leq 0.05?$

| | Day 21 | Day 22 | Day 23 | Day 24 | Day 25 | Day 26 | Day 27 | Day 28 | Day 29 | Day 30 | Day 31 |
|---|---|---|---|---|---|---|---|---|---|---|---|
| T01 vs 102 | No | No | Yes | Yes | No | Yes | Yes | Yes | No | No | No |
| T01 vs 103 | No | No | Yes | Yes | No | No | Yes | Yes | No | No | No |
| T01 vs 104 | No | No | Yes | Yes | Yes | Yes | Yes | Yes | No | No | No |
| T02 vs 103 | No | No | No | No | No | No | No | No | No | No | No |
| T02 vs 104 | No | No | No | No | Yes | No | No | No | No | No | No |
| T03 vs 104 | No | No | No | No | No | Yes | No | No | No | No | No |

TABLE 43

FMDV in serum ("Viremia", FMDV RNA copy number per ml measured by rRT-PCR;

Time Point

| | Day 21 | Day 22 | Day 23 | Day 24 | Day 25 | Day 26 | Day 27 | Day 28 | Day 29 | Day 30 | Day 31 |
|---|---|---|---|---|---|---|---|---|---|---|---|
| T01 | 1.35 | 6.85 | 8.67 | 8.56 | 5.96 | 3.91 | 1.77 | 1.35 | 1.35 | 1.35 | 1.35 |
| T02 | 1.35 | 1.58 | 1.57 | 1.75 | 1.83 | 1.35 | 1.35 | 1.35 | 1.35 | 1.35 | 1.35 |
| T03 | 1.35 | 3.84 | 3.77 | 3.20 | 2.72 | 1.82 | 1.35 | 1.35 | 1.35 | 1.35 | 1.35 |
| T04 | 1.35 | 1.59 | 1.35 | 1.35 | 1.35 | 1.35 | 1.35 | 1.35 | 1.35 | 1.35 | 1.35 |

TABLE 44

Statistical significance (serum)

$P \leq 0.05?$

| | Day 21 | Day 22 | Day 23 | Day 24 | Day 25 | Day 26 | Day 27 | Day 28 | Day 29 | Day 30 | Day 31 |
|---|---|---|---|---|---|---|---|---|---|---|---|
| T01 vs 102 | No | Yes | Yes | Yes | Yes | Yes | Yes | No | No | No | No |
| T01 vs 103 | No | Yes | Yes | Yes | Yes | Yes | No | No | No | No | No |
| T01 vs 104 | No | Yes | Yes | Yes | Yes | Yes | Yes | No | No | No | No |
| T02 vs 103 | No | Yes | Yes | Yes | No | No | No | No | No | No | No |
| T02 vs 104 | No | No | No | Yes | Yes | No | No | No | No | No | No |
| T03 vs 104 | No | Yes | Yes | Yes | Yes | No | No | No | No | No | No |

While all animals in group T01 exhibited fever after the challenge, none of animals in group T04 had fever. The responses in groups T02 and T03 were inconsistent (some animals exhibited fever and some did not). This observation confirms the conclusion of general superiority of TXO compared to the other adjuvants used in this study.

Example 13: TXO Activates Cell-Mediated Immunity

Using FMD as an exemplary antigen in the animal model described in the previous example, the effect of the adjuvants on cell-mediated immunity was analyzed. Peripheral blood mononuclear cells (PBMC) were purified from bovine whole blood collected on days 4, 7, 14, and 21 post-vaccination. FMDV-specific T cell proliferative responses were assessed using Carboxyfluorescein Diacetate Succinimidyl Ester (CFSE) staining.

The results are provided in table 45.

TABLE 45

| Treatment/DAY | Proliferation index (Mean ± SD) | | | |
|---|---|---|---|---|
| | Day 4 | Day 7 | Day 14 | Day 21 |
| T01 | 1 ± 0 | 1.22 ± 0.365 | 1.12 ± 0.070 | 0.965 ± 0.144 |
| T02 | 1 ± 0 | 1.633 ± 1.046 | 1.813 ± 0.860 | 4.473 ± 4.012 |
| T03 | 1 ± 0 | 1.769 ± 0.877 | 1.850 ± .980 | 1.549 ± 0.608 |
| T04 | 1 ± 0 | 1.589 ± 0.682 | 2.667 ± 1.424 | 6.757 ± 4.653 |

These data demonstrate superior effect of TXO on cell-mediated immunity both at day 14 and day 21. These data also indicate that since cell-mediated immunity is responsible for duration off immunity, adjuvant TXO can possibly provide a longer duration of immunity than MONTANIDE® ISA 206 VG.

Example 14. Generation of Antibodies for Diagnostic Use

Adjuvant TXO of the instant invention was used to generate antibodies for diagnostic use. Briefly, source animals have been immunized every 2-4 weeks with formulations comprising selected recombinant antigens adjuvanted with TXO, the composition of which was as follows: SEQ ID NO: 8-125 ug; DEAE dextran—125 mg; Mineral oil—46.56% v/v of the formulation; TWEEN® 80-1.5% v/v of the formulation; SPAN® 80-6.518% v/v of the formulation.

The adjuvant formulation was used at 80% v/v of the vaccine composition. Accordingly, the final concentration of the components of adjuvant formulations was as follows: SEQ ID NO: 8-100 ug; DEAE dextran—100 mg; Mineral oil—37.248% v/v of the vaccine composition; TWEEN® 80-1.2% v/v of the vaccine composition; SPAN® 80-5.214% v/v of the vaccine composition. The final volume was 2 ml.

Small visible injection site reactions were observed after injections, but were within the anticipated size of reactions. Based on daily observations, the reactions observed over the ribs did not appear to be painful to the goats.

Blood samples were collected 2-3 weeks after each immunization, and various assays were run to evaluate antibody titer. Serology ELISA titer over 1000 was considered sufficient to start antibody harvesting.

The animals were bled weekly (7.5% of the blood volume based on body mass). At the conclusion of the study, goats were euthanized by terminal exsanguinations and that blood was also collected for antibody harvesting. If necessary or the animals were repurposed for additional studies.

TABLE 46

Summary of Completed Goat Polyclonal Reagent Generation Studies

| Antigen | Amount (ug)/dose | Source Animal (N) | Source of ABs | Total Serum Volume Collected | Immunizations, N | Comments |
|---|---|---|---|---|---|---|
| FeLV gp70 | 100-150 ug | Goat (6) | Serum, milk* | 26.7 L serum, 300 L milk | 15 | All goats achieved titer over 2000000# |
| *Histophilus somni* (*H. somni*) p31 protein | 150 ug | Goat (4) | Serum | 4.84 L | 8 | All goats achieved titer over 2500000. Two achieved titer over 5000000 |
| Bovine Parainfluenza-3 (BPI-3) HN protein | 61.8 ug | Goat (4) | Serum | 3.19 L | 4 | All goats achieved titer over 2000. Three goats achieved titer over 8000 |
| rBVD1 E2 (gp53) | 150 ug | Goat (4) | Serum | 3.93 L | 3 | All goats achieved titer over 100000. One goat consistently had titers over 1200000 |
| Canine Circovirus antigen | 150 ug | Goat (4) | Serum | 4.51 L | 4 | All goats achieved titer over 500000. Two achieved titer over 2000000 |
| *Bordetella* FHA protein | 100 ug | Goat (4) | Serum | 2.57 L | 4 | All goats achieved titer over 800,000. Two achieved titer over 4000000 |

TABLE 46-continued

Summary of Completed Goat Polyclonal Reagent Generation Studies

| Antigen | Amount (ug)/dose | Source Animal (N) | Source of ABs | Total Serum Volume Collected | Immunizations, N | Comments |
|---|---|---|---|---|---|---|
| Parapoxvirus (inactivated) | 150 ug | Goat (4) | Serum | 1.35 L | 6 | All goats achieved titer over 40000 |

*One goat in the group developed pseudo pregnancy and lactated. 300 L of milk was collected from this goat.
Titers deduced from the ELISA assays run. At that time endpoint titers were not indicated and the serum was not diluted out far enough to determine endpoint.

Serum antibodies for FeLV gp70 were successfully purified using either Protein A or Protein G columns in-house, for small scale purification, or Protein G chromatography for large scale purification, at Maine Biotechnology Services (MBS), Portland, Me. The polyclonal antibodies were concentrated using Millipore 30K Ultra Filter Units to a final concentration of about 1 mg/ml. Antibodies against the other antigens disclosed in table 46 were unpurified.

The antibodies were isolated from milk obtained from a spontaneously lactating goat immunized with FeLVgp70 according to a method comprising the following steps:

a) The pH of the milk was titrated to 4.6 with 2 M HCl and stirred at room temp for 30 minutes for casein precipitation;

b) The milk was centrifuged at 17,000×g for 30 minutes and the supernatant was collected;

c) Equilibration buffer was added to the supernatant to 3.3 M NaCl, 0.3 M glycine and 0.2 M Tris base;

d) The supernatant was clarified by centrifugation at 3000×g for 15 minutes;

e) The clarified milk supernatant was applied to a Mab-Select column equilibrated with the buffer in step 'c';

f) The column was washed with Equilibration buffer and eluted with 0.15M glycine pH3.0;

g) Elute fractions were neutralized with 0.2 M Na phosphate.

As non-limiting examples, methods of generating anti-PI-3 and anti FeLV gp70 are provided below.

One of the objectives was to generate goat polyclonal antisera to purified Bovine Parainfluenza-3 (BPI-3) HN protein for use in in-vitro assays. This study was designed to vaccinate goats with a purified Bovine Parainfluenza-3 (BPI-3) HN protein formulated with TXO adjuvant Bovine Parainfluenza-3 (BPI-3) HN protein used as the antigen.

At approximately seven weeks after the first injection, it was determined that all four of the goats had high enough serum antibody concentrations (SN over 1000) to begin production bleeds for serum. Production bleeds began one week after the fourth immunization. Blood was collected for serum at weekly intervals for three weeks. Serum from each goat was pooled for individual production bleeds. A total of 3,187.50 mL of serum was collected during approximately 3 weeks of production bleeds. Serum was processed and stored at −80° C. for evaluation in BPI-3 HN-based assays.

All serum collected from three goats (#30, 31 and 35) were thawed at room temperature. Serum from goat number 34 was not used due to the low antibody response in the screening ELISA. See Table 47 (PI3-NH Polyclonal antibody production: SN Response and antigen potency ELISA).

Goat number 35, collected 20 Nov. 13, had the lowest volume of available serum, 117 mL. Thus, 117 mL from each goat per collection was pooled in a sterile 1 L Nalgene PETG bottle. Approximately 1053 mL (9×117 mL) of serum was dispensed into 20, 50 mL aliquots in sterile 60 mL Nalgene PETG bottles and 50, 1.0 mL aliquots.

TABLE 47

| | Animal ID with PI3 SN titer | | | |
|---|---|---|---|---|
| Immunization | 30 | 31 | 34 | 35 |
| 0 | <2 | 76 | <2 | <2 |
| 1 | 215 | 1218 | 54 | 362 |
| 2 | 4096 | 8192 | 2435 | 9192 |
| 3 | 8192 | 16384 | 2696 | 9742 |

As a result, this study at completion successfully generated a total of 3,187.5 mL of whole blood harvested from four goats that were repeatedly immunized with a purified BPI-3 protein formulated with TXO, during a three week period of production bleeds. Good polyclonal antibody titers were generated in serum. Sufficient quantities of purified reagent were obtained to for use in in-vitro assay applications.

In 2010, USDA notified industry that the FeLV gp85/70 capture reagent used for LEUKOCELL® and VERSIFEL® assays would no longer be supplied. Thus, the objective of this study was to generate goat polyclonal antisera to recombinant FeLV gp70 protein for use in in-vitro assays.

Previous attempts to produce antibody following vaccination with Freund's adjuvant were not successful. This study was designed to vaccinate goats with a 444 amino acid fragment of recombinant E. coli-expressed FeLV gp70 protein formulated with adjuvant. Beginning with the 4th injection, the injection dose was reduced to 100 µg FeLV gp70 protein (instead of the original dose of 282 µg FeLV gp70 protein). The dose change was made because initial dose at 282 µg/mL was causing high incidence of injection site reactions. Dose was initially lowered to 100 µg/mL, but then raised to 150 µg/mL for the seventh immunization and remained at that level until the end of the study (total of 15 immunizations). PBS buffer was used to make up the difference in dose volume, which remained at 1 mL Blood was collected from the goats, and once antibody titers were determined by direct and sandwich ELISA assay to be sufficiently high, serum was harvested and polyclonal antibodies were purified.

Six healthy female goats of LaMancha and Alpine breeds that were 1-3 years of age and weighed >100 lbs were obtained for use in this study. Goats were fed hay and grain and had ad libitum access to water throughout the study. General health observations were performed once daily. A 1 mL dose of the experimental vaccine was administered subcutaneously to each goat at 21-day intervals, with a total of 15 immunizations administered to each of the five goats that completed the study. Immunizations were initially administered in the neck or rear leg, alternating sides and sites for subsequent immunizations. Small visible injection site reactions were observed following immunizations. The immunization, administered to goats in the loose skin just cranial of the right rear leg, was reported to cause a little swelling, tenderness, and moderate lameness in all goats the next day. Subsequent injections were administered in alternate sides of the neck or the area over the ribs and were generally well tolerated. However, the area over the ribs was ultimately found to be the location best tolerated by the goats.

At approximately eight weeks after the first injection it was determined that four of the six goats (21, 22, 24, 25) had high enough serum antibody concentrations to begin production bleeds for serum. Production bleeds from the remaining two goats (23, 26) were initiated five weeks later. Blood was collected for serum at weekly intervals. Goat 25 was removed from the study after six weeks of production blood collections. She was lame at arrival and displayed persistent lameness despite Banamine treatments. Euthanasia was specified for the terminal bleed and administered per site procedure, to ensure maximum blood volume collection. Serum from each goat was pooled for individual production bleeds. A total of 26.7 L of serum was collected during approximately 7 months of production bleeds.

Unexpectedly, Goat 24 developed a pseudo-pregnancy during the study. Milk was collected from this goat for >3 months, with a total of 300 L of milk available for antibody harvest. A protocol was developed for high-level purification of FeLV gp70 polyclonal antibody from the milk.

Antibodies were purified on two different dates from 500 mL of pooled serum from Goat 24 using Protein G Affinity Chromatography at Maine Biotechnology Services. A total of 6388 mg (321 mL of 19.9 mg/mL) and 7343 mg (348 ml of 21.1 mg/ml) of purified goat anti-FeLV gp70 antibodies were prepared for evaluation in FeLV-based assays.

Blood samples (approximately 25 mL/sample) were collected into 12.5 mL serum separatortubes (SST) fourteen days after each vaccination to determine antibody concentrations to FeLV gp70. SSTs were labeled with the goat ID and date of collection. Once assays determined that the FeLV gp70 antibody titers based on ELISA signal intensity for an animal was at an acceptable concentration, production collections began from that animal. The blood volumes extracted from each goat were determined on the basis of the goat's weight to obtain the maximum blood volume. IACUC guidelines allow for the collection of up to 7.5% of the blood volume weekly.

Blood was collected into 12.5 mL SST for production collections. At the conclusion of the study, goats were euthanized by terminal exsanguinations and that blood was also collected for antibody harvesting. All tubes were labeled with the goat's ID and the date of collection.

Blood was allowed to clot at room temperature. Following centrifugation, serum was harvested and transferred to polypropylene vials. Serum from different SST collected from the same goat on a collection day was pooled. Serum was held on ice until shipped for purification. A summary of production is provided in table 48.

TABLE 48

| Goat ID | Weekly Volumes (ml) | Terminal Bleed (ml) | Total production (ml) |
|---|---|---|---|
| 21 | 75-125 | 1000 | 4430 |
| 22 | 85-150 | 875 | 4665 |
| 23 | 85-125 | 1000 | 3630 |
| 24 | 110-200 | 1580 | 6785 |
| 25 | 80-105 | 980 | 1565 |
| 26 | 125-200 | 1750 | 6125 |
| Total | | | 26.7 L |

Goat 24 was producing serum with the highest antibody concentrations of all the goats.

Purified serum antibodies from Goat 24 compared to the USDA 94-06 as a capture reagent using the FeLV gp70 C11D8 detection mAb in a Sandwich ELISA assay showed a similar dose response. The purified serum from Goat 24 was compared to the USDA 94-06 reagent by Western Blot for the ability to detect the FeLV gp85/70 protein. A similar Western Blot profile was observed between the current capture, 94-06 and the new Goat 24 capture, except that an additional ~15 kD band was observed with the Goat 24 capture. Data using the new capture antibody showed that the current reference has a different dose response curve shape than the current reagent when used to capture the reference and the serial tested.

Both anrendati-FeLV gp70 purified from serum and milk functioned well as a capture reagent in the FeLV ELISA assays.

Additional studies are under way, as provided in Table 49. It is expected that each of the formulations (antigens disclosed in Table 49 and adjuvanted with TXO) would elicit sufficiently high serology titers (over 1000, or more preferably, over 5000, or more preferably, over 10000, or more preferably, over 50000, or more preferably, over 100000, or more preferably, over 250000, or more preferably, over 500000, or more preferably, over 1000000) in at least one animal (preferably at least 2 animals, or more preferably in at least three animals, or most preferably, in every animal treated) thus resulting in sufficient amount of antibodies for diagnostic or research applications.

TABLE 49

| Antigen | Amount (ug)/ dose | Source Animal (N) | Source of ABs | Total Serum Volume Collected | Immunizations, N |
|---|---|---|---|---|---|
| *Clostridium perfringens* Alpha toxin (inactivated) | 100 ug | Goat (3) | Serum | 3.31 L/ ongoing | 10 |
| *Clostridium perfringens* Beta toxin (inactivated) | 100 ug | Goat (3) | Serum | 3.93 L/ ongoing | 9 |
| *Clostridium perfringens* Epsilon toxin (inactivated) | 100 ug | Goat (3) | Serum | 4.07 L/ ongoing | 10 |
| rBVD2 E2 (gp53) purified protein | 150 ug | Goat (4) | Serum | | 6/ongoing |
| *Brachyspira hyodysenteriae* (strain B204) whole cell inactivated | 150 ug | Goat (3) | Serum | | 3/ongoing |
| *Brachyspira hyodysenteriae* (BR2019-12 strain) Pepsin digest | 150 ug | Goat (3) | Serum | | 3/ongoing |

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An adjuvant formulation comprising an oily phase and an aqueous phase, wherein the oily phase comprises at least 36% of the formulation v/v, wherein said formulation comprises monophosphoryl lipid A (MPL-A) or an analog thereof and an immunostimulatory oligonucleotide, wherein said adjuvant formulation is a water-in-oil emulsion.

2. The adjuvant formulation of claim 1, wherein
   the immunostimulatory oligonucleotide is a CpG or an oligoribonucleotide; and said formulation further comprises a polycationic carrier, wherein the polycationic carrier is selected from the group consisting of dextran, dextran DEAE (and derivatives thereof), PEGs, guar gums, chitosan derivatives, polycellulose derivatives like hydroxyethyl cellulose (HEC) polyethylenimene, poly aminos.

3. The adjuvant formulation according to claim 1, further comprising a glycolipid according to formula I

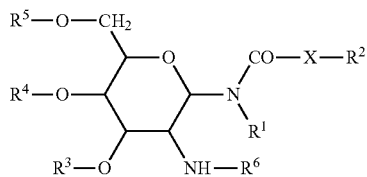

Formula I wherein, $R^1$ is hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

4. The adjuvant formulation of claim 3, wherein the glycolipid is N-(2-Deoxy-2-L-leucylamino-β-D-glucopyranosyl)-N-octadecyldodecanoylamide or a salt thereof.

5. The adjuvant formulation of claim 1, further comprising a sterol.

6. The adjuvant formulation of claim 5, further comprising a saponin.

7. The adjuvant formulation of claim 5, wherein the sterol is selected from the group consisting of ergosterol, lanosterol and cholesterol.

8. The adjuvant formulation of claim 1, comprising the source of aluminum, which is an aluminum hydroxide gel.

9. A vaccine composition comprising an effective amount of an antigen and the adjuvant formulation according to claim 1, wherein the oily phase of the composition is at least 40%.

10. The adjuvant formulation of claim 1, wherein the oily phase comprises over 45% of the vaccine composition v/v.

11. The adjuvant formulation of claim 1, wherein the oily phase comprises over 50% of the vaccine composition v/v.

12. A vaccine composition comprising the adjuvant formulation according to claim 11 and an effective amount of an antigen, wherein the antigen comprises at least one of viruses, bacteria, parasites, nucleic acid based antigens, polynucleotides, protein extract, cells, tissues, polysaccharides, glycoproteins, carbohydrates, fatty acids, teichioc acid, peptidoglycans, lipids, or glycolipids, and a combination thereof, wherein said vaccine composition is a W/O emulsion.

13. The vaccine composition according to claim 12, wherein antigen comprises at least one of viruses, bacteria, parasites, lipids, glycolipids or DNA vaccines.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg                                          23

<210> SEQ ID NO 2
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 2
tcgacgtcga tcggcgcgcg ccg                                          23

<210> SEQ ID NO 3
<211> LENGTH: 24
<212> TYPE: DNA
<213> ORGANISM: Artificial Sequence
<220> FEATURE:
<223> OTHER INFORMATION: CpG oligonucleotide

<400> SEQUENCE: 3
tcgacgtcga tcggcgcgcg ccgt                                         24

<210> SEQ ID NO 4
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: misc_feature
<222> LOCATION: (1)..(1)
<223> OTHER INFORMATION: n is 5'-Iodo-2'-deoxyuridine
<220> FEATURE:
<221> NAME/KEY: modified_base
<222> LOCATION: (1)..(1)
<223> OTHER INFORMATION: n is 5'-Iodo-2'-deoxyuridine

<400> SEQUENCE: 4
ncgacgtcga tcggcgcgcg ccg                                          23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: n is 5'-Iodo-2'-deoxyuridine
<220> FEATURE:
```

<221> NAME/KEY: misc_feature
<222> LOCATION: (1)..(1)
<223> OTHER INFORMATION: n is 5'-Iodo-2'-deoxyuridine

<400> SEQUENCE: 5
ncgacgtcga tcggcgcgcg ccgt                24

<210> SEQ ID NO 6
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: n is 5'-Iodo-2'-deoxyuridine
<220> FEATURE:
<221> NAME/KEY: misc_feature
<222> LOCATION: (1)..(1)
<223> OTHER INFORMATION: n is 5'-Iodo-2'-deoxyuridine

<400> SEQUENCE: 6
ncgacgtcga tcggcgcgcg ccgt                24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: n is 5'-Ethyl-2'-deoxyuridine
<220> FEATURE:
<221> NAME/KEY: misc_feature
<222> LOCATION: (1)..(1)
<223> OTHER INFORMATION: n is 5'-Ethyl-2'-deoxyuridine

<400> SEQUENCE: 7
ncgacgtcga tcggcgcgcg ccg                 23

<210> SEQ ID NO 8
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: n is 5'-Iodo-2'-deoxyuridine
<220> FEATURE:
<221> NAME/KEY: misc_feature
<222> LOCATION: (1)..(1)
<223> OTHER INFORMATION: n is 5'-Iodo-2'-deoxyuridine

<400> SEQUENCE: 8
ncgtcgacga tcggcggccg ccgt                24

<210> SEQ ID NO 9
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: n is 5'-Iodo-2'-deoxyuridine

```
<220> FEATURE:
<221> NAME/KEY: misc_feature
<222> LOCATION: (1)..(1)
<223> OTHER INFORMATION: n is 5'-Iodo-2'-deoxyuridine

<400> SEQUENCE: 9
ncgtcgacga tcggcggccg ccgt                                              24

<210> SEQ ID NO 10
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 10
tcgtcgacga tcggcgcgcg ccg                                               23

<210> SEQ ID NO 11
<211> LENGTH: 20
<212> TYPE: RNA
<213> ORGANISM: Artificial Sequence
<220> FEATURE:
<223> OTHER INFORMATION: immunostimulatory ORN

<400> SEQUENCE: 11
uuguuguugu uguuguuguu                                                   20

<210> SEQ ID NO 12
<211> LENGTH: 20
<212> TYPE: RNA
<213> ORGANISM: Artificial Sequence
<220> FEATURE:
<223> OTHER INFORMATION: immunostimulatory ORN

<400> SEQUENCE: 12
uuauuauuau uauuauuauu                                                   20

<210> SEQ ID NO 13
<211> LENGTH: 19
<212> TYPE: RNA
<213> ORGANISM: Artificial Sequence
<220> FEATURE:
<223> OTHER INFORMATION: immunostimulatory ORN

<400> SEQUENCE: 13
aaacgcucag ccaaagcag                                                    19

<210> SEQ ID NO 14
<211> LENGTH: 21
<212> TYPE: DNA
<213> ORGANISM: Artificial sequence
<220> FEATURE:
<223> OTHER INFORMATION: DNA/RNA; Synthesized
<220> FEATURE:
<221> NAME/KEY: misc_feature
<222> LOCATION: (11)..(17)
<223> OTHER INFORMATION: ribonucleotides

<400> SEQUENCE: 14
tcgtcgtttt guuguguttt t                                                 21
```